US010106589B2

(12) United States Patent
Aran Perramon et al.

(10) Patent No.: US 10,106,589 B2
(45) Date of Patent: Oct. 23, 2018

(54) COMPOSITIONS AND METHODS FOR IMMUNOMODULATION

(75) Inventors: Josep M Aran Perramon, Barcelona (ES); Rut Olivar Miro, Barcelona (ES)

(73) Assignee: FUNDACIO INSTITUT D'INVESTIGACIO BIOMEDICA DE BELLVITGE (IDIBELL), Barcelona (ES)

( * ) Notice: Subject to any disclaimer, the term of this patent is extended or adjusted under 35 U.S.C. 154(b) by 0 days.

(21) Appl. No.: 14/233,114

(22) PCT Filed: Jul. 16, 2012

(86) PCT No.: PCT/EP2012/063932
§ 371 (c)(1),
(2), (4) Date: Apr. 21, 2014

(87) PCT Pub. No.: WO2013/010998
PCT Pub. Date: Jan. 24, 2013

(65) Prior Publication Data
US 2014/0309158 A1 Oct. 16, 2014

(30) Foreign Application Priority Data

Jul. 15, 2011 (EP) .................................... 11382240

(51) Int. Cl.
C07K 14/47 (2006.01)
A61K 38/17 (2006.01)
C12N 5/0784 (2010.01)
A61K 35/15 (2015.01)
A61K 35/36 (2015.01)

(52) U.S. Cl.
CPC ............ *C07K 14/472* (2013.01); *A61K 35/15* (2013.01); *A61K 35/36* (2013.01); *A61K 38/1725* (2013.01); *C12N 5/0639* (2013.01); *C12N 2501/998* (2013.01)

(58) Field of Classification Search
CPC .................................................. C07K 14/472
See application file for complete search history.

(56) References Cited

U.S. PATENT DOCUMENTS

| 4,883,784 A | 11/1989 | Kaneko | |
| 5,719,127 A * | 2/1998 | Atkinson | A01K 67/0275 514/20.6 |
| 2007/0092933 A1* | 4/2007 | Gamier | C12N 15/62 435/69.1 |
| 2007/0104726 A1* | 5/2007 | Andreoletti | A61K 39/385 424/189.1 |
| 2008/0188404 A1* | 8/2008 | Medof | C07K 14/70596 424/178.1 |
| 2008/0293636 A1* | 11/2008 | Cohen | C07K 16/2896 514/1.1 |
| 2008/0311106 A1* | 12/2008 | Hill | A61K 39/385 424/130.1 |
| 2009/0324585 A1* | 12/2009 | Robinson | A01K 67/0278 514/1.1 |
| 2011/0064768 A1* | 3/2011 | Draper | A61K 39/015 424/218.1 |
| 2011/0286938 A1* | 11/2011 | Thurman | A61K 49/1812 424/9.323 |

FOREIGN PATENT DOCUMENTS

| EP | 0222611 A2 | 5/1987 | |
| JP | S62-201822 A | 5/1987 | |
| WO | 91/11461 A1 | 8/1991 | |
| WO | 2005051414 A1 | 6/2005 | |
| WO | WO 2005/051414 * | 6/2005 | ............. A61K 38/17 |

OTHER PUBLICATIONS

Sjoberg*et al. The Journal of Immunology Jun. 15, 2006 vol. 176 No. 12 7612-7620.*
Blom et al., 2001, Structural Requirements for the Complement Regulatory Activities of C4BP, The Journal of Biological Chemistry, 276(29): 27136-27144.*
Blom et al., 2003, CCP1-4 ofp the C4B-binding protein alpha-chain are required for factor I mediated cleavage of complement factor C3b, Molecular Immunology, 39: 547-556.*
Shalapour et al., 2015, Immunity, inflammation, and cancer: an eternal fight between good and evil, The Journal of Clinical Investigation, 125(9): 3347-3355.*
Xu et al., 2013, The Paradox Role of Regulatory T Cells in Ischemic Stroke, The Scientific World Journal, 2013: 8 pages.*
Ogun et al., 2008, Infection and immunity, 76(8): 3817-3823.*
Seya et al., 1999, Molecular remodeling of complement regulatory proteins for xenotransplantation, Immunopharmacology, 42: 75-80.*
Trouw et al., 2005, The Journal of Experimental Medicine, 201(12): 1937-1948.*
Sjoberg et al., 2006, The Journal of Immunology, 176: 7612-7620.*
"International Search Report for PCT/EP2012/063932 dated Feb. 19, 2013".
Bao, "Complement Factor H, Deficiency Accelerates Development of Lupus Nephritis", Journal of the American Society of Nephrology, Dec. 9, 2010, 285-295.
Blom, et al., "C4b-binding protein (C4BP) inhibits development of experimental arthritis in mice", Ann Rheum Dis 2009; 68: 136-142.
Blom, et al., "Structural requirements for the Complement Regulatory Activities of A4BP", The Journal of Biological Chemistry, vol. 276, No. 29, Issue of Jul. 20, pp. 27136-27144, 2001.

(Continued)

*Primary Examiner* — Amber D Steele
(74) *Attorney, Agent, or Firm* — Kramer Amado, P.C.

(57) ABSTRACT

The invention relates to methods and reagents for the treatment of immunological diseases. In particular, the invention relates to isoforms of the C4b-binding protein (C4BP) lacking beta chains as well as to fragments and peptides derived thereof and to the uses of these polypeptides for the treatment of immunological diseases such as immunoinflammatory disease, sepsis, an autoimmune disease, transplant rejection, graft-versus-host disease and a hypersensitivity disease. Moreover, the invention relates also the use of factor H for the treatment of immunological diseases. In addition, the invention relates to tolerogenic dendritic cells obtained using the C4BP isoform lacking beta chain, the peptides and fragments thereof and factor H and to the therapeutic uses of said cells.

16 Claims, 22 Drawing Sheets
Specification includes a Sequence Listing.

(56) References Cited

OTHER PUBLICATIONS

Blom Anna, et al., "Complement inhibitor C4b-binding protein—friend or foe in the innate immune system", Molecular Immunology, Apr. 2004, 1333-1346.
Clark, et al., "A CD40 Bridge between Innate and Adaptive Immunity", Immunity 2003. vol. 18, Issue 6, pp. 724-725.
Dahlback, "Purification of human C4b-binding protein and formation of tis complex with vitamin K-dependent protein S", Biochem, J. (1982=3) 209, 847-856.
Ekdahl, et al., "Systemic and intrathecal complement activation in multiple sclerosis and Guillan-Barre syndrome", Molecular Immunology, Sep. 1, 2009, 2848.
Ferreira, et al., "Complement control protein factor H: The good, the bad, and the inadequate", Molecular Immunology, Aug. 2010, 2187-2197.
Friese, et al., "Release of endogenous anti-inflammatory complement regulators FHL-1 and factor H protects synovial fibroblasts during rheumathoid arthritis", Clinical and Experimental Immunology, Jun. 1, 2003, 485-495.
Griffiths, et al., "Complement factor H, a marker of self, protects against experimental autoimmune encephalomyelitis", The Journal of Immunology, Apr. 1, 2009, 4368-4377.
Hardig Ylva, et al., "Expression and characterization of a recombinant C4b-binding protein lacking the beta-chain", Biochemical Journal, 1995, 795-800.
Heitger, et al., "Regulation of Expression and Function of IDO in Human Dendritic Cells", Current Medicinal Chemistry, 2011,18,2222-2233.
Jin, et al., "Molecular signatures of maturing dendritic cells: implications for testing the quality of dendritic cell therapies", Journal of Translational Medicine 2010, 8:4.
Jonuleit, et al., "Efficient transduction of mature CD83 dendritic cells using recombinant adenovirus suppressed T cell stimulatory capacity", Gene Therapy (2000) 7, 249-254.
Jonuleit, et al., "Induction of tumor peptide-specific cytotoxic T cells under serum-free conditions by mature human dendritic cells", Arch Dermatol Res (2000) 292: 325-332.
Kask Lena, et al., "Structural stability and heat-induced conformational change of two complement inhibitors: C4b-binding protein and factor H", Protein Science, May 2004, 1356-1364.
King, et al., "Human peripheral blood leucocyte non-obese diabetic-severe combined immunodeficiency interleukin-2 receptor gamma chain gene mouse model of xenogeneic graft-versus-host-like disease and the role of host major histocompatibility complex", Clinical and Experimental Immunology, 157: 104-118. 2009.
Machen, et al., "Antisense Oligonucleotides Down-Regulating Costimulation Confer Diabetes-Preventive Properties to Nonobese Diabetic Mouse Dendritic Cells", J. Immunol. 2004, 173, 4331-4341.
Moore, et al., "Interleukin-10 and the Interleukin-10 Receptor", Annu Rev. Immunol. 2001.19, 683-765.
Morelli, "Dendritic cells: regulators of alloimmunity and opportunities for tolerance induction.", Immunol Rev. 2003, 2003, 12-146.
Naranjo-Gomez, et al., "Comparative study of clinical grade human tolerogenic dendritic cells", Journal of Translational Medicine 2011,9:89.
Pluvinet, "RNA i-mediated silencing of CD40 prevents leukocyte adhesion on CD154-activated endothelial cells", Blood, Dec. 1, 2004, vol. 104, No. 12 pp. 3642-3646.
Ratzinger, et al., "Mature Human Langerhans Cells Derived from Derived from CD34 Hematopoietic Progenitors Stimulate Greater Cytolytic T Lymphocyte Activity in the Absence of Bioactive IL-12p70, by Either Single Peptide Presentation or Cross-Priming, Than Do Dermal-Interstiti", The Journal of Immunology, 2004, 173: 2780-2791.
Sanchez-Pernaute, et al., "Expression of the peptide C4b-binding protein Beta in the arthritic joint", Ann Rheum Dis 5006; 65:1279-1285.

Shinya, et al., "Quick method of multimeric protein production for biologically active substances such as human GM-CSF (hGM-CSF)", Biochemical and Biophysical Research Communications, Aug. 14, 2009, 40-44.
Steinman, "The Dendritic Cell System and its Role in Immunogenicity", Annu Rev. Immunol. 1991. 9:271-96. 1991.
Steinman, et al., "Tolerogenic Dendritic Cells", Annu. Rev. Immunol, 685-711.
Szeles, et al., "1,25-Dihydroxyvitamin D3 is an Autonomous Regulator of the Transcriptional Changes Leading to a Tolerogenic Dendritic Cell Phenotype", The Journal of Immunology, 2009, 182: 2074-2083.
Thurner, et al., "Generation of large numbers of fully mature and stable dendritic cells from leukapheresis products for clinical application", Journal of Immunological Methods 223(1999) 1-15.
Van Etten, et al., "Immunoregulation by 1,25-dihydroxivitamin D3: Basic concepts", Journal of Steriod Biochemistry & Biology, 2005, 93-101.
Walsh, et al., "Tregs and transplantation tolerance", The Journal of Clinical Investigation vol. 114, No. 10, Nov. 2004 pp. 1398-1403.
Wenderfer, et al., "Analysis of C4 and the C4 binding protein in the MRL/Ipr mouse", Arthritis Research & Therapy 2007, 9:R114.
Xiao Bao-Guo, et al., "Tolerogenic dendritic cells: the ins and outs of outcome", Journal of Immunotherapy, Jan. 1, 2006, 465-471.
Balkwill, et al., "Inflammation and cancer: back to Virchow?", The Lancet (2001) vol. 357, 539-540.
Huang, MD, et al., "Inflammation in stroke and focal cerebral ischemia", Surgical Neurology 66 (2006) 232-245.
Jin, et al., "Inflammatory mechanisms in ischemic stroke: role of inflammatory cells", Journal of Leukocyte Biology (2010), vol. 87, pp. 1-11.
Jin, et al., "Inhibition of Breast Cancer Resistance Protein (ABCG2) in Human Myeloid Dendritic Cells Induces Potent Tolerogenic Functions during LPS Stimulation", PLOS ONE (Aug. 2014) vol. 9, Issue 8.
Morjani, et al., "Immunosuppressors as Multidrug Resistance", Methods in Molecular Biology (2010), vol. 596, pp. 433-446.
Olivar, et al., "The A7B0 Iso form of the Complement Regulator C4b-Binding Protein Induces a Semimature, Anti-Inflammatory State in Dendritic Cells", The Journal of Immunology (2013) 2857-2872 plus Supplementary Material.
Rakoff-Nahoum, "Why Cancer and Inflammation?", Yale Journal of Biology and Medicine (2006) 79: 123-130.
Ross, "Modulation of drug resistance transporters as a strategy for treating myelodysplastic syndrome", Best Practice & Resarch Clinical Haemetology (2004) vol. 17, No. 4, pp. 641-651.
Blom, et al., "CCPI-4 of the C4b-binding protein a-chain are required for factor I lnediated cleavage of co1nplement factor C3b", Molecular Immunology 39 (2003) 547-556.
Tsukimoto, et al., "2014-520633 2 24 29", Radioisotopes, 57, 593-595 (2008).
Citation 8, Experimental Medicine, 2008, vol. 26, No. 20, pp. 3211-3217.
Chorny, et al., "Regulation of Dendritic Cell Differentiation by Vasoactive Intestinal Peptide", Ann. N.Y. Acad. Sci. 1088: 187-194 (2006).
Fujita, et al., "Regulatory Dendritic cells protect against cutaneous chronic graft-versus-host disease mediated through CD4+CD25+Foxp3+ regulatory T cells", Blood, Nov. 15, 2007, vol. 110, No. 10, pp. 3793-3803.
Happonen, et al., "Complement Inhibitor C4b-Binding Protein Interacts Direclty with Small Glycoproteins of the Extracellular Matrix", J. Immunol 2009; 182: 1518-1525.
Kavousanaki, et al., "Novel Role of Plasmacytoid Dendritic Cells in Humans", Arthritis & Rheumatism, vol. 62, No. 1, Jan. 2010, pp. 53-63.
Pei, et al., "Inflammation in the pathogenesis of ischemic stroke", Frontiers in Bioscience, Landmark, 20, 772-783, Jan. 1, 2015.
Rottman, et al., "Mouse Models of Systemic Lupus Erythematosus Reveal a Complex Pathogenesis", Veterinary Pathology, 47(4) 664-676, 2010.

(56) References Cited

OTHER PUBLICATIONS

Sato, et al., "Modified myeloid dendritic cells act as regulatory dendritic cells to induce anergic and regulatory T cells", Blood, May 1, 2003, vol. 101, No. 9, pp. 3581-3589.

Sato, et al., "Regulatory Dendriti Cells Protect Mice from Murine Acute Graft-Versus-Hot Disease and Leukemia Relapse", Immunity, vol. 18, 367-379, Mar. 2003.

Yang, et al., "Reservatrol Pretreatment Protected against Cerebral Ischemia/ Reperfusion Injury in Rats via Expansion of T Regulatory Cells", Journal of Stroke and Cerebrovascular Diseases, 2016 (8): 1914-21.

Chen, et al., "The Complement System in Systemic Autoimmune Disease", Journal of Autoimmunity 34 (2010) 276-286.

* cited by examiner

A)

B)

COMPOSITIONS AND METHODS FOR IMMUNOMODULATION

FIELD OF THE INVENTION

The invention relates to the field of immunology and, more in particular, to compositions based on isoforms of the complement C4BP lacking β chains and factor H which are capable of inducing a tolerogenic state in dendritic cells and to the uses thereof for the prevention and/or treatment of diseases characterized by a un undesired activation of the immune system.

BACKGROUND OF THE INVENTION

Dendritic cells (DC) are the professional APC of the immune system. At their immature stage, DC take up extracellular antigens by means of phagocytosis or pinocytosis and process the antigens to peptides in the endocytotic compartment such as endosomes and phagosomes, where peptides are bound to MHC class II molecules. They also have the unique ability of loading the peptides from exogenous proteins to the MHC class I pathway of presentation, a process called "cross-presentation". Given the appropriate differentiation signals (such as microbial products), immature DC may develop into an immunogenic DC which is equipped with the ability to activate both naive and memory T cells. On the other side of the spectrum immature DC can also differentiate into a tolerogenic phenotype, which is thought to play a crucial role in the maintenance of peripheral tolerance (Steinman, Ann. Rev. Immunol. 2003, 21: 685-711; Morelli, Immunol Rev 2003: 125-146).

Numerous protocols for the generation of tolerogenic DC in vitro have been described (Xiao et al., J. Immunother. 2006 (29) 465-471). The most well-characterized methods utilise pharmacological mediators (such as immunosuppressive drugs including vitamin D3 analogues, glucocorticoids, oestrogen), cytokines and growth factors (such as IL-10, TGF-beta, IL-4 and IFN-gamma) or genetic engineering, either to suppress the expression of T cell co-stimulatory molecules (such as CD86 and CD40) or to enhance the expression of T cell inhibitory molecules (such as CTLA-4 and indoleamine 2,3-dioxygenase).

The activated form of vitamin D, 1,25-dihydroxyvitamin D3 (1,25(OH)2D3), is a secos-teroid hormone that has, in addition to its central function in calcium and bone metabolism, important effects on the growth and differentiation of many cell types and pronounced immunoregulatory properties (van Etten et al., J Steroid Biochem and MoI Biol 2005 (97) 93-101). The biological effect of 1,25(OH)2D3 is mediated by the vitamin D receptor (VDR), a member of the superfamily of nuclear hormone receptors functioning as an agonist-activated transcription factor that binds to specific DNA sequence elements, vitamin D responsive elements, in vitamin D responsive genes and ultimately influences their rate of RNA polymerase II-mediated transcription. APC, and notably DC, express the VDR and are key targets of VDR agonists in vitro and in vivo. IL-10 is produced mainly by activated lymphocytes, monocytes and macrophages. IL-10 binds to a receptor composed of two subunits, the ligand-binding IL-10R1 and signalling IL-10R2. IL-10 down-regulates MHC class II and co-stimulatory molecule expression, IL-12 and proinflammatory cytokine secretion and T cell stimulatory function of several APC (Moore et al., Ann Rev Immunol 2001 (19)683-785).

Genetic manipulation of DC, such as inhibition of T cell co-stimulatory molecules, CD40, CD80 and CD86 by the use of antisense oligonucleotides has proven effective in generating tolerogenic DC (Machen et al., J. Immunol. 2004, 173: 4331-4341). Such DC produced reduced levels of IL-12p70 and TNF-alpha and prevented diabetes in non-obese diabetic mice.

To date, the majority of therapies approved by the US FDA for autoimmune disease have focused on the systemic inhibition of immune inflammatory activity. Although non-specific immune suppression is partially effective in inhibiting auto-reactive immune cell function, the drugs used to suppress the immune response have numerous side effects and continuous therapy is not conductive to long-term host survival. Thus, it is desirable to develop auto-antigen-specific treatments that allow for the specific blockade of the deleterious effects of self-reactive immune cell function, while maintaining the ability of the immune system to clear infection. Hence, there is a strong need for methods that generate properly equipped DC that can efficiently induce antigen-specific immune tolerance.

In addition, ex vivo generated DC with appropriate tolerogenic function could also be implemented as therapeutic vaccine in treatment of allergy and for induction of transplant tolerance. As with immunotherapy for autoimmune diseases, efficient suppression of harmful immune responses involves the tolerance induction of both CD4+ and CD8+ T cells. Therefore, one can expect that ex vivo generated tolerogenic DC should have the same characteristics for treating autoimmune diseases, allergy and for prevention of graft rejection.

However, new and alternative methods for the production of tolerogenic dendritic cells having a distinct tolerogenic phenotype and having expression of tolerogenic determinants is always a recurring object of research in this field.

SUMMARY OF THE INVENTION

The invention relates to a C4BP iso form lacking the beta chain for use in the prevention and/or treatment of an immunological disease. The invention also relates to a polypeptide comprising the CCP6 domain of the C4BP alpha chain or a functionally equivalent variant thereof, wherein said polypeptide does not comprise the full-length C4BP alpha chain and wherein said polypeptide does not comprise a region of a protein different from C4BP, and to a peptide having the sequence selected from the group consisting of SEQ ID NO:2, 3, 4 and 5 or a functionally equivalent variant thereof, to polynucleotides encoding said polypeptide or peptides and to vectors comprising said polynucleotides.

In another aspect, the invention relates to a pharmaceutical composition comprising a polypeptide, a peptide, a polynucleotide or a vector according to the invention.

In another aspect, the invention relates to a composition of matter selected from the group consisting of
  (i) Factor H or a functionally equivalent variant thereof
  (ii) A polynucleotide encoding a Factor H or a functionally equivalent variant thereof
  (iii) A vector comprising a polynucleotide encoding a Factor H or a functionally equivalent variant thereof
for use in the prevention and/or treatment of an immunological disease.

In another aspect, the invention relates to a method for the generation of a population of tolerogenic dendritic cells comprising the steps of
  (i) incubating a population of dendritic precursor cells under conditions adequate for the formation of a population of immature dendritic cells and (ii) incubating the population of immature dendritic cells obtained in step (i) under conditions adequate for the formation of mature dendrite cells wherein steps (i) and/or (ii) are carried out in the presence of a composition of matter selected from the group consisting of
(a) C4BP iso form lacking the beta chain,
(b) a polypeptide according to the invention
(c) a peptide according to the invention,
(d) a polynucleotide according to the invention
(e) a vector according to the invention,
(f) Factor H or a functionally equivalent variant thereof,
(g) A polynucleotide encoding a Factor H or a functionally equivalent variant thereof and
(h) A vector comprising a polynucleotide encoding a Factor H or a functionally equivalent variant thereof.

In yet another aspect, the invention relates to a tolerogenic dendritic cell obtained by the method according to the invention, to a pharmaceutical composition comprising a tolerogenic dendritic cell population of the invention and to the uses of the tolerogenic dendritic cell population of the invention for the prevention and/or treatment of an immunological disease.

The viability of Mo-DCs obtained by C4BP $\alpha7\beta0$ or C4BP $\alpha7\beta1$ treatment (2 µg/ml) and matured with LPS was assessed by Annexin-V plus 7-ADD staining and flow cytometry analysis, as described in Materials and Methods. As reference, we included Mo-DCs treated with the immunosupressor Vitamin D3 (calcitriol, Calcigex®, Abbott Laboratories, S.A.; 2.4 µM). iDC, untreated, immature DCs; mDC, untreated, LPS-matured DCs. The results shown are the mean+/−SD from 8 independent experiments.

Figure 3:
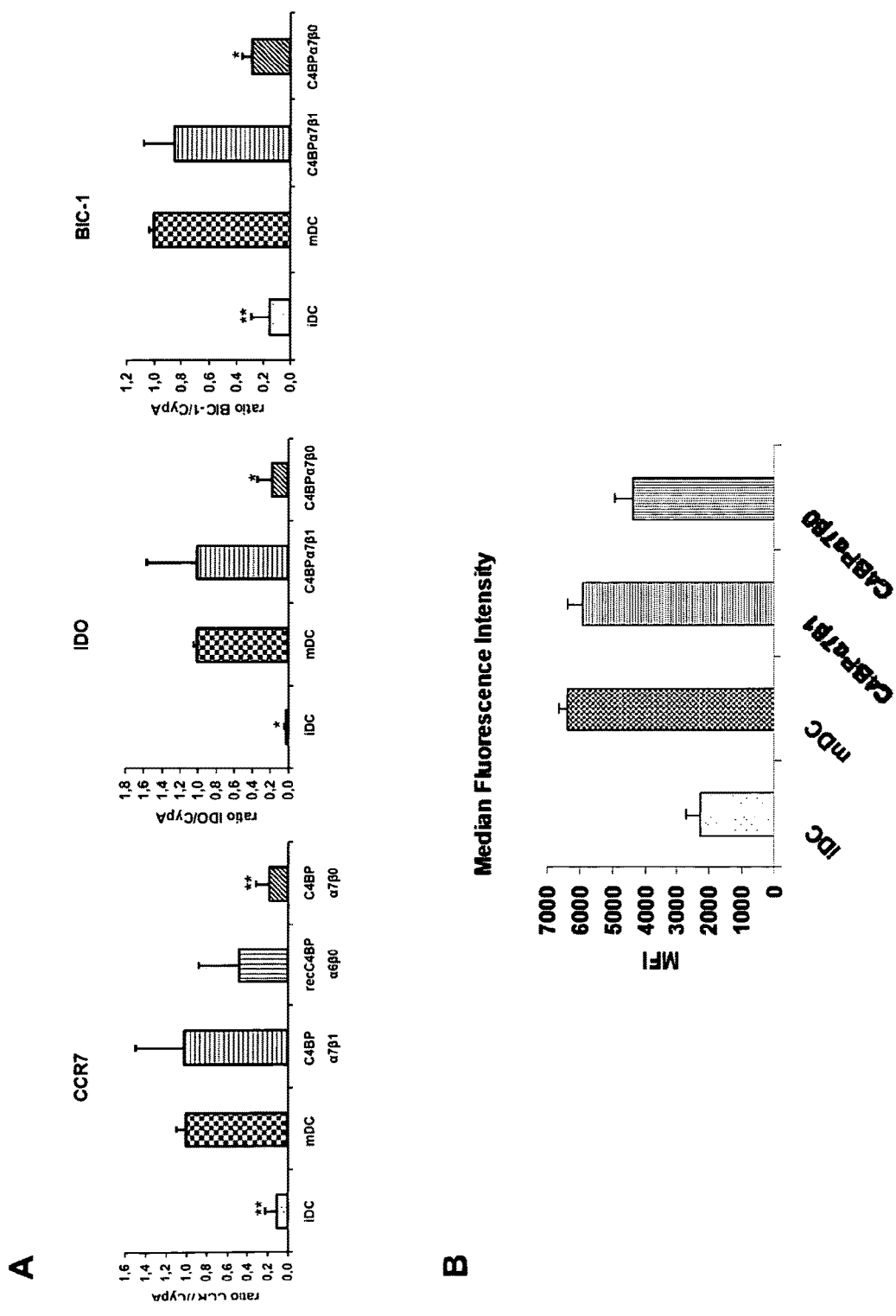

FIG. 3. Human Mo-DCs exposed to C4BP isoforms lacking beta chain express less CCR7 and DC maturation markers IDO and BIC-1

(A) Gene expression profile of C4BP-treated and LPS-matured Mo-DCs. Relative quantification of CCR7, IDO, and BIC-1 gene expression by RT-qPCR using the LightCycler® technology. Results shown are the mean+/−SD from 6 (CCR7), 4 (IDO), and 3 (BIC-1) independent experiments. (B) CCR7 surface expression analysis on C4BP-treated and LPS-matured Mo-DCs by flow cytometry (MFI). Results shown are the mean+/−SD from 3 independent experiments. iDC, untreated, immature DCs; mDC, untreated, LPS-matured DCs. (*, $p<0.05$; **, $p<0.01$ respect to mDC).

Figure 4:
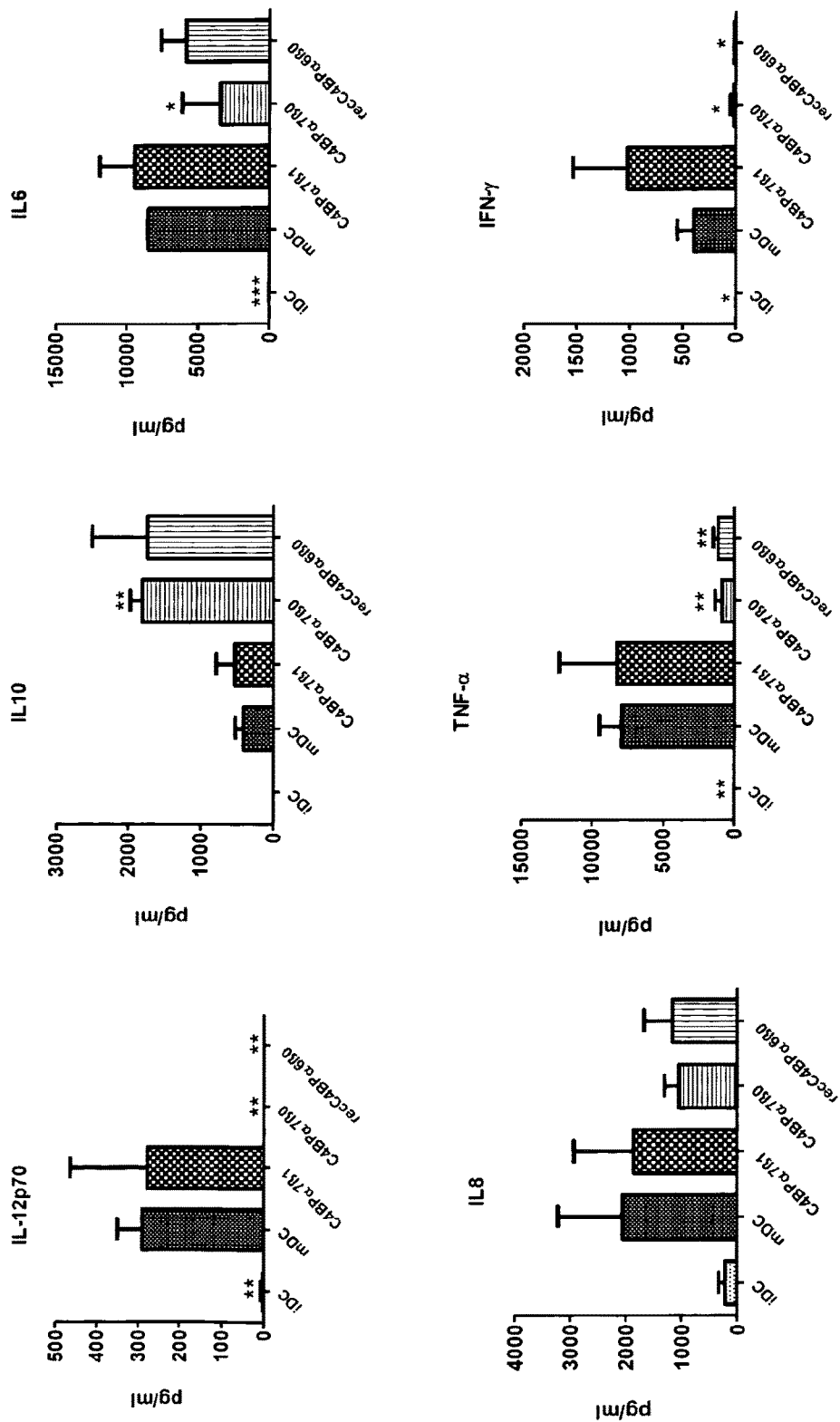

FIG. 4. C4BP isoforms lacking beta chain inhibit the release of inflammatory cytokines by LPS-matured human Mo-DCs Mo-DCs treated with the different C4BP isoforms at 2 µg/ml were matured with LPS and the concentrations of IL-12p70, IL-10, IL-6, IL-8, TNF-$\alpha$ and IFN-$\gamma$ were analyzed in the respective supernatants. Results shown are the mean+/−SD from 3 independent experiments, performed in duplicate. iDC, untreated, immature DCs; mDC, untreated, LPS-matured DCs. (*, $p<0.05$; , $p<0.01$; *, $p<0.001$ respect to mDC).

Figure 5:
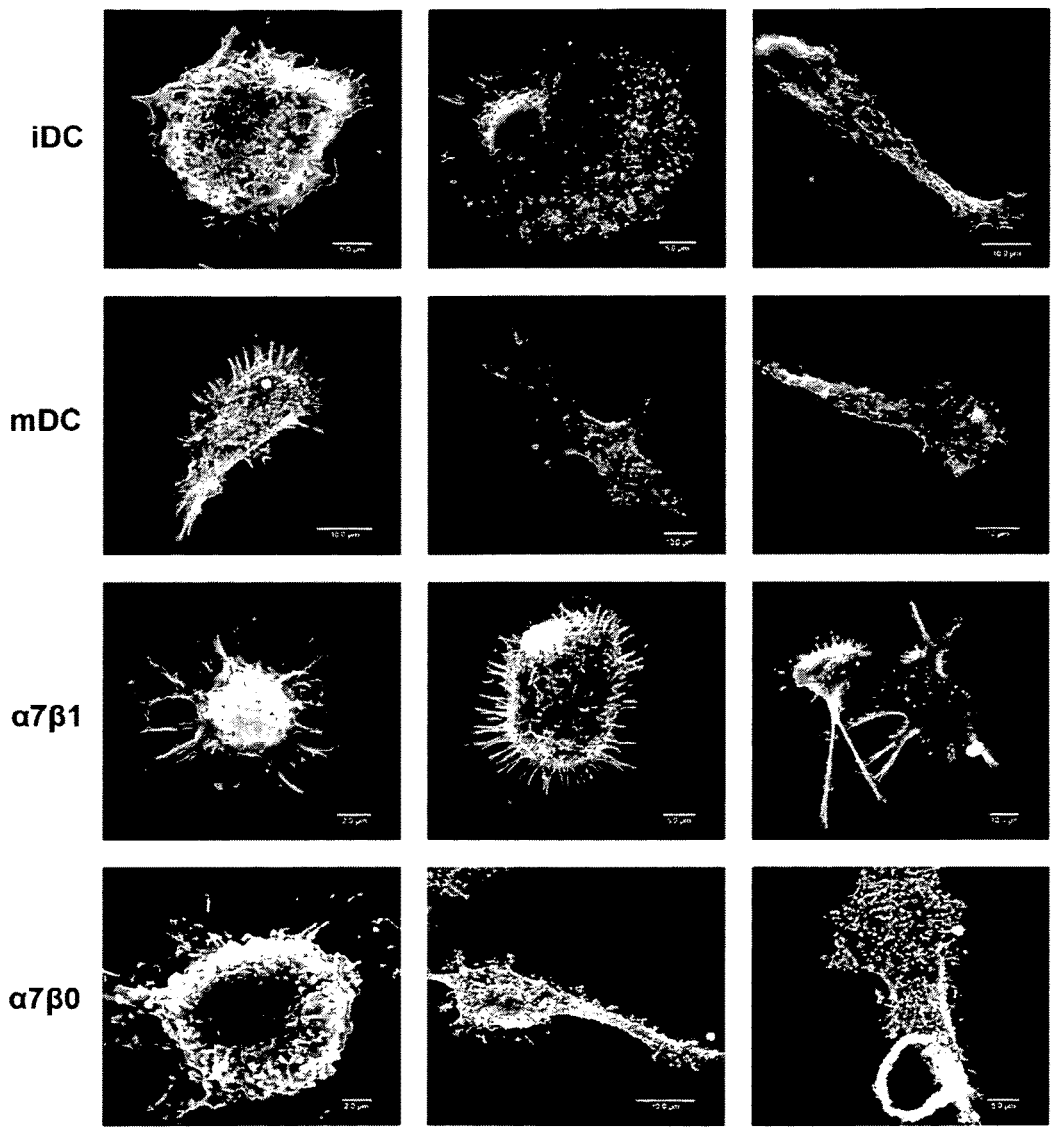

FIG. 5. C4BP isoforms lacking beta chain modify the morphology of human Mo-DCs

The surface morphology of Mo-DCs treated with the main C4BP isoforms ($\alpha7\beta0$ or $\alpha7\beta1$) at 2 µg/ml and matured with LPS was examined by SEM, and compared with those from both untreated, immature (iDC) and LPS-matured (mDC) DCs. Note the absence of long dendritic projections in C4BP $\alpha7\beta0$-treated DCs, more closely resembling to the immature DC phenotype.

Figure 6:
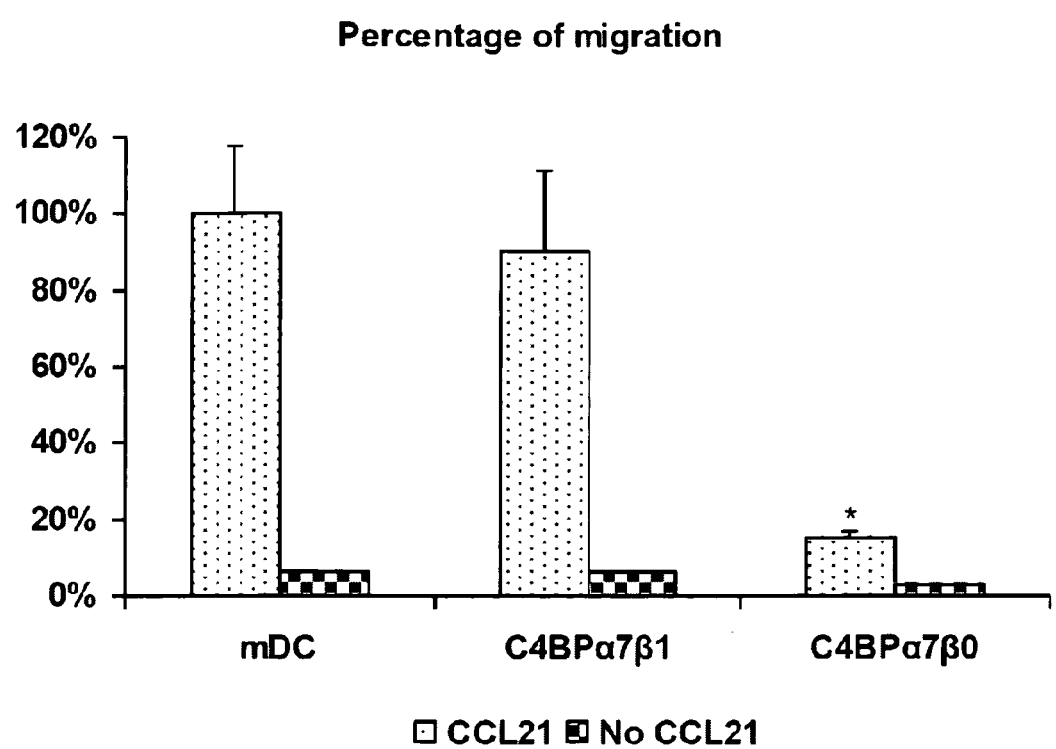

FIG. 6. C4BP isoforms lacking beta chain alter the chemotaxis of human Mo-DCs

Migration of untreated and C4BP-treated Mo-DCs after LPS maturation towards the chemokine CCL21 was assessed in a transwell assay. Shown are the percentages of DCs migrated toward the lower CCL21-containing chamber after 2 h incubation, relative to the migration values from untreated, LPS-matured DCs (mDC) (100%). Spontaneous migration of DCs towards a lower chamber without CCL21 was also assessed. Results are the mean+/−SD from 4 independent experiments performed in duplicate. (*, $p<0.05$ respect to mDC).

Figure 7:
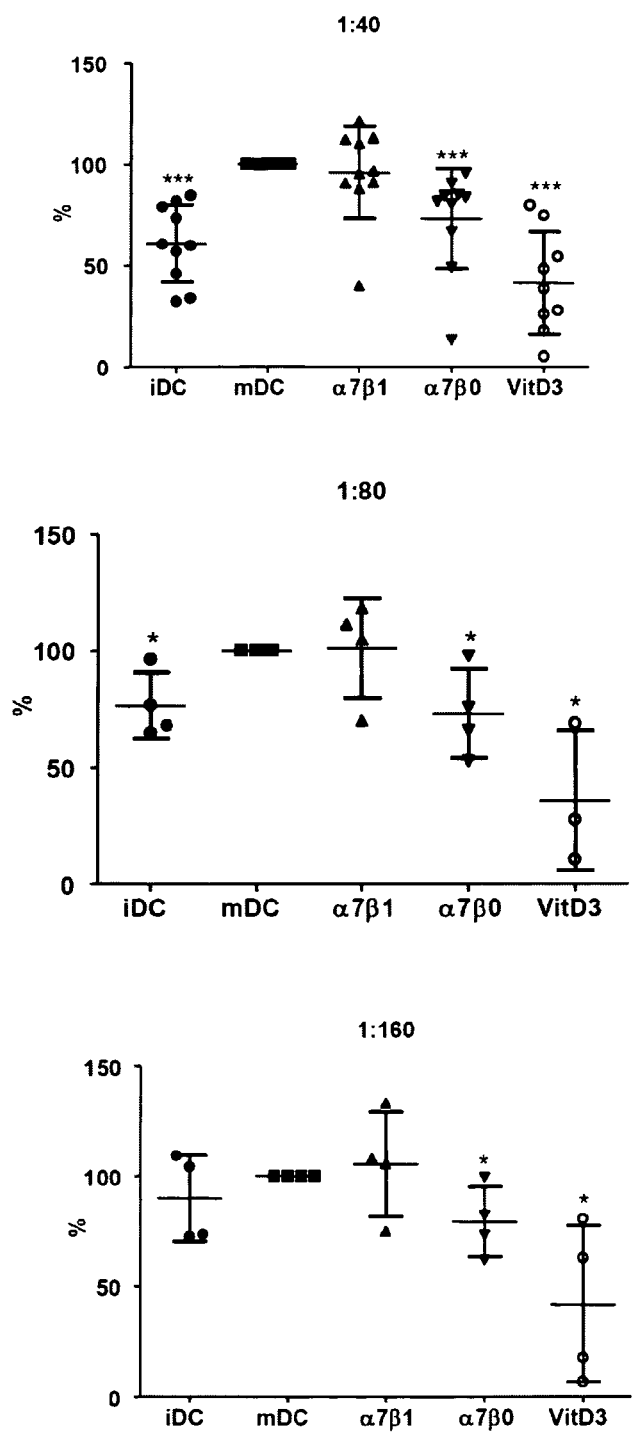

FIG. 7. Human Mo-DCs exposed to C4BP isoforms lacking beta chain inhibit allogeneic T cell proliferation Untreated (mDC), C4BP-treated ($\alpha7\beta0$ or $\alpha7\beta1$, at 2 µg/ml) or VitD3-treated (calcitriol, Calcigex®, Abbott Laboratories, S.A.; 2.4 µM), and LPS-matured Mo-DCs were cultured in triplicate with allogeneic, purified CD3' T cells ($10^5$/well) at 1:40 (n=10), 1:80 and 1:160 (both n=4) DC:T cell ratio for 5 days. [$^3$H] Thymidine (1 µCi/well) was added for the last 16 h of culture, and incorporation was measured by a $\beta$-plate counter (*, $p<0.05$; , $p<0.01$; *, $p<0.001$ respect to mDC). iDC, untreated, immature DCs.

Figure 8:
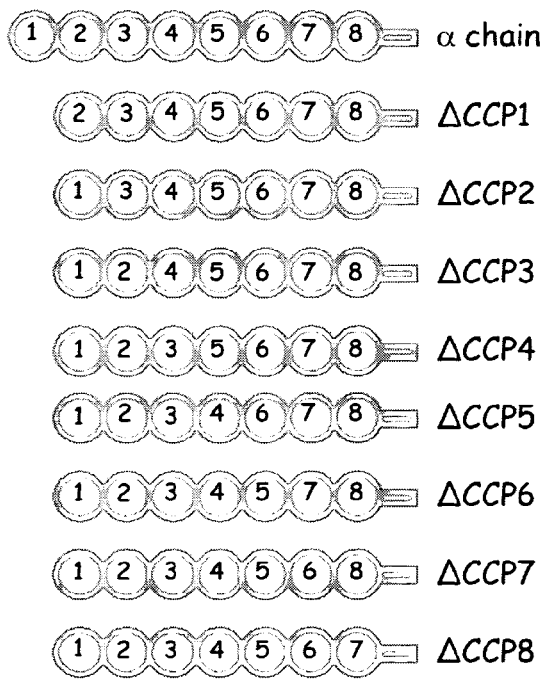
Figure 8:
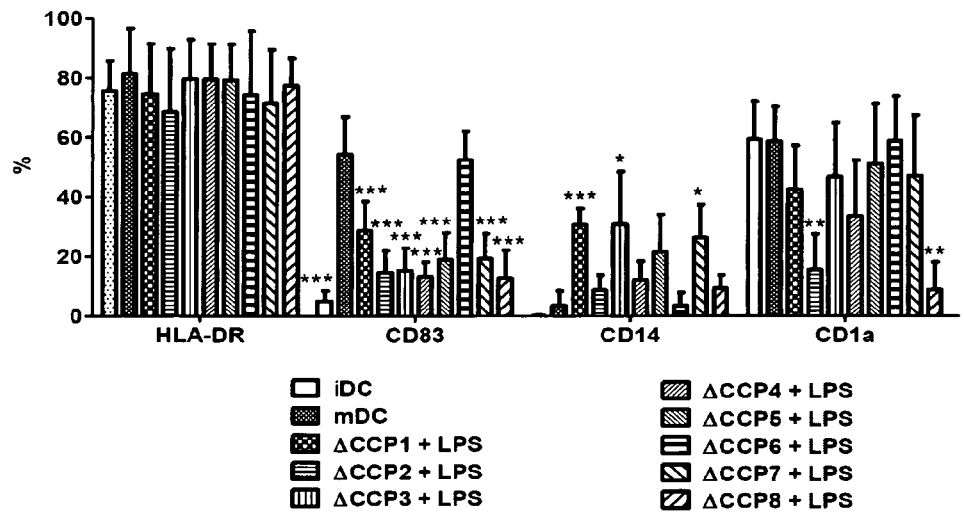
Figure 8:
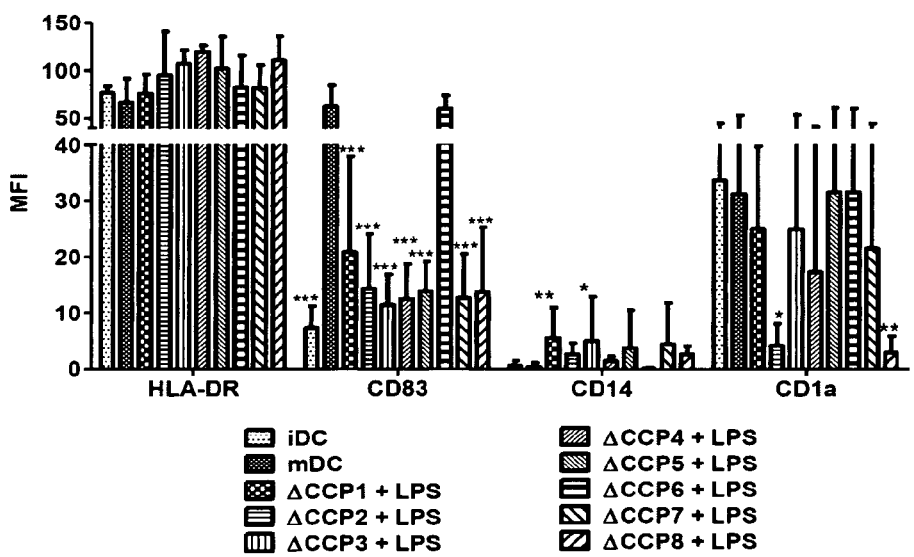

FIG. 8. The CCP6 domain of C4BPA is necessary for the "tolerogenic" activity of C4BP over human Mo-DCs.

Human Mo-DCs were incubated throughout their differentiation and maturation process with the indicated concentrations of the C4BP $\alpha$-chain CCP deletion mutants ($\Delta$CCP1 to $\Delta$CCP8; all at 2 µg/ml) (A). DC maturation was achieved by LPS treatment (5 µg/ml). Cells were then collected, washed, and analyzed by flow cytometry for cell surface expression of CD14, CD83, CD1a and HLA-DR. Columns represent the percentage of positive cells (B), and the MFI (C) for the different surface markers. iDC, untreated, immature DCs; mDC, untreated, LPS-matured DCs. The results shown are the mean+/−SD from 8 independent experiments (*, $p<0.05$; , $p<0.01$; *, $p<0.001$ respect to mDC).

Figure 9:
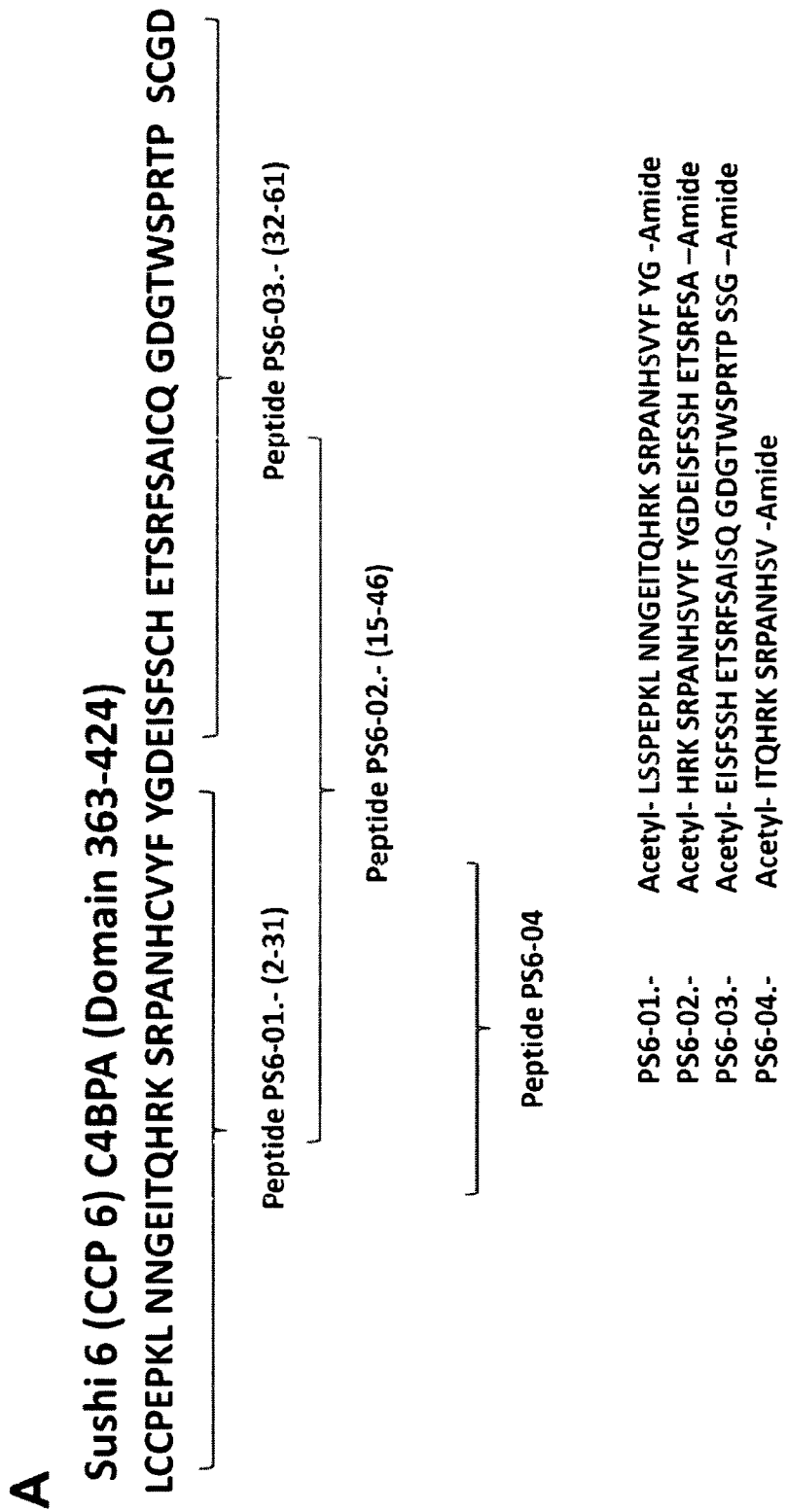
Figure 9:
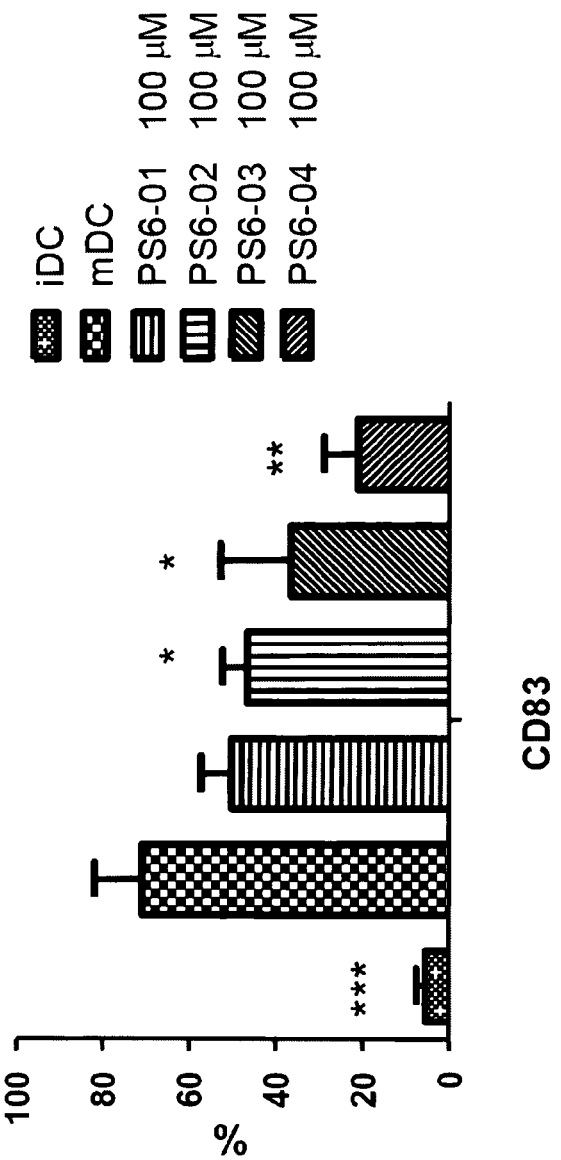

FIG. 9. CCP6-based peptide PS6-04 prevents the maturation phenotype of human Mo-DCs (A) Lineal representation of the CCP6 amino acid sequence and the four CCP6-based peptides employed. (B) Human Mo-DCs were incubated throughout their differentiation and maturation process with PS6-01, PS6-02, PS6-03, or PS6-04 peptide (all at 100 µM). DC maturation was achieved by LPS treatment (5 µg/ml). Cells were then collected, washed, and analyzed by flow cytometry for cell surface expression of the specific DC maturation marker CD83. Columns represent the percentage of positive cells (%), and the median fluorescence intensity (MFI). iDC, untreated, immature DCs; mDC, untreated, LPS-matured DCs. The results shown are the mean+/−SD from 3 independent experiments (*, p<0.05; , p<0.01; *, p<0.001 respect to mDC). n.d., not determined.

Figure 10:
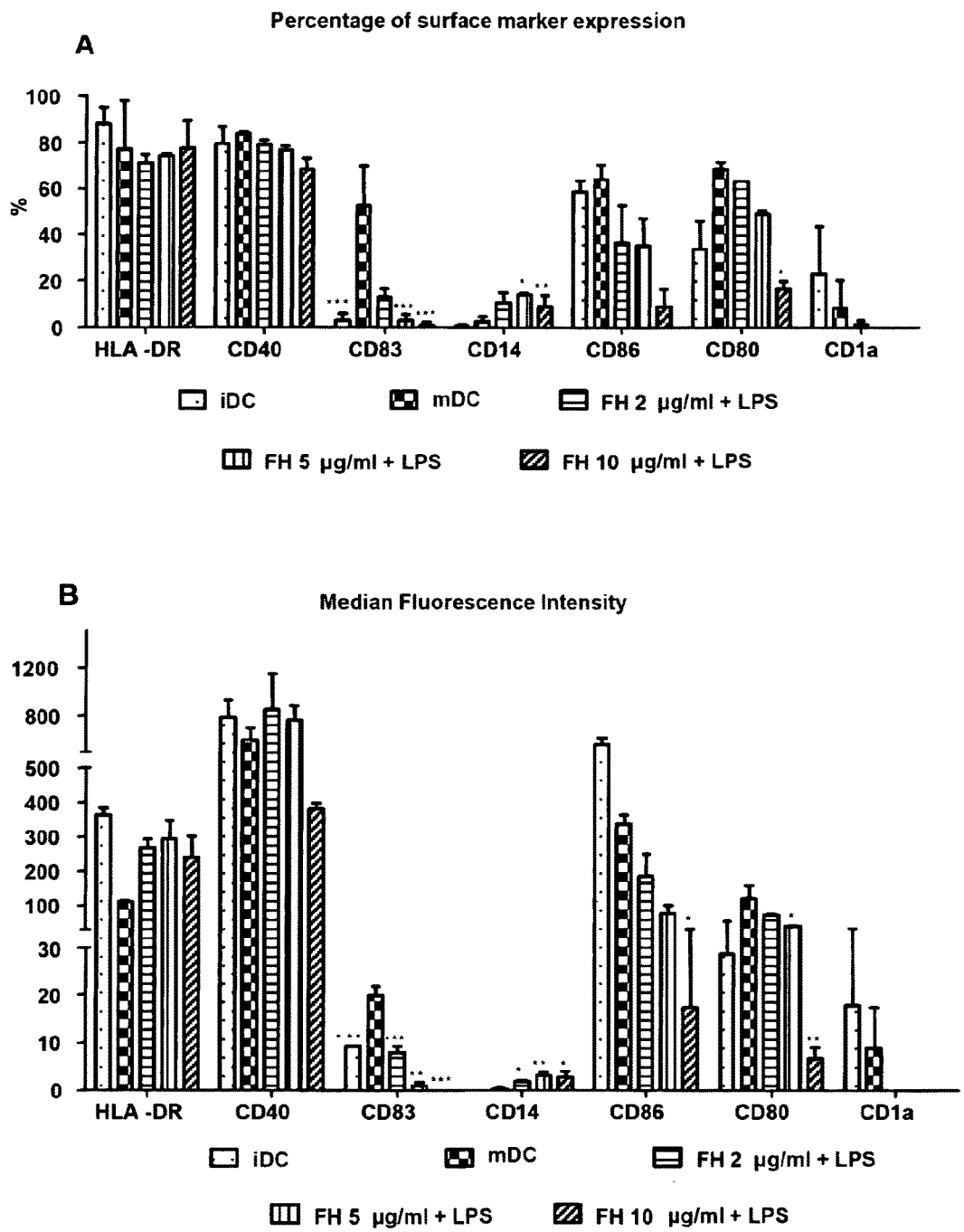

FIG. 10. Factor H down-regulates the activation phenotype of human Mo-DCs

Factor H inhibits up-regulation of key surface markers from human Mo-DCs. Human Mo-DCs were incubated throughout their differentiation and maturation process with the indicated concentrations of Factor H. DC maturation was achieved by LPS treatment (see Materials and Methods for details). Cells were then collected, washed, and analyzed by flow cytometry for cell surface expression of CD14, CD40, CD80, CD83, CD86, CD1a and HLA-DR. Columns represent the percentage of positive cells (A), and the MFI (B) for the different surface markers. iDC, untreated, immature DCs; mDC, untreated, LPS-matured DCs. The results shown are the mean+/−SD from 5 independent experiments (*, p<0.05; , p<0.01; *, p<0.001 respect to mDC).

Figure 11:
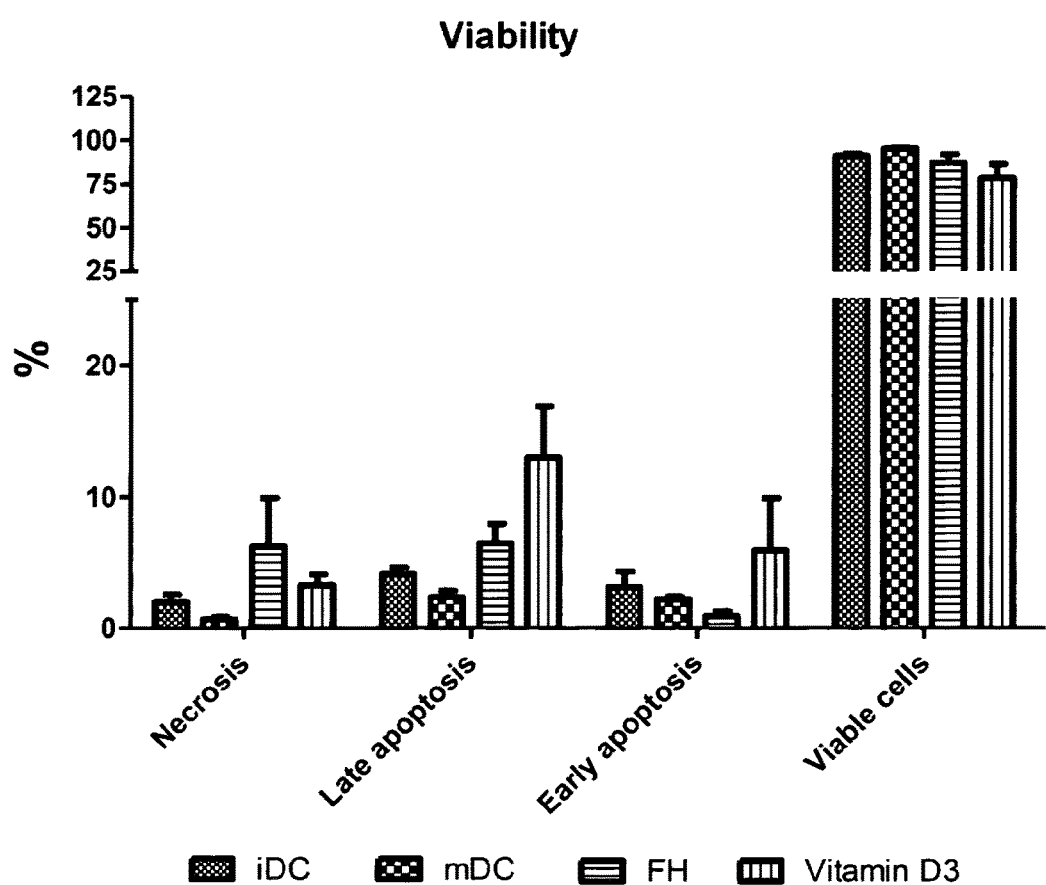

FIG. 11. Factor H treatment does not affect the viability of human Mo-DCs

The viability of Mo-DCs obtained by Factor H treatment (5 µg/ml) and matured with LPS was assessed by Annexin-V plus 7-ADD staining and flow cytometry analysis, as described in Materials and Methods. As reference, we included Mo-DCs treated with the immunossupressor Vitamin D3 (calcitriol, Calcigex®, Abbott Laboratories, S.A.; 2.4 µM). iDC, untreated, immature DCs; mDC, untreated, LPS-matured DCs. The results shown are the mean+/−SD from 8 independent experiments.

Figure 12:
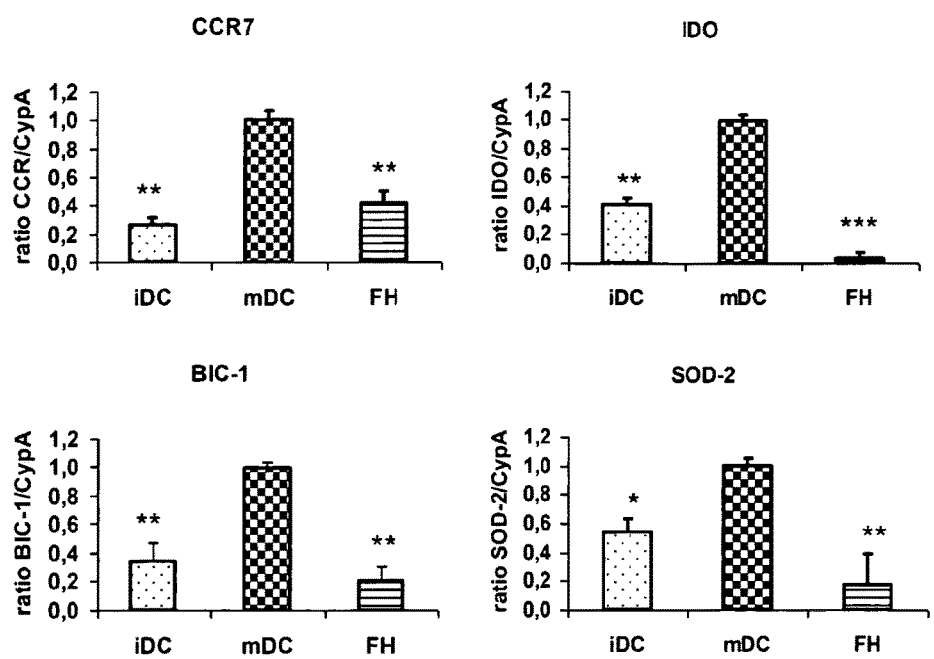
Figure 12:
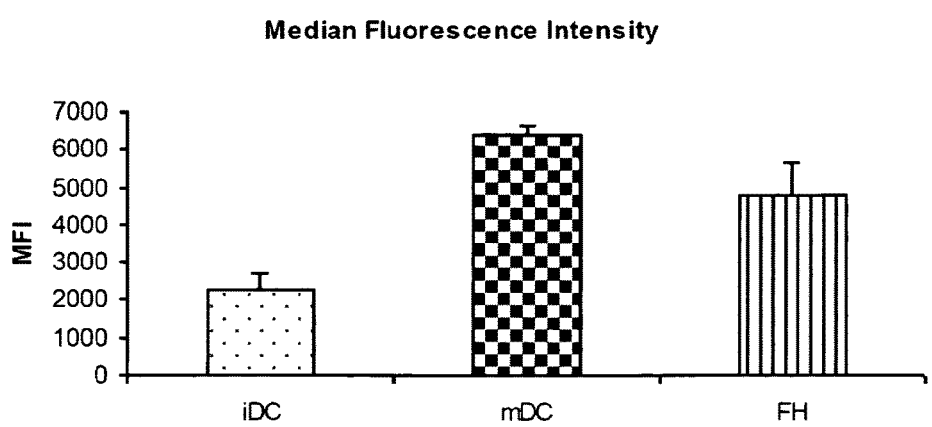

FIG. 12. Human Mo-DCs exposed to Factor H express less CCR7 and DC maturation markers IDO, BIC-1 and SOD2

(A) Gene expression profile of Factor H-treated (5 µg/ml) and LPS-matured Mo-DCs. Relative quantification of CCR7, IDO, BIC-1, and SOD2 gene expression by RT-qPCR using the LightCycler® technology. Results shown are the mean+/−SD from 4 independent experiments. (B) CCR7 surface expression analysis on Factor H-treated and LPS-matured Mo-DCs by flow cytometry (MFI). Results shown are the mean+/−SD from 3 independent experiments. iDC, untreated, immature DCs; mDC, untreated, LPS-matured DCs. (*, p<0.05; , p<0.01; *, p<0.001 respect to mDC).

Figure 13:
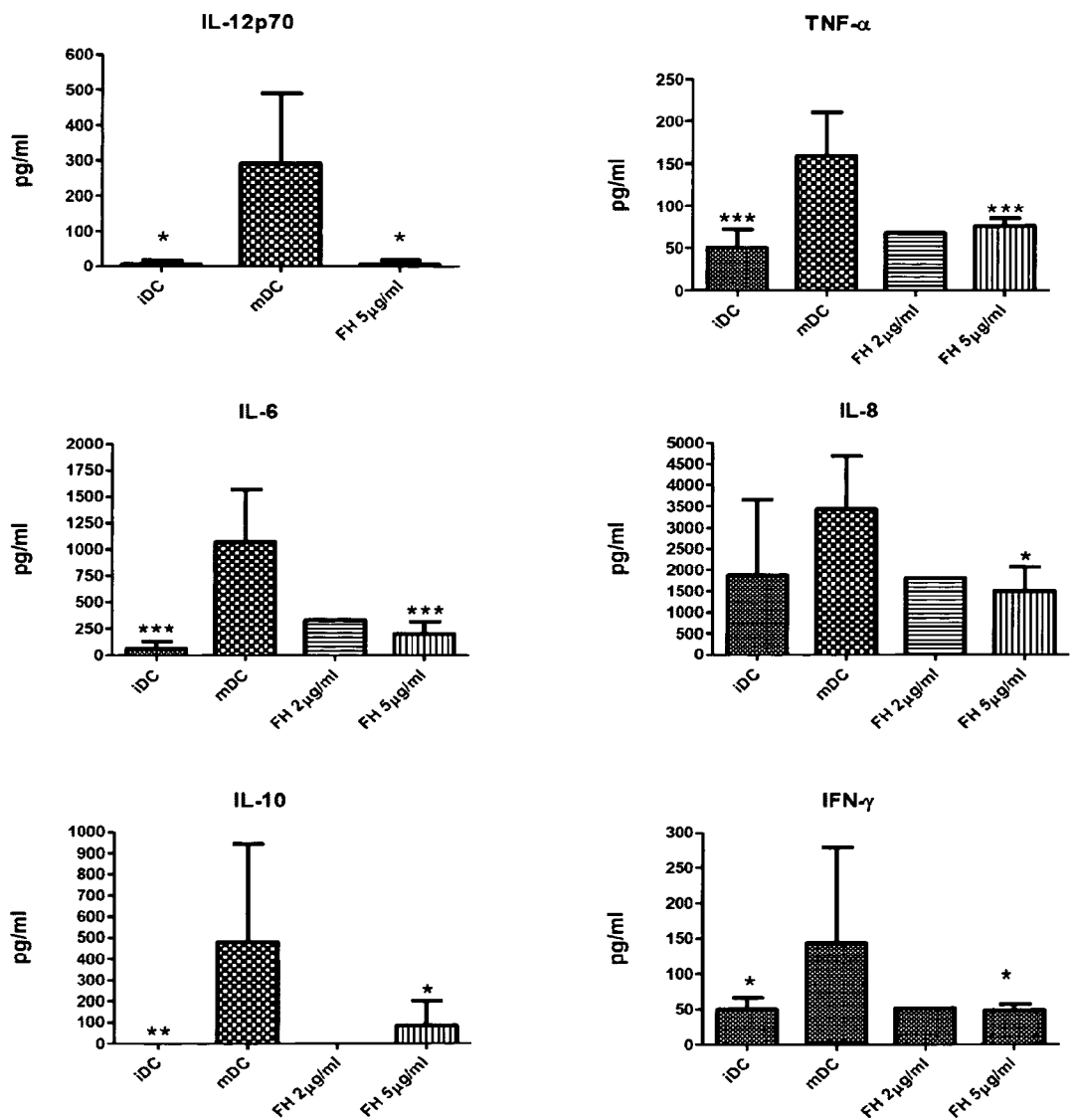

FIG. 13. Factor H inhibits the release of inflammatory cytokines by LPS-matured human Mo-DCs Mo-DCs treated with the different C4BP isoforms at 5 µg/ml were matured with LPS and the concentrations of IL-12p70, IL-10, IL-6, IL-8, TNF-α and IFN-γ were analyzed in the respective supernatants. Results shown are the mean+/−SD from 4 independent experiments, performed in duplicate. iDC, untreated, immature DCs; mDC, untreated, LPS-matured DCs. (*, p<0.05; , p<0.01; *, p<0.001 respect to mDC).

Figure 14:
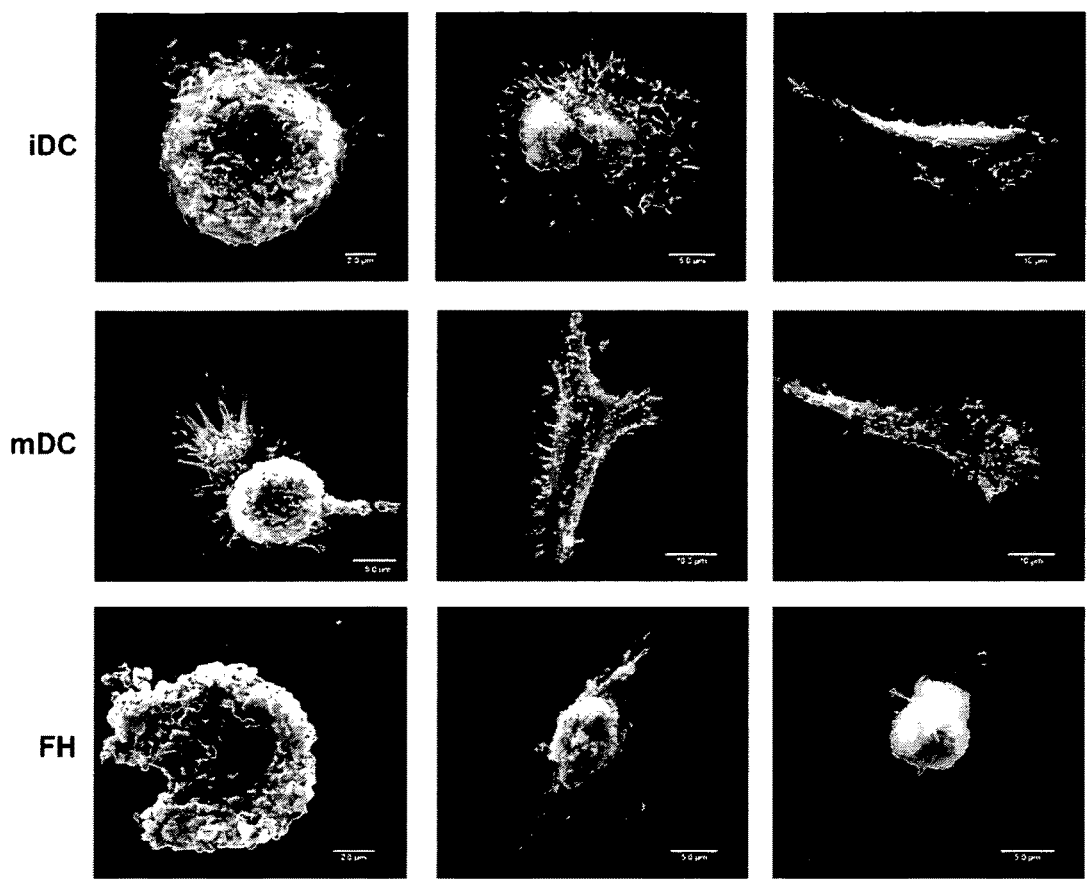

FIG. 14. Factor H modifies the morphology of human Mo-DCs

The surface morphology of Mo-DCs treated with Factor H (10 µg/ml) and matured with LPS was examined by SEM, and compared with those from both untreated, immature (iDC) and LPS-matured (mDC) DCs. Note the absence of long dendritic projections in Factor H-treated DCs, more closely resembling to the immature DC phenotype.

Figure 15:
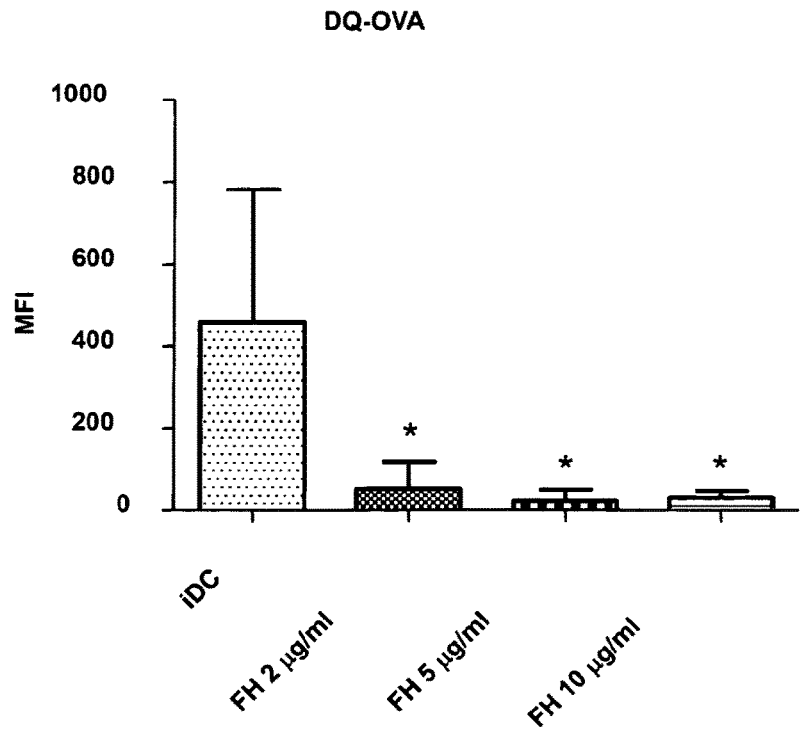

FIG. 15. Factor H reduces the endocytic potential of iDCs

Untreated, or Factor H-treated (2, 5, and 10 µg/ml) immature Mo-DCs were incubated with fluorescent DQ-OVA at 37° C. for 15 min in the dark, and examined by flow cytometry to measure specific uptake. The phagocytosis level of Factor H-treated iDCs (iDC) was significantly lower than untreated iDCs (*, p<0.05). The results are presented as mean MFI+/−SD from 3 independent experiments.

Figure 16:
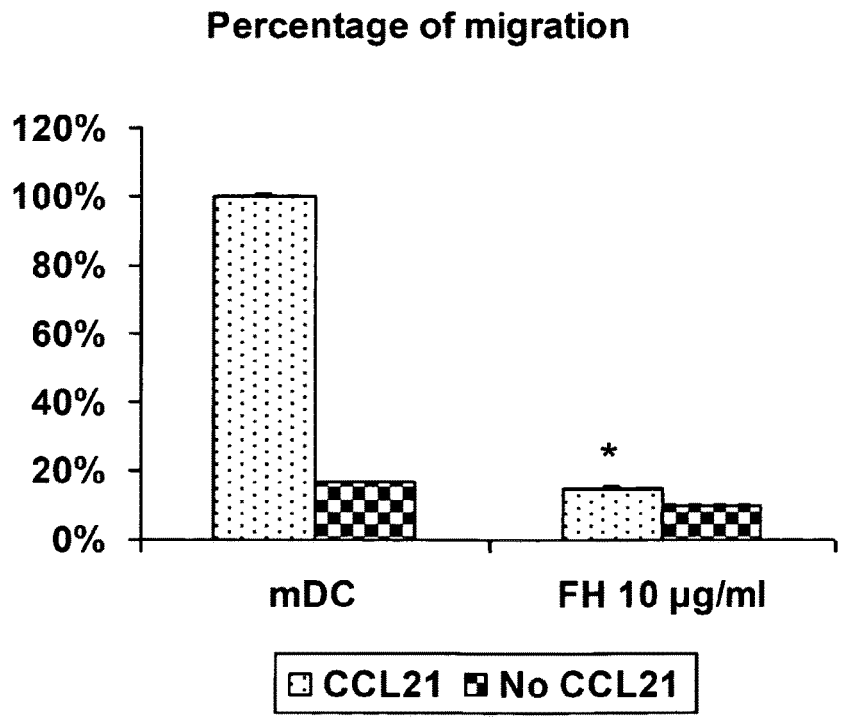

FIG. 16. Factor H alters the chemotaxis of human Mo-DCs

Migration of LPS-matured, untreated and Factor H-treated Mo-DCs towards the chemokine CCL21 was assessed in transwell assays. Shown are the percentages of DCs migrated toward the lower CCL21-containing chamber after 2 h incubation, relative to the migration values from untreated DCs (mDC) (100%). Spontaneous migration of DCs towards a lower chamber without CCL21 was also assessed. Results are the mean +/−SD from 4 independent experiments performed in duplicate. (*, p<0.05 respect to mDC).

Figure 17:
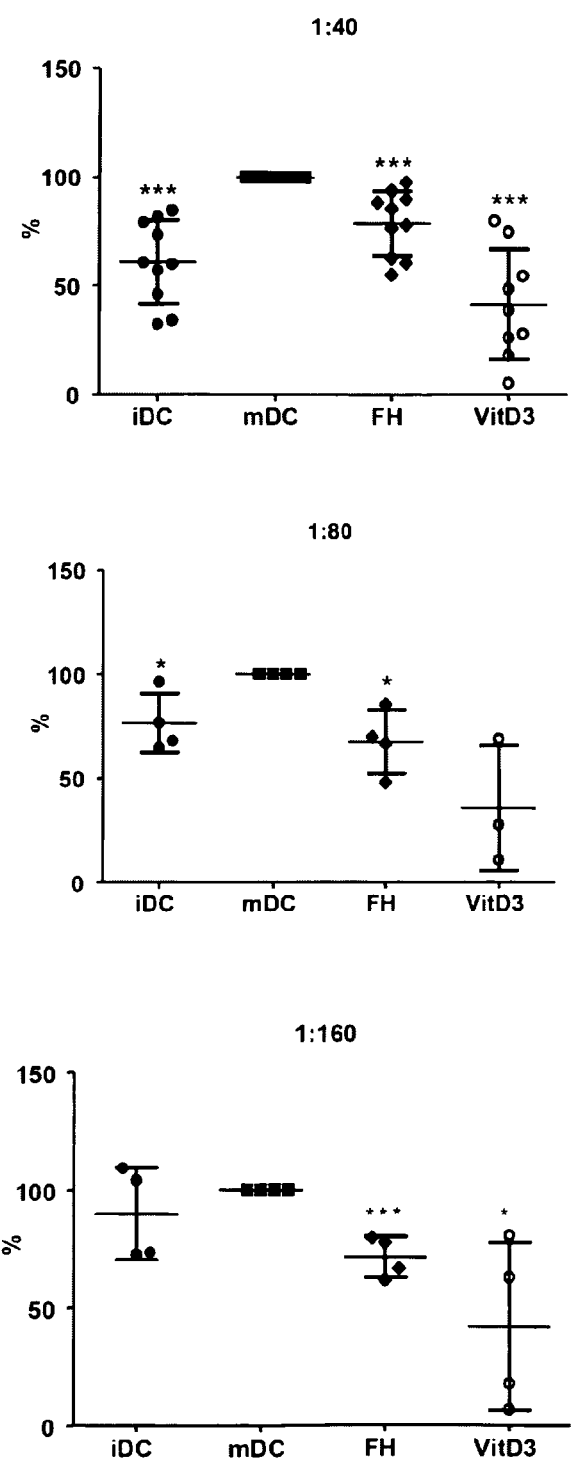

FIG. 17. Human Mo-DCs exposed to Factor H inhibit allogeneic T cell proliferation Untreated (mDC), Factor H-treated, at 5 µg/ml, or VitD3-treated (calcitriol, Calcigex®, Abbott Laboratories, S.A., at 2.4 µM), and LPS-matured Mo-DCs were cultured in triplicate with allogeneic, purified CD3' T cells ($10^5$/well) at 1:40 (n=8), 1:80 and 1:160 (both n=4) DC:T cell ratio for 5 days. [$^3$H] Thymidine (1 µCi/well) was added for the last 16 h of culture, and incorporation was measured by a β-plate counter (*, p<0.05; , p<0.01; *, p<0.001 respect to mDC). iDC, untreated, immature DCs.

Figure 18:
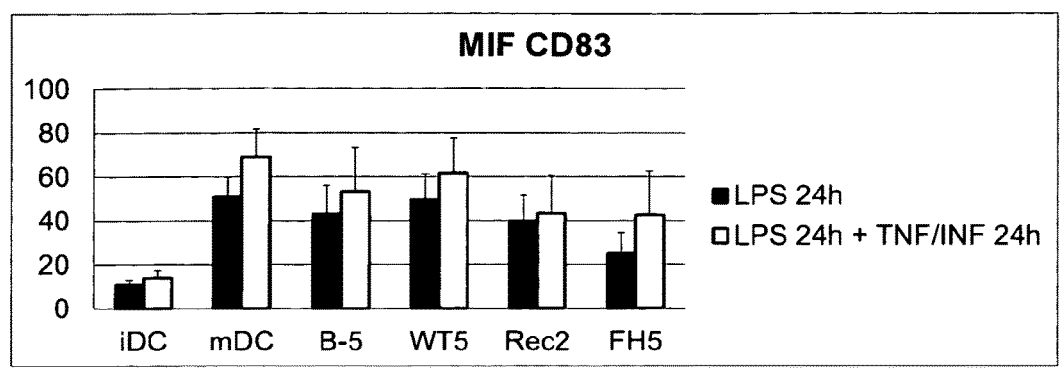
Figure 18:
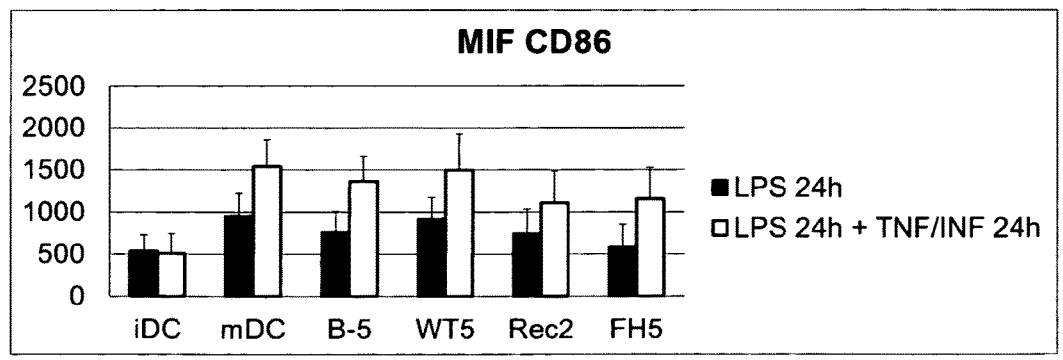

FIG. 18. C4BP(β−)- or FH-induced tolerogenic DCs exhibit a stable phenotype.

The stability of C4BP(β−)- or FH-treated and LPS-matured DCs was evaluated after further 24 h of induction with pro-inflammatory TNF-alpha (100 U/ml)+IFN-gamma (1000 U/ml) in complete medium without immunomodulatory agents (C4BP(β−) or FH). Median fluorescence intensities (MIF) of DC markers CD83 (A) and CD86 (B) were determined for all DC conditions (with or without TNF-alpha+IFN-gamma). iDC, immature DCs; mDC, untreated LPS-matured DCs; B-5, C4BP(β−)-treated (5 µg/ml) and LPS-matured DCs; WT5, C4BP(β+)-treated (5 µg/ml) and LPS-matured DCs; Rec2, recombinant C4BP(β−)-treated (2 µg/ml) and LPS-matured DCs; FH5, FH-treated (5 µg/ml) and LPS-matured DCs (n=6 per group).

Figure 19:
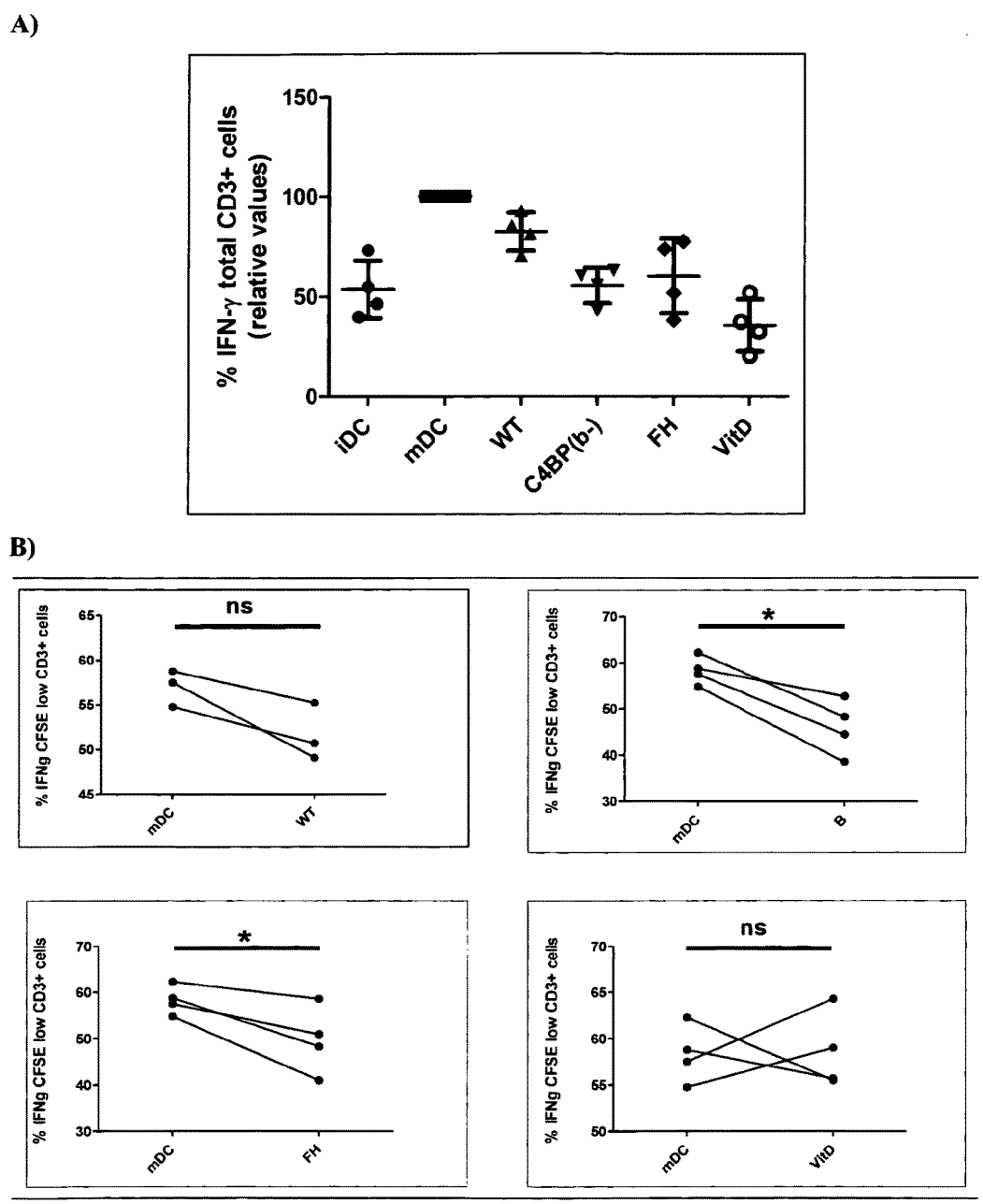

FIG. 19. Decreased production and secretion of IFN-gamma by T lymphocytes stimulated with C4BP(β−)- or FH-treated DCs.

Proliferating T lymphocytes were obtained from allostimulatory cultures. The production of IFN-gamma was measured by intracellular staining after re-stimulating the cells with PMA+ionomycin in the presence of brefeldin for 5 h. (A) Summary of the results of the total T cell intracellular IFN-gamma production from C4BP(β−)- or FH-treated, LPS-matured DC:T cultures relative to untreated, LPS-matured DC:T cultures (taken as 100% production). (B) Percentages of IFN-gamma producing T cells that responded to allostimulation ($CSFE^{low}CD3+$ cells). Each symbol represents an individual sample. iDC, immature DCs; mDC, untreated, LPS-matured DCs; C4BP(β−) or B, C4BP(β−)-treated (5 µg/ml) and LPS-matured DCs; WT, C4BP(β+)-treated (5 µg/ml) and LPS-matured DCs; FH, FH-treated (5 µg/ml) and LPS-matured DCs; VitD, VitD-treated and LPS-matured DCs. Significant differences are indicated (n=4 per group, except mDC/WT: n=3); * p<0.05; paired t-test).

Figure 20:
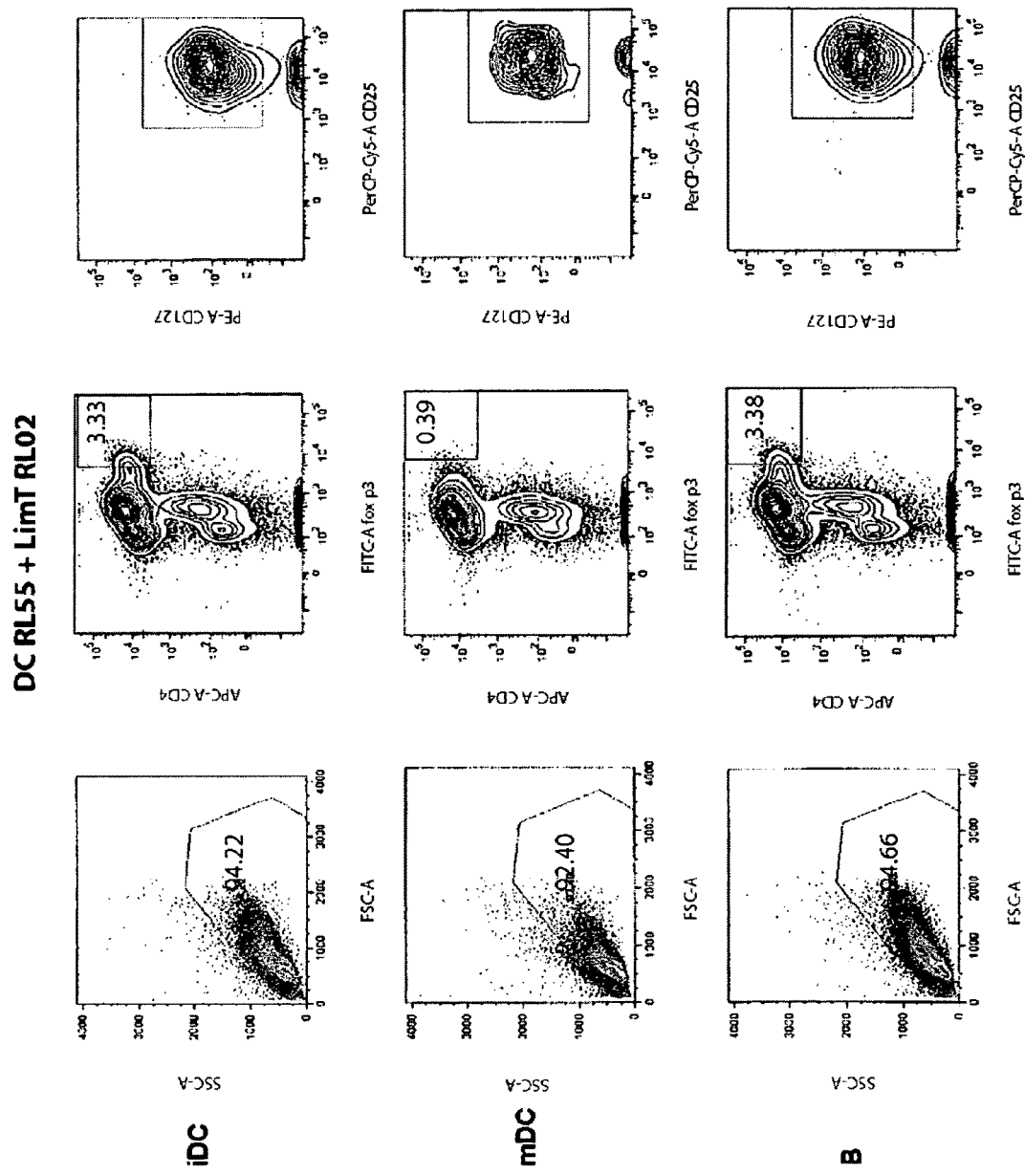
Figure 20:
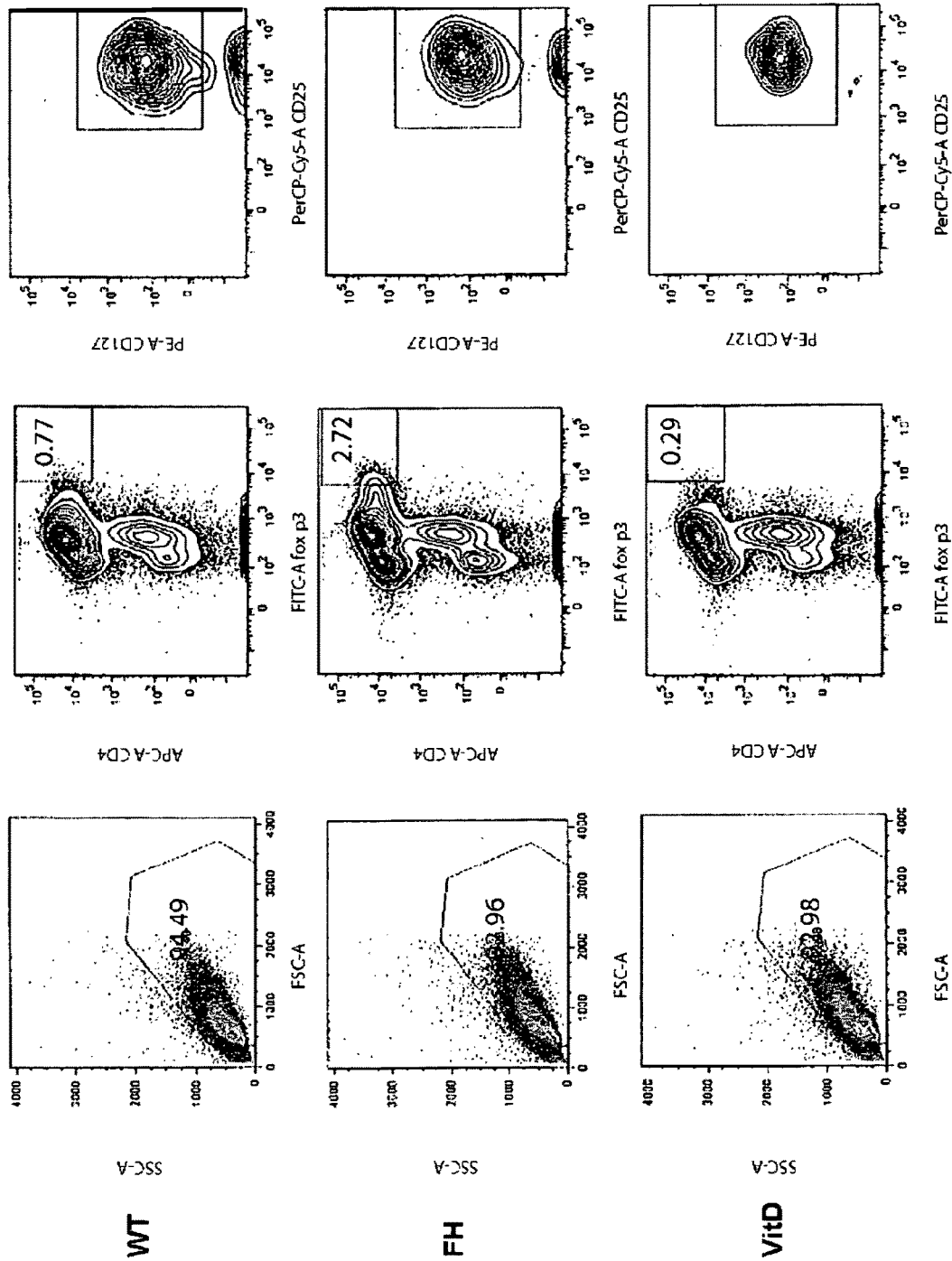

FIG. 20. C4BP(β−) or FH-treated DCs promote CD4+ $CD25^{hi}Cd127^{low}FoxP3+$ induction from blast T cells.

After 6 days of culture without re-stimulation and any supplemental cytokines, cell sizes were evaluated by FACS by plotting forward scatter (FSC) versus side scatter (SSC) parameters (left column). Phenotype of T cells as CD4+, FoxP3+ (middle column) and CD25+ with low or null CD127 expression (right column). One of 4 representative experiments is shown. iDC, immature DCs; mDC, untreated, LPS-matured DCs; B, C4BP(β−)-treated (5 µg/ml) and LPS-matured DCs; WT, C4BP(β+)-treated (5 µg/ml) and LPS-matured DCs; FH, FH-treated (5 µg/ml) and LPS-matured DCs; VitD, VitD-treated and LPS-matured DCs.

DETAILED DESCRIPTION OF THE INVENTION

Therapeutic Uses of C4BP Isoforms Lacking Beta Chain

The authors of the present invention have found that C4BP iso forms lacking the beta chain are capable of inhibiting the maturation of dendritic cells in the presence of maturation stimuli and of promoting the generation of dendritic cells which show features of tolerogenic dendritic cells. As shown in examples 1 to 6 of the present invention, C4BP iso forms lacking the beta chain are capable of down-regulate activation markers of human Mo-DCs and the release of inflammatory cytokines by LPS-matured human Mo-DCs. Moreover, C4BP isoforms lacking the beta chain modify the morphology of human Mo-DCs, decrease the chemotaxis of human Mo-DCs and allogeneic T cell proliferation in response to the exposure to dendritic cells.

In addition, the authors of the present invention have found that C4BP iso forms lacking the beta chain generate tolerogenic dendritic cells having a decreased T cell-stimulatory capability, and the ability not only to prevent Th1 differentiation under pro-inflammatory conditions, but also to generate regulatory T cells.

Thus, in a first aspect, the invention relates to a C4BP isoform lacking the beta chain for use in the prevention and/or treatment of an immunological disease.

In another embodiment, the invention relates to the use of a C4BP isoform lacking the beta chain for the manufacture of a medicament for the prevention and/or treatment of an immunological disease.

In another aspect, the invention relates to a method for the prevention and/or treatment of an immunological disease in a subject in need thereof comprising the administration to said subject of a C4BP iso form lacking the beta chain.

In another aspect, the invention relates to a method for increasing tolerogenic dendritic cell and/or regulatory T cell populations in a subject in need thereof comprising the administration to said subject of a C4BP isoform lacking the beta chain.

In another aspect, the invention relates to a C4BP isoform lacking the beta chain for use in increasing a tolerogenic dendritic cell and/or a regulatory T cell population.

The term "C4BP", as used herein, refers to a regulatory component of the classical pathway that is mainly synthesized by liver cells which acts as a cofactor for Factor I-dependent degradation of C3b and C4b and accelerates the decay of classical pathway C3/C5-convertases. C4BP circulates in the plasma as three isoforms, the proportion of which depends on the relative levels of C4BPα (70 kDa) and C4BPβ (45 kDa) chains. The major iso form of C4BP is composed of 7 identical α-chains and 1 β-chain ($\alpha_7\beta_1$), whereas upon inflammation a normally less abundant isoform is up-regulated that is exclusively composed of α-chains ($\alpha_7\beta_0$). Moreover, recombinant expression of the α-chains in eukaryotic cells results in oligomer comprising 6 α-chains ($\alpha_6\beta_0$). Thus, the C4BP isoforms which are useful in the method of the present invention include any iso form resulting from the association of a plurality of α-chains and which are devoid of β-chain.

The skilled person will understand that C4BP iso forms lacking a β chain may be formed exclusively by α-chains as they naturally occur in nature (e.g. human, mouse, rat, or bovine C4BP α-chain) as defined below or may contain one or more α-chain variants. For instance, the C4BP isoforms lacking β chain may contain at least one, at least two, at least three, at least four, at least five, at least six α-chain variants (in the case that the C4BP isoform is the $\alpha_6\beta_0$) or at least one, at least two, at least three, at least four, at least five, at least six or at least seven α-chain variants (in the case that the C4BP isoform is the $\alpha_7\beta_0$).

The term "C4BP α-chain", also known as PRP or proline-rich protein, as used herein, refers to the mature processed form of the human polypeptide defined under accession number P04003 in the NCBI database (release of Apr. 5, 2011) and which comprises amino acids 49 to 597. The term C4BP α-chain is also used to refer to orthologs of the human C4BP α-chain such as the mouse C4BP α-chain corresponding to the mature form of the polypeptide shown in the NCBI database under accession number P08607 (amino acids 57 to 469), the rat C4BP α-chain corresponding to the mature form of the polypeptide shown in the NCBI database under accession number Q63514 (amino acids 14 to 558), the bovine C4BP α-chain corresponding to the mature form of the polypeptide shown in the NCBI database under accession number Q28065 (amino acids 49 to 610).

The C4BP α-chain contains 8 complement control protein domains (CCP) which are 60 amino acid residues long with four cysteine residues disulfide bonded in a 1-3 2-4 arrangement, and a hydrophobic core built around an almost invariant tryptophan residue). The C-terminal extensions of both α- and β-chains contain 2 cysteine residues each and an amphipatic a helix region, which is required for intracellular polymerization of the molecule.

The term "C4BP α-chain" is also used herein to refer to any variant of the naturally-occurring C4BP α-chains defined above resulting from the modification, insertion or deletion of one or more amino acids and which substantially preserves the ability to form oligomers with other C4BP α-chain or variants thereof. Methods for determining whether a variant a is capable of forming oligomers are available to the skilled person and include, for instance, a method as described by Blom et al. (J. Biol. Chem. 2001, 276: 27136-27144) based on the analysis by polyacryamide gel electrophoresis under native conditions of a purified C4BP obtained by recombinant expression of the variant α-chain in eukaryotic cell (e.g. 293 cells) followed by affinity purification using an antibody specific for one of the CCP regions which has not been deleted.

C4BP α-chain variants for use according to the present invention include, without limitation:

Naturally occurring polymorphic variants (i.e., allelic variant) as well as recombinantly manipulated or engineered α-chain variants. Variant C4BP α-chains suitable for use according to the present invention include, without limitation, polypeptides having at least 99%, at least 98%, at least 97%, at least 96%, at least 95%, at least 94%, at least 93%, at least 92%, at least 91%, at least 90%, at least 85%, at least 80%, at least 75%, at least 70%, at least 65%, at least 60%, at least 55%, at least 50% identity with the naturally-occurring C4BP α-chain polypeptides as defined above and, in particular, with the naturally-occurring C4BP α-chain of human origin.

The percent identity of the amino acid sequence of a C4BP α-chain variant to the amino acid sequence set forth above can be readily determined by persons skilled in the art by sequence comparison. As used herein, two amino acid sequences have 100 percent amino acid sequence identity if the amino acid residues of the two amino acid sequences are the same when aligned for maximal correspondence. Sequence comparisons of polypeptides and polynucleotides (for example, the polynucleotides that encode the polypeptides described herein) can be performed using any method such as those that use computer algorithms well known to persons having ordinary skill in the art. Such algorithms include Align or the BLAST algorithm (see, e.g., Altschul, J. Mol. Biol. 219:555-565, 1991; Henikoff and Henikoff, Proc. Natl. Acad. Sci. USA 89:10915-10919, 1992), which are available at the NCBI website (see [online] Internet at ncbi.nlm.nih.gov/cgi-bin/BLAST). Default parameters may be used. In addition, standard software programs are available, such as those included in the LASERGENE bioinformatics computing suite (DNASTAR, Inc., Madison, Wis.); CLUSTALW program (Thompson et al., Nucleic Acids Res. 22:4673-80 (1991)); and "Gene-Doc" (Nicholas et al., EMBNEW News 4:14 (1991)). Other methods for comparing two amino acid sequences by determining optimal alignment are practiced by persons having skill in the art (see, for example, Peruski and Peruski, The Internet and the New Biology: Tools for Genomic and Molecular Research (ASM Press, Inc. 1997); Wu et al. (eds.), "Information Superhighway and Computer Databases of Nucleic Acids and Proteins," in Methods in Gene Biotechnology, pages 123-151 (CRC Press, Inc. 1997); and Bishop (ed.), Guide to Human Genome Computing, 2nd Ed. (Academic Press, Inc. 1998)).

Deletion mutants which lack at least one of the CCP regions provided that the CCP6 region is preserved (see example 7) such as, for, instance, mutants lacking the CCP1 domain, lacking the CCP2 domain, lacking the CCP3 domain, lacking the CCP4 domain, lacking the CCP5 domain, lacking the CCP7 domain and/or lacking the CCP8 domain.

Fusion proteins comprising a first region which comprises the C4BP α-chain and a second region which comprises a polypeptide which does not form part of the C4BP alpha chain. The fusion protein of the present invention may comprise in an amino terminal to carboxy terminal direction, (a) the region which comprises the CCP6 domain and (b) the region which comprises a polypeptide which does not form part of the C4BP alpha chain. Alternatively the fusion protein of the invention may comprise in an amino terminal to carboxy terminal direction, (a) the region which comprises a polypeptide which does not form part of the C4BP alpha chain and (b) the region which comprises the CCP6 domain. Examples of fusion proteins that improve pharmacokinetic properties include without limitation, fusions to human albumin, an immunoglobulin Fc region, Fc domains, poly Glu or poly Asp sequences, ferritin and transferrin. Additionally, fusion with conformationally disordered polypeptide sequences composed of the amino acids Pro, Ala, and Ser ('PASylation') or hydroxyethyl starch (HESylation®) provides a simple way to increase the hydrodynamic volume of the C-peptide. This additional extension adopts a bulky random structure, which significantly increases the size of the resulting fusion protein. In a preferred embodiment, the region which comprises a polypeptide which does not form part of the C4BP alpha chain is an immunoglobulin Fc region.

As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH 1 domain and a CH2 domain, 3) a CH1 domain and a CH3 domain, 4) a CH2 domain and a CH3 domain, or 5) a combination of two or more CH domains and an immunoglobulin hinge region. The immunoglobulin Fc region of the fusion protein of the present invention preferably comprises or consists of an Fc or a portion of an Fc of an immunoglobulin of isotype selected from IgG, IgM, IgA, IgD, IgE, further preferably, IgG1, IgG2, IgG3, IgG4, IgA1, IgA2, sIgA, more preferably IgG2 or IgG4, most preferably IgG2.

The term "immunological disease", as used herein, refers to any disease which is caused by an undesired activation of the immune system, including the innate or adaptative immune system as well as the humoral or cell branch of the immune system.

In a preferred embodiment, the immunological disease is selected from the group consisting of an immunoinflammatory disease, sepsis, autoimmune disease, transplant rejection, graft-versus-host disease and hypersensitivity diseases.

The term "immunoinflammatory disease", as used herein refers to inflammatory diseases and disorders in which immune cells and/or cytokines are involved in the pathophysiology of the disease or disorder. Examples of immunoinflammatory diseases include such conditions as rheumatoid arthritis, juvenile rheumatoid arthritis, osteoarthritis, acute respiratory distress syndrome and asthma. The term immunoinflammatory disease includes both acute and chronic inflammatory disorders. The term "acute inflammatory disorder" is intended to include disorders, and episodes of disorders, characterized by rapid onset of symptoms associated with an inflammatory response and relatively short duration of symptoms, whereas a "chronic inflammatory disorder" is intended to include disorders characterized by the continued presence of symptoms associated with an inflammatory response and ongoing duration of symptoms. Immunoinflammatory diseases which can be treated with the methods according to the present invention include, without limitation, cardiovascular diseases such as infarct or stroke, atherosclerosis, pulmonary fibrosis, rheumatoid arthritis, juvenile rheumatoid arthritis, osteoarthritis, acute respiratory distress syndrome, asthma, and cancer. Also comprised within the immunoinflammatory diseases that can be treated according to the present invention include diseases which appear during pregnancy such as pre-eclampsia and eclampsia. Pre-eclampsia is a pregnancy-related disease characterised by hypertension, proteinuria and oedema. Pre-eclampsia is understood and shall be defined herein to encompass and reside within a spectrum of pre-eclampsia disorders, including placental insufficiency, intrauterine growth retardation, early miscarriage, preterm birth, intrauterine death and eclampsia.

The term "sepsis", as used herein, refers to a systemic host response to microorganisms in previously sterile tissues characterized by end-organ dysfunction away from the primary site of infection. To qualify as sepsis, there must be an infection suspected or proven (by culture, stain, or polymerase chain reaction (PCR)), or a clinical syndrome pathognomonic for infection. Specific evidence for infection includes WBCs in normally sterile fluid (such as urine or cerebrospinal fluid (CSF), evidence of a perforated viscus (free air on abdominal x-ray or CT scan, signs of acute peritonitis), abnormal chest x-ray (CXR) consistent with pneumonia (with focal opacification), or petechiae, purpura, or purpura fulminans. The more critical subsets of sepsis are severe sepsis (sepsis with acute organ dysfunction) and septic shock (sepsis with refractory arterial hypotension). As an alternative, when two or more of the systemic inflammatory response syndrome criteria are met without evidence of infection, patients may be diagnosed simply with "SIRS." Patients with SIRS and acute organ dysfunction may be termed "severe SIRS." Patients are defined as having "severe sepsis" if they have sepsis plus signs of systemic hypoperfusion: either end-organ dysfunction or serum lactate greater than 4 mmol/dL. Other signs include oliguria and altered mental status. Patients are defined as having septic shock if they have sepsis plus hypotension after aggressive fluid resuscitation (typically upwards of 6 liters or 40 ml/kg of crystalloid). Examples of end-organ dysfunction include acute lung injury or acute respiratory distress syndrome, encephalopathy, or dysfunction affecting liver (disruption of protein synthetic function and metabolic functions), kidney (oliguria and anuria, electrolyte abnormalities, volume overload), and heart (systolic and diastolic heart failure).

Suitable sepsis conditions that can be treated with the compositions according to the present invention include, without limitation, severe sepsis, septic shock. In one embodiment, the condition associated with sepsis syndrome is selected from the group consisting of an organ dysfunction, preferably a kidney dysfunction or a liver dysfunction, a multiple organ dysfunction syndrome (MODS), an acute respiratory distress syndrome (ARDS), and disseminated intravascular coagulation (DIC).

Sepsis may be induced by a bacterium or more than one bacterium selected from the group consisting of Gram-negative bacteria and Gram-positive bacteria. Preferably, the Gram-negative bacterium is selected from the group consisting of *Escherichia coli, Klebsiella* species, *Serratia* species, *Enterobacter* species, *Proteus* species, *Pseudomonas aeruginosa, Haemophilus influenzae, Neisseria* species, and *Listeria* species.

Alternatively, the Gram-positive bacterium is selected from the group consisting of *Staphylococcus aureus, Streptococcus pneumoniae*, coagulase-negative Staphylococci, *Enterococcus* species, *Streptococcus pyogenes*, and *Streptococcus viridans*. In one embodiment, the sepsis syndrome is induced by LPS. In yet another embodiment, the sepsis is induced by a microorganism or more than one microorganism selected from the group consisting of anaerobic bacteria, fungi, rickettsiae, chlamydiae, mycoplasma, spirochetes, and viruses.

The term "autoimmune disease", "disease associated with immune dysfunction/dysregulation" or "immune inflammatory disease" is used throughout the specification to refer to a pathogenic condition in which the patients immune system results in disease from a self antigen (autoimmunity) or a foreign antigen (immune dysfunction/dysregulation or immune inflammatory disease). Autoimmunity is present in everyone to some extent. It is usually harmless and probably a universal phenomenon of vertebrate life. However, autoimmunity can be the cause of a broad spectrum of human illnesses, known as autoimmune diseases. This concept of autoimmunity as the cause of human illness is relatively new, and it was not accepted into the mainstream of medical thinking until the 1950s and 1960s. Autoimmune diseases are, thus, defined when the progression from benign autoimmunity to pathogenic autoimmunity occurs. This progression is determined by both genetic influences and environmental triggers. The concept of autoimmunity as the actual cause of human illness (rather than a consequence or harmless accompaniment) can be used to establish criteria that define a disease as an autoimmune disease. Autoimmune diseases or diseases which are characterized as involving immune dysfunction or disregulation (immune inflammatory disease), which may be treated by the present invention include systemic lupus erythematosis (SLE), diabetes mellitus (type I), asthma, ulcerative cholitis, Grave's disease, arthritis, including rheumatoid arthritis and osteoarthritis, pernicious anemia, and multiple sclerosis, among numerous others. Numerous autoimmune diseases may be treated using the method of the present invention including autoimmune blood diseases, including pernicious anemia, autoimmune hemolytic anemia, aplastic anemia, idiopathic thrombocytopenic purpura, ankylosing spondilitis; autoimmune diseases of the musculature including polymyositis and dermatomyositis, autoimmune diseases of the ear including autoimmune hearing loss and Meniere's syndrome, autoimmune eye diseases, including Mooren's disease, Reiter's syndrome and Vogt-Koyanagi-Harada disease, autoimmune diseases of the kidney including glomerulonephritis and IgA nephropathy; diabetes mellitus (type I); autoimmune skin diseases including pemphigus (autoimmune bullous diseases), such as pemphigus vulgaris, pemphigus foliaceus, pemphigus erythematosus, bullous pemphigoid, vitiligo, epidermolysis bullosa acquisita, psoriasis and alopecia greata; cardiovascular autoimmune diseases, including autoimmune myocarditis, vasculitis including Churg-Strauss syndrome, giant cells arteritis, Kawasaki's disease, polyarteritis nodosa, Takayasu's arteritis and Wegener's granulomatosis; endocrine autoimmune diseases, including Addison's disease, autoimmune hypoparathyroidism, autoimmune hypophysitis, autoimmune oophoritis, autoimmune orchitis, Grave's Disease, Hashimoto's thyroiditis, polyglandular autoimmune syndrome type 1 (PAS-I) polyglandular autoimmune syndrome type 2 (PAS-2), and polyglandular autoimmune syndrome type 3 (PAS-3); autoimmune gastroenteric diseases including autoimmune hepatitis, primary biliary cirrhosis, inflammatory bowel disease, celiac disease, Crohn's disease; autoimmune nervous diseases, including multiple sclerosis, myasthenia gravis, Guillan-Barre syndrome and chronic inflammatory demyelinating neuropathy; and systemic autoimmune diseases including systemic lupus erythematosus, antiphospholid syndrome, autoimmune lymphoproliferative disease, autoimmune polyendocrinopathy, Bechet's disease, Goodpasture's disease, arthritis, including rheumatoid arthritis, osteoarthritis and septic arthritis, sarcoidosis, scleroderma and Sjogren's syndrome and psoriasis among others.

The expression "transplant rejection", as used herein, refers to an immune condition in which a transplanted cell, tissue, or organ is not accepted by the body of the transplant recipient. The expression transplant rejection encompasses both acute and chronic transplant rejection.

"Acute rejection or AR" is the rejection by the immune system of a tissue transplant recipient when the transplanted tissue is immunologically foreign. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery.

"Chronic transplant rejection or CR" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs.

As is known in the transplantation field, the transplant organ, tissue or cell(s) may be allogeneic or xenogeneic, such that the grafts may be allografts or xenografts. A feature of the graft tolerant phenotype detected or identified by the subject methods is that it is a phenotype which occurs without immunosuppressive therapy, i.e., it is present in a host that is not undergoing immunosuppressive therapy such that immunosuppressive agents are not being administered to the host. The transplant graft maybe any solid organ and skin transplant. Examples of organ transplants that can be analyzed by the methods described herein include but are not limited to kidney transplant, pancreas transplant, liver transplant, heart transplant, lung transplant, intestine transplant, pancreas after kidney transplant, and simultaneous pancreas-kidney transplant.

The methods according to the present invention are also suitable for the prevention and/or treatment of delayed Graft Function (DGF) due to ischemia-reperfusion injury. The term "delayed graft function", as used herein, refers to a form of acute renal failure resulting in post-transplantation oliguria, increased allograft immunogenicity and risk of acute rejection episodes, and decreased long-term survival. DGF may be caused by different factors related to the donor and prerenal, renal, or postrenal transplant factors related to the recipient. However, a major cause of delayed graft function is ischaemia and reinstitution of blood flow in ischaemically damaged kidneys after hypothermic preservation.

The term "graft-versus-host disease" or GVHD, as used herein, refers to a condition that occurs when T cells present in donor tissue attack the host, or recipient, of the grafted cells or tissue. Any type of GVHD can be treated by the therapeutic agents of the present invention, including acute GVHD and chronic GVHD.

The term "hypersensitivity disease" refers to a condition in which the subject has an abnormal sensitivity to an innocuous agent, known as allergen. Hypersensitivity disease can be categorized into four types, Type I, Type II, Type III and Type IV. Type I is described as atopic or anaphylactic which results from a release of mediators from IgE-sensitized basophils and mast cells. Type II is described as cytotoxic which involves complement-fixing antibody with cell lysis or antibody-dependent cellular cytotoxocity. Type III is described as immune-complex-mediated which is associated with soluble antigen-antibody complexes. Type IV is described as cell-mediated or delayed hypersensitivity which results from a release of lymphokines by sensitized T lymphocytes after contact with an antigen.

The prevention and/or treatment of an immunological disease is achieved through the increase of tolerogenic dendritic cell and/or regulatory T cell populations.

The expression "increasing tolerogenic dendritic cell population" is understood to mean that the administration of a C4BP isoform lacking the beta chain produces an increase in the number of tolerogenic dendritic cells with respect to an untreated subject. The tolerogenic dendritic cell population is increased by 10%, 20%, 30%, 40%, 50%, 60%, 70%, 80%, 90%, 95%, 97%, 98%, 99%, or 100% in comparison with an untreated subject. The capacity of the C4BP iso form lacking the beta chain of increasing a tolerogenic dendritic cell population can be determined, for instance, as described in examples 1 to 5.

The expression "increasing regulatory T cell population", as used herein, means that the C4BP isoform lacking the beta chain produces an increase in the number of regulatory T cells with respect to an untreated subject. The regulatory T cell population is increased by 10%, 20%, 30%, 40%, 50%, 60%, 70%, 80%, 90%, 95%, 97%, 98%, 99%, or 100% in comparison with an untreated subject. The capacity of the C4BP iso form lacking the beta chain of increasing regulatory T cell population can be determined, for instance, as described in example 17.

Immunologically Active C4BP α-Chain Variants and Peptides

The authors of the present invention have identified that the isolated CCP6 domain of the C4BP alpha chain is a necessary region for inhibiting the maturation of dendritic cells and that certain polypeptides derived from the CCP6 domain of the C4BP alpha chain are capable of recapitulating the effect of the C4BP isoforms lacking the beta chain in the inhibition of the maturation of dendritic cells and in promoting the acquisition by said cells of the tolerogenic phenotype.

Thus, in another aspect, the invention relates to a polypeptide comprising the CCP6 domain of the C4BP alpha chain, a functionally equivalent variant thereof, wherein said polypeptide is not the full-length C4BP alpha. The term "CCP domain", as used herein, refers to one of the complement control domain found in the C4BP alpha chain. The CCP are 60 amino acid residues long comprising four cysteine residues disulfide bonded in a 1-3 2-4 arrangement and a hydrophobic core built around an almost invariant tryptophan residue. CCP6 corresponds to the region found between amino acids 363 and 424 with respect to the human C4BP alpha chain defined in the sequence provided in the NCBI database under accession number P04003 (SEQ ID NO:1) and which corresponds to the sequence:

(SEQ ID NO: 1)
LCCPEPKLNN GEITQHRKCR PANHCVYFYG DEISFSCHET

CRFSAICQGD GTWSPRTPSC GD

Preferably, the polypeptide comprising the CCP6 domain does not comprise a region of a protein different from C4BP. In another embodiment, the polypeptide comprising the CCP6 domain of the C4BP alpha chain lacks at least the CCP1 domain, at least the CCP2 domain, at least the CCP3 domain, at least the CCP4 domain, at least the CCP5 domain, at least the CCP7 domain and/or at least the CCP8 domain of the C4BP alpha chain. In a still more preferred embodiment, the polypeptide comprising the CCP6 domain of the C4BP alpha chain does not contain any of the other CCP domains found in the C4BP alpha chain. Suitable polypeptides comprising the CCP6 domain of the C4BP alpha chain for use according to the present invention include, without limitation:
- a polypeptide comprising the CCP5, CCP6 and CCP7 domains of the C4BP alpha chain,
- a polypeptide comprising the CCP5, CCP6 and CCP7 domains of the C4BP alpha chain but lacking the one or more of any of the other CCP domains found in the C4BP alpha chain and, in particular, lacking CCP8 and
- a polypeptide comprising the CCP5, CCP6 and CCP7 domains of the C4BP alpha chain and wherein said polypeptide does not comprise a region of a protein different from C4BP.

The term "functionally equivalent variant", when referred to the polypeptide comprising the CCP6 domain of the C4BP alpha chain refers to any polypeptide having a sequence which derives from said polypeptide by insertion, deletion or substitution of one or more amino acids and which substantially preserves the functional activity of the original polypeptide. Suitable variants encompassed within the present invention include those polypeptides comprising a variant of the CCP6 domain showing at least 99%, at least 98%, at least 97%, at least 96%, at least 95%, at least 94%, at least 93%, at least 92%, at least 92%, at least 91%, at least 90%, at least 85%, at least 80%, at least 75%, at least 70%, at least 65%, at least 60% or less identity with the human CCP6 domain. Suitable methods for determining the identity of two polypeptides have been defined above in detail. In a preferred embodiment, the variant contains one or more of the cysteine residues substituted by serine. The expression "substantially preserves the functional activity of the original polypeptide", as used herein, refers to polypeptides which are capable of inhibiting the maturation of dendritic cells as determined, e.g, as shown in examples 1 to 5 of the present invention. Thus, a polypeptide is considered as a functionally equivalent to the C4BP isoform lacking β chain if it shows at least 100%, at least 95%, at least 90%, at least 85%, at least 80%, at least 75%, at least 70%, at least 65%, at least 60% or at least 50% of the activity of the C4BP isoform lacking β, in particular, the $\alpha_7\alpha_0$ or the $\alpha_6\beta_0$ isoforms.

For example, the functionally equivalent variant of the polypeptide comprising the CCP6 domain of the C4BP alpha chain may be modified in order to modulate affinity for the receptor, modulate circulating half-life, modulate therapeutic half-life, modulate stability of the polypeptide, modulate cleavage by proteases, modulate dose, modulate release or bio-availability, facilitate purification, or improve or alter a particular route of administration. Similarly, the variants of the polypeptide comprising the CCP6 domain of the C4BP alpha chain may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

In another embodiment, the functionally equivalent variant of the polypeptide comprising the CCP6 domain of the C4BP alpha chain is a fusion protein comprising a first region which comprises the CCP6 domain and a second region which comprises a polypeptide which does not form part of the C4BP alpha chain. The fusion protein of the present invention may comprise in an amino terminal to carboxy terminal direction, (a) the region which comprises the CCP6 domain and (b) the region which comprises a polypeptide which does not form part of the C4BP alpha chain. Alternatively the fusion protein of the invention may comprise in an amino terminal to carboxy terminal direction, (a) the region which comprises a polypeptide which does not form part of the C4BP alpha chain and (b) the region which comprises the CCP6 domain. Preferably, the polypeptide forming part of the fusion protein and which comprises the CCP6 domain lacks at least the CCP1 domain, at least the CCP2 domain, at least the CCP3 domain, at least the CCP4 domain, at least the CCP5 domain, at least the CCP7 domain and/or at least the CCP8 domain of the C4BP alpha chain. In a still more preferred embodiment, the polypeptide comprising the CCP6 domain of the C4BP alpha chain does not contain any of the other CCP domains found in the C4BP alpha chain. Suitable polypeptides comprising the CCP6 domain of the C4BP alpha chain for use in the fusion protein according to the present invention include, without limitation:
- a polypeptide comprising the CCP5, CCP6 and CCP7 domains of the C4BP alpha chain,
- a polypeptide comprising the CCP5, CCP6 and CCP7 domains of the C4BP alpha chain but lacking the one or more of any of the other CCP domains found in the C4BP alpha chain and, in particular, lacking CCP8 and In a preferred embodiment, the polypeptide of the invention does not comprise a region of a protein different from C4BP. For example, the polypeptide of the invention cannot be a fusion protein comprising a region which forms part of a different protein from C4BP.

The authors have discovered that fragments of the CCP6 domain of the C4BP alpha chain wherein one or more of the cysteine residues are substituted by serine substantially preserve the functional activity of the original polypeptide. Specifically, the authors of the invention have synthesized four peptides of SEQ ID NO: 2, 3, 4 and 5.

In yet another aspect, the invention relates to a peptide having the sequence selected from the group consisting of SEQ ID NO: 2, 3, 4 and 5 or a functionally equivalent variant thereof (see Table I).

TABLE I

Peptides derived from CCP6 domain

| Peptide | Sequence | SEQ ID NO: |
|---|---|---|
| PS6-01 | LSSPEPKL NNGEITQHRK SRPANHSVYF YG | 2 |
| PS6-02 | HRK SRPANHSVYF YGDEISFSSH ETSRFSA | 3 |
| PS6-03 | EISFSSH ETSRFSAISQ GDGTWSPRTP SSG | 4 |
| PS6-04 | ITQHRK SRPANHSV | 5 |

In a preferred embodiment the peptide is SEQ ID NO: 5.

The term "peptide", as used herein, relates to a linear chain of around 2 to 40 amino acids joined together with peptide bonds.

Functionally equivalent variants of the peptides of the invention include, without limitation, peptides modified by insertion, deletion or substitution of one of more amino acids of the peptides mentioned above as well as peptidomimetics thereof which maintain substantially the activity of peptide. Methods adequate for determining whether a given polypeptide or peptide can be considered as a functionally equivalent variant of the isolated CCP6 polypeptide (SEQ ID NO: 1) or of the polypeptides of SEQ ID NO:2-5 include, e.g. the assays provided in example 8 of the present invention wherein a peptide is considered as a variant of the C4BP isoform lacking β chains if it shows an ability in generating tolerogenic dendritic cells when added to monocyte cells during the differentiation stage to immature dendritic cells and/or when added to immature dendritic cells during their maturation stage to mature dendritic cells. The ability of the variant to promote the generation of tolerogenic dendritic cells can be determined, e.g. by measuring the expression levels in the dendritic cells of maturation markers such as CD83, CD14 and/or CD1a of dendritic cells which have been matured in the presence of the variant (examples 1 and 2 of the present invention). Thus, a peptide can be considered as a functionally equivalent to the C4BP iso form lacking 0 chain if it shows at least 100%, at least 95%, at least 90%, at least 85%, at least 80%, at least 75%, at least 70%, at least 65%, at least 60% or at least 50% of the activity of the C4BP isoform lacking β, in particular, the α7β0 or the α6β0.

Functionally equivalent variants of the isolated CCP6 polypeptide (SEQ ID NO: 1) or of the polypeptides of SEQ ID NO: 2-5 suitable for use in the present invention include, without limitation:

- Peptides resulting from the derivatization of any of the above peptides including acylated, amidated, esterified derivatives and the like.
- Peptides resulting from modification of any of the above peptides by substitutions (e.g., conservative amino acid substitutions) and/or insertions (e.g., small, single amino acid insertions, or insertions encompassing 2, 3, 4, 5, 10, 15, 20, or more contiguous amino acids) and/or deletions (e.g., small, single amino acid deletions, or deletions encompassing 2, 3, 4, 5, 10, 15, 20, or more contiguous amino acids). Thus, in certain embodiments, a variant of a native peptide sequence is one that differs from a naturally-occurring sequence by (i) one or more (e.g., 2, 3, 4, 5, 6, or more) conservative amino acid substitutions, (ii) deletion of 1 or more (e.g., 2, 3, 4, 5, 6, or more) amino acids, or (iii) a combination thereof. Deleted or inserted amino acids can be contiguous or non-contiguous.
- In making such changes, the hydropathic index of amino acids is considered since it is known that certain amino acids may be substituted for other amino acids having a similar hydropathic index or score and result in a polypeptide with similar biological activity. For example, the relative hydropathic character of an amino acid residue affects the secondary and tertiary structure of the resultant polypeptide, which in turn defines the interaction of the polypeptide with other molecules, such as enzymes, substrates, receptors, antibodies, antigens, and the like. As outlined above, amino acid substitutions are generally based on the relative similarity of the amino acid side-chain substituents, for example, their hydrophobicity, hydrophilicity, charge, size, and the like. Exemplary substitutions which take various of the foregoing characteristics into consideration are well known to those of skill in the art and are set forth below in Table 2.

TABLE 2

Amino acid substitutions
Amino acid substitutions

| Original residue | Exemplary Residue Substitution |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Leu; Tyr |
| Ser | Thr |
| Thr | Ser |
| Trp | Tyr |
| Tyr | Trp |
| Val | Ile; Leu |

- In a preferred embodiment, the peptides are modified by replacing one or more of the serine residues by cysteine.
- Peptides having any of the above sequences but modified to include any of a variety of known chemical groups or molecules. Such modifications include, but are not limited to, glycosylation, acetylation, acylation, ADP-ribosylation, amidation, covalent attachment to polyethylene glycol (e.g., PEGylation), covalent attachment of flavin, covalent attachment of a heme moiety, covalent attachment of a nucleotide or nucleotide derivative, covalent attachment of a lipid or lipid derivative, covalent attachment of phosphatidylnositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, acylation, amidation, iodination, methylation, myristoylation. oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included.
- Peptidomimetics of the above peptides. A "peptide mimetic" or "peptidomimetic" refers to various types or classes of molecules, as long as the resulting molecule mimics or resembles a desired polypeptide secondary (or localized tertiary) structural element. For example, a peptide mimetic is an oligomer that mimics peptide secondary structure through use of amide bond isosteres and/or modification of the native peptide backbone, including chain extension or heteroatom incorporation; examples of which include azapeptides, oligocarbamates, oligoureas, beta-peptides, gamma-peptides, oligo(phenylene ethynylene)s, vinylogous sulfonopeptides, poly-N-substituted glycines (peptoids) and the like. Methods for designing and synthesizing peptide mimetics are well known to one of skill in the art. In certain embodiments, it is contemplated that a peptide mimetic is used to overcome protease sensitivity, stabilize secondary structure and/or improve bioavailability relative to a naturally occurring CCP6 peptide analogues. In certain embodiments, a peptide mimetic of the invention is a reverse turn mimetic, e.g., a alpha-turn mimetic, a monocyclic beta-turn mimetic, a bicyclic beta-turn mimetic, a gamma-turn mimetic or a monocyclic gamma-turn mimetic.

Polynucleotides, Vectors and Host Cells of the Invention

The invention provides as well polynucleotides encoding the polypeptides of the invention. Thus, in another aspect, the invention relates to a polynucleotide encoding a polypeptide comprising the CCP6 domain of the C4BP alpha chain or a functionally equivalent variant thereof, wherein said polypeptide is not the full-length C4BP alpha chain and wherein said polypeptide does not comprise a region of a protein different from C4BP.

The invention also provides a polynucleotide encoding a peptide having the sequence selected from the group consisting of SEQ ID NO:2, 3, 4 and 5 or a functionally equivalent variant thereof.

The terms "polynucleotide", "nucleic acid" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules. As used herein, mRNA refers to an RNA that can be translated in a cell.

The polynucleotides of the invention may further comprise a single promoter region regulating the transcription of the region encoding the polypeptides of the invention provided that said promoters are compatible with the cells in which the polypeptides are to be expressed. The polynucleotides encoding for the polypeptides of the invention can be found isolated as such or forming part of vectors allowing the propagation of said polynucleotides in suitable host cells. Vectors suitable for the insertion of said polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells, including baculovirus suitable for transfecting insect cells using any commercially available baculovirus system. The vectors for eukaryotic cells include preferably viral vectors (adenoviruses, viruses associated to adenoviruses, retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6/V5-His, pVAX1, pZeoSV2, pCI, pSVL and PKSV-10, pBPV-1, pML2d and pTDT1.

The vectors may also comprise a reporter or marker gene which allows identifying those cells that have been incorporated the vector after having been put in contact with it. Useful reporter genes in the context of the present invention include lacZ, luciferase, thymidine kinase, GFP and the like. Useful marker genes in the context of this invention include, for example, the neomycin resistance gene, conferring resistance to the aminoglycoside G418; the hygromycin phosphotransferase gene, conferring resistance to hygromycin; the ODC gene, conferring resistance to the inhibitor of the ornithine decarboxylase (2-(difluoromethyl)-DL-ornithine (DFMO); the dihydrofo late reductase gene, conferring resistance to methotrexate; the puromycin-N-acetyl transferase gene, conferring resistance to puromycin; the ble gene, conferring resistance to zeocin; the adenosine deaminase gene, conferring resistance to 9-beta-D-xylofuranose adenine; the cytosine deaminase gene, allowing the cells to grow in the presence of N-(phosphonacetyl)-L-aspartate; thymidine kinase, allowing the cells to grow in the presence of aminopterin; the xanthine-guanine phosphoribosyltransferase gene, allowing the cells to grow in the presence of xanthine and the absence of guanine; the trpB gene of $E.\ coli$, allowing the cells to grow in the presence of indol instead of tryptophan; the hisD gene of $E.\ coli$, allowing the cells to use histidinol instead of histidine. The selection gene is incorporated into a plasmid that can additionally include a promoter suitable for the expression of said gene in eukaryotic cells (for example, the CMV or SV40 promoters), an optimized translation initiation site (for example, a site following the so-called Kozak's rules or an IRES), a polyadenylation site such as, for example, the SV40 polyadenylation or phosphoglycerate kinase site, introns such as, for example, the beta-globulin gene intron. Alternatively, it is possible to use a combination of both the reporter gene and the marker gene simultaneously in the same vector. Vectors that contain both a promoter and a cloning site into which a polynucleotide according to the invention can be operatively linked are also provided in the present invention. Such vectors are capable of transcribing RNA in vitro or in vivo. In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Gene delivery vehicles also include several non-viral vectors, including DNA/liposome complexes, and targeted viral protein-DNA complexes. Liposomes that also comprise a targeting antibody or fragment thereof can be used in the methods of this invention. To enhance delivery to a cell, nucleic acids or proteins of this invention can be conjugated to antibodies or binding fragments thereof which bind cell surface antigens.

Methods for the Generation of a Population of Tolerogenic Dendritic Cells Obtained Using C4BP Isoforms Lacking the β Chain The authors of the present invention have observed that dendritic cells contacted with either a C4BP isoform lacking the beta chain, with a polypeptide comprising the isolated CCP6 domain of the C4BP α chain, with a peptide as defined in SEQ ID NO:2 to 5 or with the functionally equivalent variants thereof, with a polynucleotide encoding any of said polypeptides, with a vector comprising said polynucleotide show a tolerogenic phenotype, i.e.

Thus, in another aspect, the invention relates to a method for the generation of a population of tolerogenic dendritic cells comprising the steps of
(i) incubating a population of dendritic cell precursors under conditions adequate for the formation of a population of immature dendritic cells and
(ii) incubating the population of immature dendritic cells obtained in step (i) under conditions adequate for the formation of mature dendrite cells wherein steps (i) and/or (ii) are carried out in the presence of a composition of matter selected from the group consisting of:
(a) A C4BP iso form lacking the beta chain,
(b) a polypeptide of the invention,
(c) a peptide of the invention,
(d) a polynucleotide of the invention and
(e) a vector of the invention.

The term "dendritic cell", as used herein, refers to any member of a diverse population of morphologically similar cell types found in lymphoid or non-lymphoid tissues. Dendritic cells are a class of "professional" antigen presenting cells, and have a high capacity for sensitizing MHC-restricted T cells. Dendritic cells may be recognized by function, or by phenotype, particularly by cell surface phenotype. These cells are characterized by their distinctive morphology, intermediate to high levels of surface MHC-class II expression and ability to present antigen to T cells, particularly to naive T cells (Steinman et al. (1991) Ann. Rev. Immunol. 9:271; incorporated herein by reference for its description of such cells). The dendritic cells affected by the methods of the invention may be selected to be immature or mature dendritic cells.

Dendritic cells include groups of bone marrow-derived cells with dendritic morphology distributed in various tissues and organs in the body, groups of cells with dendritic morphology distributed in various organs and tissues in the body that result from in vitro differentiation using cytokines or such from bone marrow- or blood-derived stem cells and equivalent cells. Specifically, the dendritic cells include, for example, lymphocytic dendritic cells (including cells which induce Th2 or immune tolerance), bone marrow dendritic cells (generally used dendritic cells, including immature and mature dendritic cells), Langerhans cells (dendritic cells important as antigen-presenting cells in the skin), interdigitating cells (distributed in the lymph nodes and spleen T cell region, and believed to function in antigen presentation to T cells), and follicular dendritic cells (important as antigen-presenting cells for B cells. The cell surface of dendritic cells is unusual, with characteristic veil-like projections, and is characterized by expression of the cell surface markers $CD1a^+$, $CD4^+$, $CD86^+$, or $HLA-DR^+$. Mature dendritic cells are typically CD11c+, while precursors of dendritic cells include those having the phenotype $CD11c^-$, $IL-3R\alpha^{low}$; and those that are $CD11c-IL-3R\alpha^{high}$. Treatment with GM-CSF in vivo preferentially expands $CD11b^{high}$, $CD11c^{high}$ DC, while Flt-3 ligand has been shown to expand $CD11c^+$ $IL-3R\alpha^{low}$DC, and $CD11c^-$ $IL-3R\alpha^{high}$ DC precursors.

"Tolerogenic dendritic cell" means a dendritic cell that is derived from an immature dendritic cell exposed to a differentiation stimulus, which can be a combination of cytokines, hormones, vitamins and other biological agents whereby the dendritic cell acquires the ability of inducing tolerance. A tolerogenic dendritic cell has low ability to activate effector T cells but high ability to induce and activate regulatory T cells. A tolerogenic dendritic cell can be seen as a maturation-resistant cell that acts as "an immature DC" with a stable phenotype that is preserved, even in the presence of pro-inflammatory signals".

In a first step, the method for obtaining a population of tolerogenic dendritic cells comprises incubating a population of dendritic cell precursors under conditions adequate for the formation of a population of immature dendritic cells. The term "dendritic cell precursor", as used herein, refers to any cell capable of differentiating into an immature dendritic cell in the presence of an appropriate cytokine (specifically, G-CSF, GM-CSF, TNF-a, IL-4, IL-13, SCF (c-kit ligand), Flt-3 ligand, or a combination thereof), and preferably is a cell that can differentiate into an immature dendritic cell in four weeks or less, more preferably in 20 days or less, even more preferably in 18 days or less, and still more preferably in 16 days or less. Examples of dendritic precursor cells include, but are not limited to, myeloid dendritic precursor cells, lymphoid dendritic precursor cells and plasmacytoid dendritic precursor cells. Phenotypic surface markers expressed by various subsets of dendritic precursor cells are well known in the art and may be used for the purpose of identification, for example, by flow cytometry or using immunohistochemical techniques.

In a preferred embodiment, the population of dendritic precursor cells is a population of monocytic dendritic precursor cells. "Monocytic dendritic cell precursors" as used herein, comprise monocytes that have the GM-CSF receptor on their surface and other myeloid precursor cells that are responsive to GM-CSF. The cells can be obtained from any tissue where they reside, particularly lymphoid tissues such as the spleen, bone marrow, lymph nodes and thymus. Monocytic dendritic cell precursors also can be isolated from the circulatory system. Peripheral blood is a readily accessible source of monocytic dendritic cell precursors. Umbilical cord blood is another source of monocytic dendritic cell precursors.

Monocytic dendritic cell precursors may be obtained from peripheral blood mononuclear cells (PBMCs), which can be obtained either from whole blood diluted 1:1 with buffered saline or from leukocyte concentrates ("buffy coat" fractions, MSKCC Blood Bank) by standard centrifugation over Ficoll-Paque PLUS (endotoxin-free, #17-1440-03, Amersham Pharmacia Biotech AB, Uppsala, Sweden). MoDC precursors are tissue culture plastic-adherent (#35-3003; Falcon, Becton-Dickinson Labware, Franklin Lakes, N.J.) PBMCs, and can be cultured in complete RPMI 1640 plus 1% normal human serum (NHS) in the presence of GM-CSF (1000 IU/ml) and IL-4 (500 IU/ml) with replenishment every 2 days as described. (Thurner B et al., 1999, J. Immunol. Meth.; 223:1-15 and Ratzinger G. et al., 2004, J. Immunol. 173:2780-2791). In general, monocytic dendritic cell precursors may be identified by the expression of markers such as CD13 and CD33. Myeloid dendritic precursors may differentiate into dendritic cells via CD14 or CD1a pathways. Accordingly, a dendritic precursor cell of the invention may be a $CD14^+CD1a^-$ dendritic precursor cell or a $CD14^-CD1a^+$ dendritic precursor cell. In certain embodiments of the invention, a myeloid dendritic precursor cell may be characterised by a $CD34^+CD33^+CD7^-CD10^-$ phenotype. In a preferred embodiment, the myeloid dendritic precursor cell is a $CD14^+$ monocyte. The $CD14^+$ monocyte may also express the GM-CSF receptor.

The dendritic precursor cells that are being used as starting material for the method of the invention can be autologous to the subject that is to be treated. In other embodiments, the dendritic cells that are being used as starting material for the methods of the invention are heterologous dendritic cells. For example, if graft-versus-host disease is to be treated, the dendritic cells that are being used as starting material are dendritic cells that were obtained from the donor. The subject can be, e.g., a mouse, a rat, a dog, a chicken, a horse, a goat, a donkey, or a primate. Most preferably, the subject is a human.

The expression "conditions adequate for the formation of a population of immature dendritic cells", as used herein, refers to conditions which result in the differentiation of the dendritic precursor cells into immature precursor cells. Suitable conditions include, for example, by culturing for about three days in the presence of SCF (50 ng/ml), GM-CSF (500 U/ml), and TNF-a (50 ng/ml) followed by culture in the presence of SCF (50 ng/ml), GM-CSF (500 U/ml), IL-4 (250 U/ml), and TNF-$\alpha$ (50 ng/ml), more preferably, in the presence of GM-CSF (20 ng/ml) and IL-4 (20 ng/ml), or in the presence of GM-CSF (20 ng/ml) and SCF (10 ng/ml).

This treatment leads to the generation of immature dendritic cells. "Immature dendritic cells" refers to dendritic cells having significantly low T cell-activating ability as compared with in a mature state. Specifically, the immature dendritic cells may have an antigen-presenting ability that is lower than ½, preferably lower than ¼ of that of dendritic cells which maturation had been induced by adding LPS (1 µg/ml) and culturing for two days. The antigen-presenting ability can be quantified, for example, using the allo T cell-activating ability (mixed lymphocyte test: allo T cells and dendritic cells are co-cultured at a T cell:dendritic cell ratio of 1:10, or preferably at varied ratios; 3H-thymidine is added 8 hours before terminating cultivation, and the T cell growth capacity is assessed based on the amount of 3H-thymidine incorporated into the DNA of the T cells (see Gene Therapy 7; 249-254 (2000)). Alternatively, it can be assessed by testing the ability to induce specific cytotoxic T cells (CTLs) using a peptide, in which a known class I-restricted peptide of a certain antigen is added to dendritic cells; the dendritic cells are co-cultured with T cells obtained from peripheral blood of the same healthy donor from whom the dendritic cells had been collected (with 25 U/ml or preferably 100 U/ml of IL-2 on day 3 or later). The T cells are preferably stimulated with dendritic cells three times during 21 days, more preferably stimulated with dendritic cells twice during 14 days. The resulting effector cells are co-cultured for four hours with 51 Cr-labeled target cells (peptide-restricted class I positive tumor cells) at a ratio of 100:1 to 2.5:1 (100:1, 50:1, 25:1, 20:1, 12.5:1, 10:1, 5:1, or 2.5:1), preferably at a ratio of 10:1; and 51Cr released from the target cells is quantified (see Arch Dermatol Res 292: 325-332 (2000)). Furthermore, the immature dendritic cells preferably have phagocytic ability for antigens, and more preferably show low (for example, significantly low as compared to mature DCs induced by LPS as described above) or negative expression of receptors that induce the costimulation for T cell activation.

In a preferred embodiment, the first step of the method is carried out in the presence of a composition of matter selected from the group consisting of
 (i) A C4BP iso form lacking the beta chain,
 (ii) a polypeptide according to the invention,
 (iii) a peptide according to the invention,
 (iv) a polynucleotide according to the invention and
 (v) a vector according to the invention.

The terms "C4BP isoform lacking the beta chain", "polypeptide of the invention", "peptide according to the invention" and "vector according to the invention" have been described in detail above.

The step carried out in the presence of a C4BP isoform lacking the beta chain or of the polynucleotide encoding said molecule may be performed in vivo or ex vivo. Generally, in these methods, immature dendritic cells may be exposed to the C4BP isoform lacking the beta chain within a range having: a lower end of 0.01, 0.05, 0.1, 0.5, 1, 2, 3, 4, 5, 6, 7, 8, 9, 10, 12, 15, 20, 50, or 100 micrograms per ml of media; and an upper end of 0.05, 0.1, 0.5, 1, 2, 3, 4, 5, 6, 7, 8, 9, 10, 12, 15, 20, 50, 100, or 200 micrograms per ml of media. Most preferably, DC are matured in the presence of 1-10 µg/ml of the C4BP $\alpha_7\beta_0$ or $\alpha_6\beta_0$ isoforms and, most preferably, at 2, 5 and 10 µg/ml.

In a second step, the immature dendritic cells isolated according to the first step are then incubated under conditions adequate for the maturation of said immature dendritic cells into tolerogenic mature dendritic cells. Compositions highly enriched for tolerogenic dendritic cells are achieved in this manner.

Mature human dendritic cells are cells that are positive for the expression of CD40, CD80, CD86, and HLA-class II. An immature dendritic cell can be distinguished from a mature dendritic cell, for example, based on markers selected from the group consisting of CD80 and CD86. An immature dendritic cell is weakly positive and preferably negative for these markers, while a mature dendritic cell is positive. Mature DCs lose the ability to take up antigen and the cells display up-regulated expression of co-stimulatory cell surface molecules and secrete various cytokines Specifically, mature DCs express higher levels of MHC class I and II antigens and are generally identified as $CD80^+$, $CD83^+$, and $CD86^+$. Greater MHC expression leads to an increase in antigen density on the DC surface, while up regulation of co-stimulatory molecules CD80 and CD86 strengthens the T cell activation signal through the counterparts of the co-stimulatory molecules, such as CD28 on the T cells.

The expression "conditions adequate for the maturation of said immature dendritic cells into tolerogenic mature dendritic cells", as used herein, refers to methods which allow the maturation of a immature dendritic cell into a tolerogenic mature dendritic cell. Mature dendritic cells can be prepared (i.e., matured) by contacting the immature dendritic cells with effective amounts or concentrations of a dendritic cell maturation agent. Dendritic cell maturation agents can include, for example, BCG, IFN$\gamma$, LPS, TNF$\alpha$ and the like. Effective amounts of BCG typically range from about $10^5$ to $10^7$ cfu per milliliter of tissue culture media. Effective amounts of IFN$\gamma$ typically range from about 100-1000 U per milliliter of tissue culture media. *Bacillus* Calmette-Guerin (BCG) is an avirulent strain of *M. bovis*. As used herein, BCG refers to whole BCG as well as cell wall constituents, BCG-derived lipoarabidomannans, and other BCG components that are associated with induction of a type 2 immune response. BCG is optionally inactivated, such as heat-inactivated BCG, formalin-treated BCG, and the like.

The immature DCs are typically contacted with effective amounts of BCG and IFN$\gamma$ for about one hour to about 48 hours. The immature dendritic cells can be cultured and matured in suitable maturation culture conditions. Suitable tissue culture media include AIM-V$^{and\ \#174;}$, RPMI 1640, DMEM, X-VIVO 15™, and the like. The tissue culture media can be supplemented with amino acids, vitamins, cytokines, such as GM-CSF, divalent cations, and the like, to promote maturation of the cells. Typically about 500 units/ml of GM-CSF is used.

In a preferred embodiment, the second step is carried out in the presence of a composition of matter selected from the group consisting of (i) A C4BP iso form lacking the beta chain,
(ii) a polypeptide according to the invention,
(iii) a peptide according to the invention,
(iv) a polynucleotide according to the invention and
(v) a vector according to the invention.

Maturation of dendritic cells can be monitored by methods known in the art for dendritic cells. Cell surface markers can be detected in assays familiar to the art, such as flow cytometry, immunohistochemistry, and the like. The cells can also be monitored for cytokine production (e.g., by ELISA, another immune assay, or by use of an oligonucleotide array). Mature DCs of the present invention also lose the ability to uptake antigen, which can be analyzed by uptake assays familiar to one of ordinary skill in the art.

The term "mature dendritic cells" refers to dendritic cells that have significantly strong antigen-presenting ability for T cell or the like as compared with in the immature state. Specifically, the mature dendritic cells may have an antigen-presenting ability that is half or stronger, preferably equivalent to or stronger than the antigen-presenting ability of dendritic cells in which maturation has been induced by adding LPS (1 µg/ml) and culturing for two days. Furthermore, the mature dendritic cells preferably have weak or no phagocytic ability for antigen, and more preferably are positive for the expression of receptors that induce the costimulation for T cell activation. The activation of dendritic cells refers to the transition from immature to mature dendritic cell; and the activated dendritic cells encompass mature dendritic cells and dendritic cells in the process of the transition, wherein the expression of CD80 and CD86 that induce costimulatory signals are elevated by the activating stimuli.

The population of tolerogenic cells may comprise at or about 50% or more of the cell composition, and preferably be at or about 75% or more of the cell composition, and may be 90% or more. The desired cells are identified by their surface phenotype, by the ability to induce tolerance, etc. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for tolerogenic dendritic cells may be used in a variety of screening assays and cultures, as described below.

DCs may optionally be further purified by sorting of fluorescence-labeled cells using antibodies against DC markers. DCs may also be isolated using antibodies against DCs, wherein the antibodies are linked to magnetic beads. In a specific embodiment, DCs that co-express CD32a and CD32b are isolated using FACS.

The separated cells may be collected in any appropriate medium that maintains the viability of the cells, usually having a cushion of serum at the bottom of the collection tube. Various media are commercially available and may be used according to the nature of the cells. Culture medium may be liquid or semi-solid, e.g. containing agar, methylcellulose, etc. The cell population may be conveniently suspended in an appropriate nutrient medium, such as Iscove's modified dMEM, HBSS, dPBS, RPMI, Iscove's medium, DMEM or RPMI-1640 and the like, normally supplemented with fetal calf serum (about 5-10%), L-glutamine, a thiol, particularly 2-mercaptoethanol, and antibiotics, e.g. penicillin and streptomycin.

Optionally, standard techniques such as morphological observation and immunochemical staining, can be used to verify the presence of dendritic cells. For example, the purity of dendritic cells can be assessed by flow cytometry using fluorochrome-labeled antibodies directed against one or more of the characteristic cell surface markers.

In certain embodiments, the invention provides methods for producing antigen-specific tolerogenic dendritic cells. To generate antigen-specific tolerogenic dendritic cells, dendritic cells are subjected to a method of the invention to inhibit the maturation of the dendritic cells, and subsequently or concurrently, the dendritic cells are contacted with one or more antigens against which tolerance is desired. If antigen-specific tolerogenic dendritic cells are to be used to treat an autoimmune disease, the antigen or antigens are the antigen(s) that cause(s) the immune reaction that underlies the autoimmune disease. In certain, more specific embodiments, the tolerogenic dendritic cells (i.e., dendritic cells, the maturation of which has been inhibited by a method of the invention) are contacted with a plurality of different antigens to produce a population of antigen-specific tolerogenic dendritic cells. In other embodiments, for example if the tolerogenic dendritic cells are to be used to treat graft-versus-host disease, tolerogenic dendritic cells (i.e., dendritic cells, the maturation of which has been inhibited by a method of the invention) are contacted with tissue from the graft, wherein the tissue is complexed with or bound to antibody to produce a population of tolerogenic dendritic cells specific for graft antigens.

In certain embodiments, antigen-specific tolerogenic dendritic cells can be generated by (a) contacting an immature dendritic cell with a C4BP isoform lacking the beta chain, a polypeptide according to the invention, a peptide according to the invention, a polynucleotide according to the invention or a vector according to the invention and (b) exposing the cell to an antigen, wherein the antigen is the antigen against which tolerance is desired, e.g., a self-antigen. In a specific embodiment, steps (a) and (b) are performed sequentially, such that step (a) is performed first followed by step (b). Antigen-specific tolerogenic dendritic cells of the invention may also be loaded with antigen for presentation by transducing the cells with RNA encoding the antigen (see, e.g., U.S. Pat. Nos. 6,387,701; 6,670,186; U.S. application Ser. No. 10/362,715). The methods of the invention may also be combined with other methods known in the art to provide additional advantages (see, e.g., U.S. Pat. No. 5,831,068; U.S. application Ser. No. 11/246,387).

In some embodiments, the tolerogenic dendritic cells are used to produce regulatory T cells (see, e.g., U.S. patent application Ser. No. 10/661,804). Briefly, regulatory T cells may be produced from a population comprising CD4+ T cells and/or CD8+ T cells. These T cell populations may be isolated from a subject or may be cultured. Subpopulations of T cells may also be used, such as, for example, populations sorted by cell surface marker so as to comprise enriched populations of particular cells (e.g., CD4+ CD25+ T cells or CD4+ CD25⁻ T cells). The T cells are then cultured or incubated with tolerogenic dendritic cells of the invention. If the regulatory T cells are being produced in vitro, the tolerogenic dendritic cells may be allogeneic to or syngeneic with the T cells. In some embodiments, the tolerogenic DCs are loaded with antigen {e.g., pulsed with antigen or transfected with antigen-encoding RNA). In such embodiments, the tolerogenic DCs may present the antigen to T cells. During production of regulatory T cells, the T cells may be exposed to and/or cultured with the tolerogenic DCs once or more than once. For example, the T cells may be cultured with DCs for days or weeks; the DCs in the mixed culture may be replenished if necessary. In some embodiments, culture will continue until a therapeutic amount of regulatory T cells has been obtained. Other culture techniques and/or additives may be used to improve the results obtained; for example, the culture media may also contain cytokines such as IL-2.

Generally, regulatory T cells secrete IL-10 and/or TGF-beta (see, e.g., Walsh et al., 2004, J. Clin. Invest. 114: 1398-1403); assays for confirming secretion of these cytokines are known in the art. In some embodiments, regulatory T cells will inhibit a mixed lymphocyte reaction by at least 10%, 20%, 30%, 40%, 50%, 75%, 90%, 95%, or 100%. Mixed lymphocyte reaction assays are well-known in the art. The regulatory T cells of the invention may be antigen-specific. CD4+ CD25+ regulatory T cells generally express characteristic cell surface markers including CD4, CD25, and Foxp3; assays for cell surface markers are well-known in the art.

Tolerogenic Dendritic Cells of the Invention Obtained Using C4BP Isoforms Lacking the β Chain and Therapeutic Uses Thereof In another aspect, the invention relates to tolerogenic dendritic cells of the invention obtained by differentiating and/or maturing dendritic cells in the presence of a C4BP isoform lacking the β chain, a polypeptide comprising the C4BP alpha chain, a peptide as defined in the invention, a polynucleotide encoding any of said polypeptides or a vector comprising said polypeptide.

The tolerogenic dendritic cells according to the invention are characterized by showing one or more of the following features:

The cell is HLA-DR$^+$. The term "positive", when applied to a given marker, indicates that the level of expression of a particular cell surface marker on a tolerogenic DC produced by a method of the invention is substantially the same as in an appropriate control cell (e.g., a native mature immunostimulatory DC, or a mature immunostimulatory DC obtained via in vitro maturation).

The cell is CD80$^-$, CD83$^-$, CD86$^-$, CD1a$^-$, CCR7$^-$, IDO$^-$ and/or, BIC-1$^-$. The term "negative", when applied to a given marker, indicates that the level of expression of a particular cell surface marker on a tolerogenic DC produced by a method of the invention is decreased by 10%, 20%, 30%, 40%, 50%, 60%, 70%, 80%, 90%, 95%, 97%, 98%, 99%, or 100%, or is undetectable, in comparison to the level of expression of the same cell surface marker on an appropriate control cell (e.g., a native mature immunostimulatory DC, or a mature immunostimulatory DC obtained via in vitro maturation).

The cell does not secrete or secretes reduced amounts of inflammatory cytokines such as IL-12p70, TNF-α, IFN-γ, IL-8 and/or IL-6 with respect to mature dendritic cells. The term "secrete reduced amounts", when applied to a given cytokine, indicates that the level of secretion of a particular cytokine on a tolerogenic DC produced by a method of the invention is decreased by 10%, 20%, 30%, 40%, 50%, 60%, 70%, 80%, 90%, 95%, 97%, 98%, 99%, or 100%, or is undetectable, in comparison to the level of secretion of the same cell surface marker on an appropriate control cell (e.g., a native mature immunostimulatory DC, or a mature immunostimulatory DC obtained via in vitro maturation).

The cell secretes increased amounts of IL-10 with respect to mature dendritic cells. The term "secrete increased amounts", when applied to a given cytokine, indicates that the level of secretion of a particular cytokine on a tolerogenic DC produced by a method of the invention is increased by 10%, 20%, 30%, 40%, 50%, 60%, 70%, 80%, 90%, 95%, 97%, 98%, 99%, or 100% in comparison to the level of secretion of the same cell surface marker on an appropriate control cell (e.g., a native mature immunostimulatory DC, or a mature immunostimulatory DC obtained via in vitro maturation).

The cell shows round morphology. The term "round morphology", as used herein, refers to a morphology wherein the cells show a number of projections protruding from the cell surface which is decreased by 10%, 20%, 30%, 40%, 50%, 60%, 70%, 80%, 90%, 95%, 97%, 98%, 99%, or 100%, or is undetectable, in comparison to the number of projections on an appropriate control cell (e.g., a native mature immunostimulatory DC, or a mature immunostimulatory DC obtained via in vitro maturation). The morphology of a cell can be determined, i.e. by scanning electron microscopy, as described in example 4 of the present invention, The cell remains viable after the differentiation/maturation process. The term "viable", as used herein, refers to populations wherein less than 50%, less than 40%, less than 30%, less than 20%, less than 10%, less than 5%, less than 4%, less than 3%, less than 2%, less than 2% or less than 1% undergo apoptosis after the treatment with a maturation stimuli. Apoptosis can be determined by any method commonly known in the art such as Annexin V/7-ADD staining, caspase-3 activation assay, TUNEL and DNA fragmentation assay, determination of the mitochondrial membrane potential and the like.

The cell shows reduced chemotactic behaviour towards CCL21 with respect to mature dendritic cells. The term "reduced chemotactic behaviour", as used herein, indicates that the level of chemotaxis of a cell produced by a method of the invention towards CCL21 on a tolerogenic DC is decreased by 10%, 20%, 30%, 40%, 50%, 60%, 70%, 80%, 90%, 95%, 97%, 98%, 99%, or 100%, or is undetectable, in comparison to the level of chemotaxis towards the same cytokine on an appropriate control cell (e.g., a native mature immunostimulatory DC, or a mature immunostimulatory DC obtained via in vitro maturation). The chemotactic behaviour of a tolerogenic dendritic cell towards CCL21 can be determined, for instance, as described in example 5 of the present invention and/or The cell shows a decreased capability of inhibiting allogenic T cell proliferation with respect to mature dendritic cells. The term "decreased capability of inhibiting allogenic T cell proliferation", as used herein, indicates that the level of proliferation of allogenic T cells contacted with a cell produced by a method of the invention is decreased by 10%, 20%, 30%, 40%, 50%, 60%, 70%, 80%, 90%, 95%, 97%, 98%, 99%, or 100%, or is undetectable, in comparison to the level of proliferation observed in allogenic T cells contacted with an appropriate control cell (e.g., a native mature immunostimulatory DC, or a mature immunostimulatory DC obtained via in vitro maturation). The capacity of a tolerogenic dendritic cell to inhibit allogeneic T cell proliferation can be carried out, for instance, as described in example 6 of the present invention.

The cell shows a stable immunomodulatory phenotype that is preserved in the presence of pro-inflammatory signals, in contrast to immature DCs. The capacity of a tolerogenic dendritic cell of showing a stable immunomodulatory phenotype can be determined, for instance, as described in example 16 of the present invention.

The cell shows the capability of inhibiting Th1 differentiation under pro-inflammatory conditions with respect to mature dendritic cells. The term "inhibiting Th1 differentitation", as used herein, indicates that the level of Th1 cells produced by the T cells contacted with a cell produced by a method of the invention is decreased by 10%, 20%, 30%, 40%, 50%, 60%, 70%, 80%, 90%, 95%, 97%, 98%, 99%, or 100%, or is undetectable, in comparison to the level of Th1 differentiation observed in T cells contacted with an appropriate control cell (e.g., a native mature immunostimulatory DC, or a mature immunostimulatory DC obtained via in vitro maturation). The capacity of a tolerogenic dendritic cell to inhibit Th1 differentiation can be determined, for instance, measuring the IFN-gamma production as described in example 17 of the present invention.

The cell shows an increased capability of generating regulatory T cells (Treg) with respect to mature dendritic cells. The term "increased capability of generating regulatory T cells", as used herein, indicates that the level of generation of regulatory T cells of T cells contacted with a cell produced by a method of the invention is increased by 10%, 20%, 30%, 40%, 50%, 60%, 70%, 80%, 90%, 95%, 97%, 98%, 99%, or 100%, in comparison to the level of generation of T cells contacted with an appropriate control cell (e.g., a native mature immunostimulatory DC, or a mature immunostimulatory DC obtained via in vitro maturation). The capacity of a tolerogenic dendritic cell to generate regulatory T cells (Treg) can be determined, for instance, as described in example 17 of the present invention. In a preferred embodiment, the tolerogenic cells according to the invention are HLA-DR$^+$, CD80$^-$, CD83$^-$, CD86$^-$, CD1a$^-$, CCR7$^-$, IDO$^-$ and/or, BIC-1$^-$. In a preferred embodiment, the tolerogenic cells according to the invention are CD40$^+$. In another preferred embodiment, the tolerogenic cells according to the invention are CD40$^-$.

In a preferred embodiment, the tolerogenic cells according to the invention are characterized by showing one or more of the above features:
CD1a$^-$,
CD86$^-$
IDO$^-$
Apoptosis resistant In a preferred embodiment, the tolerogenic cells according to the invention are CD1a$^-$. In another preferred embodiment, the tolerogenic cells according to the invention are CD1a$^-$ and CD86$^-$. In another preferred embodiment, the tolerogenic cells according to the invention are CD1a$^-$, CD86$^-$ and IDO$^-$. In another preferred embodiment, the tolerogenic cells according to the invention are CD1a$^-$, CD86$^-$, IDO$^-$ and apoptosis resistant. In a preferred embodiment, the tolerogenic cells according to the invention are CD1a$^-$ and IDO$^-$. In another preferred embodiment, the tolerogenic cells according to the invention are CD1a$^-$ and apoptosis resistant. In a preferred embodiment, the tolerogenic cells according to the invention are CD86$^-$ and IDO$^-$. In another preferred embodiment, the tolerogenic cells according to the invention are CD86$^-$ and apoptosis resistant. In another preferred embodiment, the tolerogenic cells according to the invention are IDO$^-$ and apoptosis resistant.

In another embodiment, the tolerogenic dendritic cells according to the present invention are capable of inducing Ag-specific tolerance (or hyporesponsiveness) of human memory CD4$^+$ T cells by our tolerogenic, C4BP (b$^-$)- or Factor H-treated DCs". Table 3 provides a summary of the features of tolerogenic cells according to the invention in comparison with immature dendritic cells, mature dendritic cells and tolerogenic dendritic cells obtained by treating immature dendritic cells with vitamin D3.

TABLE 3

Differential traits of C4BP (β$^-$)-treated and Factor H-treated dendritic cells. DCs, untreated, immature DCs; mDCs, untreated and LPS-induced DCs; C4BP (β$^-$) DCs, C4BP (α7β0)- or C4BP (α6β0)-treated and LPS-induced DCs; FH DCs, Factor H-treated and LPS-induced DCs; Vit D$_3$ DCs, Vit D$_3$-treated and LPS-induced DCs.

| | | | +LPS induction | | |
| --- | --- | --- | --- | --- | --- |
| | iDCs | mDCs | C4BP (β$^-$) DCs | FH DCs | Vit D$_3$ DCs |
| Phenotype (RNA/protein expression) | | | | | |
| Surface Markers | | | | | |
| HLA-DR | ++ | +++ | +++ | ++ | + |
| CD40 | ++ | +++ | ++ | ++ | + |
| CD83 | − | +++ | + | + | + |
| CD86 | + | +++ | + | + | − |
| CD14 | − | − | + | + | + |
| CD1a | ++ | ++ | + | + | − |
| CCR7 | + | +++ | ++ | ++ | ++ |
| Cytokines | | | | | |
| IL-12 | − | +++ | − | − | − (*) |
| IL-6 | − | +++ | + | + | n.d. |
| IL-8 | + | +++ | ++ | ++ | n.d. |
| IL-10 | − | ++ | +++ | + | ++ (*) |
| TNF-α | − | +++ | + | + | n.d. |
| IFN-γ | − | +++ | − | − | n.d. |
| Transcriptional profile | | | | | |
| IDO | + | +++ | − | − | +++ (**) |
| BIC-1 | + | +++ | + | + | n.d. |
| SOD-2 | ++ | +++ | n.d. | + | |
| Morphology | | | | | |
| Dendrite density and lenght | + | +++ | + | + | n.d. |
| Viability | | | | | |
| Apoptosis after treatment | − | − | − | − | + |
| Functional assays | | | | | |
| Endocytosis (DQ-OVA) | +++ | + | + | + | n.d. |
| Chemotaxis (CCL21) | n.d | +++ | − | − | n.d. |
| Alloproliferation (T CD3$^+$) | + | +++ | + | + | − |

(−) negligible; (+) low; (++) moderate; (+++) high; n.d., not determined.
(*) Data extracted from: Naranjo-Gomez et al. (2011) *J. Transl. Med.* 9: 89.
(**) Data extracted from: Heitger (2011) *Curr. Med. Chem.* 18: 2222-33

In another aspect, the invention relates to a cell population comprising at least 50%, at least 60%, at least 70%, at least 80%, at least 90%, at least 95%, at least 96%, 97%, 98% or 99% of tolerogenic dendritic cells of the invention; preferably, the cell population comprises at least 80% of tolerogenic dendritic cells of the invention. In yet another aspect, the invention relates to a tolerogenic dendritic cell population obtained using a C4BP isoform lacking the β chain, a polypeptide comprising the C4BP alpha chain as defined in the invention, a peptide as defined in the invention, a polynucleotide encoding any of said polypeptides or a vector comprising said polypeptide for use in the prevention and/or treatment of an immunological disease. In another aspect, the invention relates to the use of a tolerogenic cell obtained using a C4BP isoform lacking the β chain, a polypeptide comprising the C4BP alpha chain as defined in the invention, a peptide as defined in the invention, a polynucleotide encoding any of said polypeptides or a vector comprising said polypeptide for the manufacture of a medicament for the prevention and/or treatment of an immunological disease.

In another aspect, the invention relates to a method for the prevention and/or treatment of an immunological disease in a subject in need thereof which comprises the administration to said subject of a tolerogenic cell obtained using a C4BP isoform lacking the β chain, a polypeptide comprising the C4BP alpha chain as defined in the invention, a peptide as defined in the invention, a polynucleotide encoding any of said polypeptides or a vector comprising said polypeptide.

In another aspect, the invention relates to a method for increasing regulatory T cell population in a subject in need thereof which comprises the administration to said subject of a tolerogenic dendritic cell population obtained using a C4BP isoform lacking the β chain, a polypeptide comprising the C4BP alpha chain as defined in the invention, a peptide as defined in the invention, a polynucleotide encoding any of said polypeptides or a vector comprising said polypeptide.

In another aspect, the invention relates to a tolerogenic dendritic cell population obtained using a C4BP isoform lacking the β chain, a polypeptide comprising the C4BP alpha chain as defined in the invention, a peptide as defined in the invention, a polynucleotide encoding any of said polypeptides or a vector comprising said polypeptide for use in increasing a regulatory T cell population.

The prevention and/or treatment of an immunological disease is achieved through the increase of a regulatory T cell population.

The expression "increasing regulatory T cell population", as used herein, means that the tolerogenic dendritic cell population of the invention produces an increase in the number of regulatory T cells with respect to a subject treated with an appropriate control cell (e.g., a native mature immunostimulatory DC, or a mature immunostimulatory DC obtained via in vitro maturation). The regulatory T cell population is increased by 10%, 20%, 30%, 40%, 50%, 60%, 70%, 80%, 90%, 95%, 97%, 98%, 99%, or 100% in comparison with a subject treated with a control cell. The capacity of the tolerogenic dendritic cell population of the invention of increasing regulatory T cell population can be determined, for instance, as described in example 17.

Therapeutic Methods of the Invention

In another embodiment, methods are provided for treating and/or preventing immunological diseases using the polypeptides, polynucleotides and vectors of the invention. The immunological disease to be treated with the compositions according to the present invention include, without limitation, an immunoinflammatory disease, sepsis, an autoimmune disease, transplant rejection, graft-versus-host disease and a hypersensitivity disease. A subject in need of such treatment may be a human or may be a non-human primate or other animal (i.e., veterinary use) who has developed symptoms of an immunological disease or who is at risk for developing an immunological disease. Examples of non-human primates and other animals include but are not limited to farm animals, pets, and zoo animals (e.g., horses, cows, buffalo, llamas, goats, rabbits, cats, dogs, chimpanzees, orangutans, gorillas, monkeys, elephants, bears, large cats, etc.).

The expressions "immunoinflammatory disease", "sepsis", "autoimmune disease" and "transplant rejection" have been described in detail above and are used with the same meaning in the context of the therapeutic method of the invention.

As used herein, a patient (or subject) may be any mammal, including a human, that may have or be afflicted with an immunological disease or disorder, or that may be free of detectable disease. Accordingly, the treatment may be administered to a subject who has an existing disease, or the treatment may be prophylactic, administered to a subject who is at risk for developing the disease or condition.

The dose of the composition for treating an immunological disease or disorder may be determined according to parameters understood by a person skilled in the medical art. Accordingly, the appropriate dose may depend upon the patient's (e.g., human) condition, that is, stage of the disease, general health status, as well as age, gender, and weight, and other factors familiar to a person skilled in the medical art.

In an aspect, the invention relates to a method for increasing tolerogenic dendritic cell and/or regulatory T cell populations in a subject in need thereof comprising the administration to said subject of a polypeptide according to the invention, a peptide according to the invention, a polynucleotide according to the invention or a vector according the invention.

In yet another aspect, the invention relates to a polypeptide according to the invention, a peptide according to the invention, a polynucleotide according to the invention or a vector according to the invention for use in increasing a tolerogenic dendritic cell population and/or a regulatory T cell population.

The prevention and/or treatment of an immunological disease is achieved through the increase of a tolerogenic dendritic cell population and/or a regulatory T cell population.

The expression "increasing tolerogenic dendritic cell population" is understood to mean that the administration of a polypeptide according to the invention, a peptide according to the invention, a polynucleotide according to the invention or a vector according the invention produces an increase in the number of tolerogenic dendritic cells with respect to an untreated subject. The tolerogenic dendritic cell population is increased by 10%, 20%, 30%, 40%, 50%, 60%, 70%, 80%, 90%, 95%, 97%, 98%, 99%, or 100% in comparison with an untreated subject. The capacity of a polypeptide according to the invention, a peptide according to the invention, a polynucleotide according to the invention or a vector according the invention of increasing a tolerogenic dendritic cell population can be determined, for instance, as described in examples 1 to 5.

The expression "increasing regulatory T cell population", as used herein, means that a polypeptide according to the invention, a peptide according to the invention, a polynucleotide according to the invention or a vector according the invention produces an increase in the number of regulatory T cells with respect to an untreated subject. The regulatory T cell population is increased by 10%, 20%, 30%, 40%, 50%, 60%, 70%, 80%, 90%, 95%, 97%, 98%, 99%, or 100% in comparison with an untreated subject. The capacity of a polypeptide according to the invention, a peptide according to the invention, a polynucleotide according to the invention or a vector according the invention of increasing regulatory T cell population can be determined, for instance, as described in example 17.

Pharmaceutical Compositions of the Invention

The invention also provides pharmaceutical compositions comprising a polypeptide according to the invention, a polynucleotide according to the invention, a vector according to the invention, a cell according to the invention or a tolerogenic dendritic cell according to the invention.

A composition may be a pharmaceutical composition that is a sterile aqueous or non-aqueous solution, suspension or emulsion, which additionally comprises a physiologically acceptable or suitable carrier. A pharmaceutically acceptable or suitable carrier may include (or refer to) an excipient (i.e., a non-toxic material that does not interfere with the activity of the active ingredient) and/or a diluent. Such compositions may be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable excipient or carrier known to those of ordinary skill in the art for use in pharmaceutical compositions may be employed in the compositions described herein. Excipients for therapeutic use are well known, and are described, for example, in Remingtons Pharmaceutical Sciences, Mack Publishing Co. (A. R. Gennaro ed. 1985). In general, the type of excipient is selected based on the mode of administration. Pharmaceutical compositions may be formulated for any appropriate manner of administration, including, for example, topical, oral, nasal, intrathecal, rectal, vaginal, intraocular, subconjunctival, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above excipients or a solid excipient or carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid. A liquid pharmaceutical composition may include, for example, one or more of the following: a sterile diluent such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The agents described herein, including polypeptides, peptides, polynucleotides, vectors cells and tolerogenic dendritic cell, may be formulated for sustained or slow release. Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

Pharmaceutical compositions may be administered in a manner appropriate to the disease to be treated (or prevented) as determined by persons skilled in the medical art. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with an immunological disease or disorder.

Optimal doses may generally be determined using experimental models and/or clinical trials. The optimal dose may depend upon the body mass, weight, or blood volume of the patient. In general, the amount of polypeptide present in a dose, or produced in situ by DNA present in a dose, ranges from about 0.01 mu g to about 1000 mu g per kg of host. The use of the minimum dosage that is sufficient to provide effective therapy is usually preferred. Patients may generally be monitored for therapeutic or prophylactic effectiveness using assays suitable for the condition being treated or prevented, which assays will be familiar to those having ordinary skill in the art. When administered in a liquid form, suitable dose sizes will vary with the size of the patient, but will typically range from about 1 ml to about 500 ml (comprising from about 0.01 mu g to about 1000 mu g per kg) for a 10-60 kg subject.

For pharmaceutical compositions comprising an agent that is a nucleic acid molecule including an aptamer, the nucleic acid molecule may be present within any of a variety of delivery systems known to those of ordinary skill in the art, including nucleic acid, and bacterial, viral and mammalian expression systems such as, for example, recombinant expression constructs as provided herein. Techniques for incorporating DNA into such expression systems are well known to those of ordinary skill in the art. The DNA may also be "naked," as described, for example, in Ulmer et al., Science 259:1745-49, 1993 and reviewed by Cohen, Science 259:1691-1692, 1993. The uptake of naked DNA may be increased by coating the DNA onto biodegradable beads, which are efficiently transported into the cells.

Nucleic acid molecules may be delivered into a cell according to any one of several methods described in the art (see, e.g., Akhtar et al., Trends Cell Bio. 2:139 (1992); Delivery Strategies for Antisense Oligonucleotide Therapeutics, ed. Akhtar, 1995, Maurer et al., Mol. Membr. Biol. 16:129-40 (1999); Hofland and Huang, Handb. Exp. Pharmacol. 137:165-92 (1999); Lee et al., ACS Symp. Ser.

752:184-92 (2000); U.S. Pat. No. 6,395,713; International Patent Application Publication No. WO 94/02595); Selbo et al., Int. J. Cancer 87:853-59 (2000); Selbo et al., Tumour Biol. 23:103-12 (2002); U.S. Patent Application Publication Nos. 2001/0007666, and 2003/077829). Such delivery methods known to persons having skill in the art, include, but are not restricted to, encapsulation in liposomes, by iontophoresis, or by incorporation into other vehicles, such as biodegradable polymers; hydrogels; cyclodextrins (see, e.g., Gonzalez et al., Bioconjug. Chem. 10: 1068-74 (1999); Wang et al., International Application Publication Nos. WO 03/47518 and WO 03/46185); poly(lactic-co-glycolic)acid (PLGA) and PLCA microspheres (also useful for delivery of peptides and polypeptides and other substances) (see, e.g., U.S. Pat. No. 6,447,796; U.S. Patent Application Publication No. 2002/130430); biodegradable nanocapsules; and bioadhesive microspheres, or by proteinaceous vectors (International Application Publication No. WO 00/53722). In another embodiment, the nucleic acid molecules for use in altering (suppressing or enhancing) an immune response in an immune cell and for treating an immunological disease or disorder can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives (see also, e.g., U.S. Patent Application Publication No. 2003/0077829).

The pharmaceutical compositions/medicaments of the invention may comprise further, e.g. active, ingredients, e.g. other immunomodulatory antibodies such as anti-ICOS, anti-CD 154, anti-CD 134L or recombinant proteins such as, but not limited to rCTLA-4 (CD 152), rOX40 (CD134), or anti-inflammatory agents or immunomodulatory compounds such as, but not limited to cyclosporin A, FTY720, RAD, rapamycin, FK506, 15-deoxyspergualin, steroids; as described above.

Therapeutic Uses of Factor H

The authors of the present invention have also found that the factor H is capable of inhibiting the activation of dendritic cells and promoting the acquisition of features characteristic of tolerogenic cell. As shown in examples 9 to 15 of the present invention, factor H is capable of down-regulating activation markers of human Mo-DCs and the release of inflammatory cytokines by LPS-matured human Mo-DCs . Moreover, factor H modify the morphology of human Mo-DCs, reduce the endocytic potential of immature DCs, reduce the chemotaxis of human Mo-DCs and the proliferation of allogeneic T cells in response to the exposure to dendritic cells.

In addition, the authors of the present invention have found that factor H generates tolerogenic dendritic cells having a decreased T cell-stimulatory capability, and the ability not only to prevent Th1 differentiation under pro-inflammatory conditions, but also to generate regulatory T cells.

Thus, in another aspect, the invention relates to a composition of matter selected from the group consisting of
  (i) Factor H or a functionally equivalent variant thereof,
  (ii) A polynucleotide encoding a Factor H or a functionally equivalent variant thereof and
  (iii) A vector comprising a polynucleotide encoding a Factor H or a functionally equivalent variant thereof
for use in the prevention and/or treatment of an immunological disease.

Thus, in another aspect, the invention relates to the use of a composition of matter selected from the group consisting of
  (i) Factor H or a functionally equivalent variant thereof,
  (ii) A polynucleotide encoding a Factor H or a functionally equivalent variant thereof and
  (iii) A vector comprising a polynucleotide encoding a Factor H or a functionally equivalent variant thereof
for the manufacture of a medicament for the prevention and/or treatment of an immunological disease.

In another aspect, the invention relates to a method for the prevention and/or treatment of an immunological disease in a subject in need thereof which comprises the administration to said subject of a composition of matter selected from the group of:
  (i) Factor H or a functionally equivalent variant thereof,
  (ii) A polynucleotide encoding a Factor H or a functionally equivalent variant thereof and
  (iii) A vector comprising a polynucleotide encoding a Factor H or a functionally equivalent variant thereof.

In another aspect, the invention relates to a method for increasing tolerogenic dendritic cell and/or regulatory T cell populations in a subject in need thereof which comprises the administration to said subject of a composition of matter selected from the group of:
  (i) Factor H or a functionally equivalent variant thereof,
  (ii) A polynucleotide encoding a Factor H or a functionally equivalent variant thereof and
  (iii) A vector comprising a polynucleotide encoding a Factor H or a functionally equivalent variant thereof.

In another aspect, the invention relates to a composition of matter selected from the group consisting of:
  (i) Factor H or a functionally equivalent variant thereof
  (ii) A polynucleotide encoding a Factor H or a functionally equivalent variant thereof
  (iii) A vector comprising a polynucleotide encoding a Factor H or a functionally equivalent variant thereof
for use in increasing tolerogenic dendritic cell and/or regulatory T cell populations.

The term "factor H", as used herein, refers to a 155 kDa glycoprotein which is found in human plasma at a concentration of about 550 µg/ml and which comprises 20 CCPs arranged head to tail, of which the four N-terminal CCPs contain the complement regulatory activity and the C-terminal two CCPs mediate surface binding and target recognition. Factor H regulates complement activation on self cells by possessing both cofactor activity for the Factor I-mediated C3b cleavage, and decay accelerating activity against the alternative pathway C3 convertase, C3bBb. Factor H protects self cells from complement activation but not bacteria/viruses, in that it binds to glycosaminoglycans that are present on host cells but not on pathogen cell surfaces. Suitable factor H polypeptides for use according to the present invention include, without limitation,
  the human factor H (corresponding to amino acids 19 to 1231 of the polypeptide provided in SwissProt database (release of May 31, 2011) under accession number P08603),
  the bovine factor H (corresponding to amino acids 19 to 1236 of the polypeptide provided in SwissProt database (release of May 31, 2011) under accession number Q28085),
  the rat factor H (corresponding to amino acids 19 to 1236 of the polypeptide provided in SwissProt database (release of May 31, 2011) under accession number Q91YB6, the mouse factor H (corresponding to amino acids 19 to 1234 of the polypeptide provided in SwissProt database (release of May 3, 2011) under accession number P06909), the human Complement factor H-related protein 1 (corresponding to amino acids 19 to 330 of the polypeptide provided in SwissProt database (release of Feb. 8, 2011) under accession number Q03591 the human Complement factor H-related protein 2 (corresponding to amino acids 19 to 270 of the polypeptide provided in SwissProt database (release of Apr. 5, 2011) under accession number P36980, the human Complement factor H-related protein 3 (corresponding to amino acids 19 to 330 of the polypeptide provided in SwissProt database (release of May 31, 2011) under accession number Q02985 the human Complement factor H-related protein 4 (corresponding to amino acids 19 to 270 of the polypeptide provided in SwissProt database (release of May 3, 2011) under accession number Q92496 and the human Complement factor H-related protein 5 (corresponding to amino acids 19 to 569 of the polypeptide provided in SwissProt database (release of Apr. 5, 2011) under accession number Q9BXR6, The term "functionally equivalent variant", when referred to factor H refers to a polypeptide resulting from the insertion, deletion or substitution of one or more amino acids of the factor H polypeptide as defined above and which substantially preserve the ability of factor H to inhibit dendritic cell proliferation. Factor H variants suitable for use according to the present invention include, without limitation, polypeptides having at least 99%, at least 98%, at least 97%, at least 96%, at least 95%, at least 94%, at least 93%, at least 92%, at least 91%, at least 90%, at least 85%, at least 80%, at least 75%, at least 70%, at least 65%, at least 60%, at least 55%, at least 50% identity with the naturally-occurring factor H as defined above. Methods for determining whether a polypeptide is a functionally equivalent variant of factor H include, without limitation, the methods described in examples 9 to 15 of the present invention based on:

The determination of the capability of the variant to down-regulate the expression of DC activation markers such as CD83, CD86, CD80, CD40, CD1a, CCR7, IDO, BIC-1 and/or SOD2.

The determination of the capability of the variant to inhibit the release of inflammatory cytokines by dendritic cells in response to stimulation with LPS.

The determination of the capability of the variant polypeptide to inhibit the acquisition of dendritic cell morphology of immature dendritic cells in response to LPS stimulation.

The determination of the capability of the variant of reducing the endocytic potential of immature dendritic cells.

The determination of the capability of the variant polypeptide of reducing the chemotaxis of dendritic cells towards a chemotactic signal (e.g. CCL21) and/or The determination of the capability of the variant polypeptide of reducing the proliferation of allogeneic T cells in response to stimulation by dendritic cells.

Thus, a polypeptide is considered as a functionally equivalent to factor H if it shows at least 100%, at least 95%, at least 90%, at least 85%, at least 80%, at least 75%, at least 70%, at least 65%, at least 60% or at least 50% of the activity of factor H as mentioned above.

In another embodiment, the functionally equivalent variant of factor H is a fusion protein comprising a first region which comprises factor H domain and a second region which comprises a polypeptide which does not form part of factor H. The fusion protein of the present invention may comprise in an amino terminal to carboxy terminal direction, (a) the region which comprises the factor H and (b) the region which comprises a polypeptide which does not form part of factor H. Alternatively, the fusion protein of the invention may comprise in an amino terminal to carboxy terminal direction, (a) the region which comprises a polypeptide which does not form part of factor H and (b) the region which comprises the factor H.

Suitable polypeptides that can be used for forming a fusion protein according to the invention include, without limitation, an immunoglobulin Fc region, albumin, ferritin or transferrin.

In a preferred embodiment, the region which comprises a polypeptide which does not form part of the factor H is an immunoglobulin Fc region.

As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH 1 domain and a CH2 domain, 3) a CH1 domain and a CH3 domain, 4) a CH2 domain and a CH3 domain, or 5) a combination of two or more CH domains and an immunoglobulin hinge region. The immunoglobulin Fc region of the fusion protein of the present invention preferably comprises or consists of an Fc or a portion of an Fc of an immunoglobulin of isotype selected from IgG, IgM, IgA, IgD, IgE, further preferably, IgG1, IgG2, IgG3, IgG4, IgA1, IgA2, sIgA, more preferably IgG2 or IgG4, most preferably IgG2.

The invention also provides therapeutic uses of polynucleotides encoding factor H or a variant thereof as well as vectors comprising said polynucleotides. The terms "polynucleotide" and "vector" have been defined in detail above and are used with the same meaning in the context of the present invention.

The expression "immunological disease" has been described in detail above and is used in the same meaning in the context of the therapeutic methods which involve the use of factor H. In preferred embodiments, the immunological disease is selected from the group consisting of an immunoinflammatory disease, sepsis, an autoimmune disease and transplant rejection. The expressions "immunoinflammatory disease", "sepsis", "autoimmune disease" and "transplant rejection" have been described in detailed above and are used with the same meaning in the present invention.

In another preferred embodiment the immunological disease is not an autoimmune disease, preferably is selected from sepsis, transplant rejection, graft-versus-host disease and hypersensitivity diseases.

The prevention and/or treatment of an immunological disease is achieved through the increase of tolerogenic dendritic cell and/or regulatory T cell population.

The expression "increasing tolerogenic dendritic cell population" is understood to mean that the administration of the composition of the invention produces an increase in the number of tolerogenic dendritic cells with respect to an untreated subject. The tolerogenic dendritic cell population is increased by 10%, 20%, 30%, 40%, 50%, 60%, 70%, 80%, 90%, 95%, 97%, 98%, 99%, or 100% in comparison with an untreated subject. The capacity of the composition of the invention of increasing a tolerogenic dendritic cell population can be determined, for instance, as described in examples 9 to 14.

The expression "increasing regulatory T cell population", as used herein, means that the composition of the invention produces an increase in the number of regulatory T cells with respect to an untreated subject. The regulatory T cell population is increased by 10%, 20%, 30%, 40%, 50%, 60%, 70%, 80%, 90%, 95%, 97%, 98%, 99%, or 100% in comparison with an untreated subject. The capacity of the composition of the invention of increasing regulatory T cell population can be determined, for instance, as described in example 17.

Methods for the Generation of a Population of Tolerogenic Dendritic Cells Using Factor H The authors of the present invention have observed that factor H or a functionally equivalent variant thereof, a polynucleotide encoding factor H or a functionally equivalent variant thereof or, a vector comprising said polynucleotide acquire is capable of promoting the maturation of dendritic cell precursors into tolerogenic dendritic cells. Thus, in another aspect, the invention relates to a method for the generation of a population of tolerogenic dendritic cells comprising the steps of
  (i) incubating a population of dendritic precursor cells under conditions adequate for the formation of a population of immature dendritic cells and
  (ii) incubating the population of immature dendritic cells obtained in step (i) under conditions adequate for the formation of mature dendritc cells
wherein steps (i) and/or (ii) are carried out in the presence of a composition of matter selected from the group consisting of:
  (i) Factor H or a functionally equivalent variant thereof,
  (ii) A polynucleotide encoding a Factor H or a functionally equivalent variant thereof and
  (iii) A vector comprising a polynucleotide encoding a Factor H or a functionally equivalent variant thereof.

The expression "tolerogenic dendritic cells", "dendritic precursor cells", "conditions adequate for the formation of a population of immature dendritic cells", "immature dendritic cells", "conditions adequate for the formation of mature dendritc cells" have been described above in detail and are used in the context of the present method with the same meaning As explained above in the context of the method for obtaining a population of tolerogenic dendritic cells using C4BP isoforms lacking the β chain, factor H, the functionally equivalent variant thereof, the polynucleotide encoding a Factor H or a functionally equivalent variant thereof, the vector comprising a polynucleotide encoding a Factor H or a functionally equivalent variant thereof can be contacted with the cells during the differentiation stage (i.e. during the time wherein the dendritic precursor cells differentiate into immature dendritic cells), during the maturation step (i.e. during the time wherein the immature dendritic cells mature into dendritic cells) or during both stages.

The step carried out in the presence of a factor H or of the polynucleotide encoding factor H may be performed in vivo or ex vivo. Generally, in these methods, immature dendritic cells may be exposed to factor H within a range having: a lower end of 0.01, 0.05, 0.1, 0.5, 1, 2, 3, 4, 5, 6, 7, 8, 9, 10, 12, 15, 20, 50, or 100 micrograms per ml of media; and an upper end of 0.05, 0.1, 0.5, 1, 2, 3, 4, 5, 6, 7, 8, 9, 10, 12, 15, 20, 50, 100, or 200 micrograms per ml of media. Most preferably, DC are matured in the presence of 1-10 µg/ml of factor H and, most preferably, at 2, 5 and 10 µg/ml.

In a preferred embodiment, the population of dendritic cell precursors is a monocyte population.

The terms "factor H", "functionally equivalent variant of factor H", "polynucleotide encoding factor H or a functionally equivalent variant thereof", "vector comprising a polynucleotide encoding factor H or a functionally equivalent variant thereof", "dendritic cell", "tolerogenic dendritic cell" have been described in detail above.

Tolerogenic Dendritic Cells of the Invention Obtained Using Factor H and Therapeutic Uses Thereof In another aspect, the invention relates to a tolerogenic cell population obtained using the factor H or the functionally equivalent variant thereof or the polynucleotide encoding factor H or the functionally equivalent variant thereof.

In another aspect, the invention relates to tolerogenic dendritic cells of the invention obtained by differentiating and/or maturing dendritic cells in the presence of a factor H or a functionally equivalent variant thereof, a polynucleotide encoding said polypeptides or a vector comprising said polypeptide.

The tolerogenic dendritic cells according to the invention are characterized by showing one or more of the following features:
  Being HLA-DR$^+$ and/or CD14$^+$. The term "positive", when applied to a given marker, indicates that the level of expression of a particular cell surface marker on a tolerogenic DC produced by a method of the invention is substantially the same as in an appropriate control cell (e.g., a native mature immunostimulatory DC, or a mature immunostimulatory DC obtained via in vitro maturation).
  Being CD80$^-$, CD83$^-$, CD86$^-$, CD1a$^-$, CD40$^-$, CCR7$^-$, IDO$^-$ BIC-1$^-$ and/or SOD2$^-$, The term "negative", when applied to a given marker, indicates that the level of expression of a particular cell surface marker on a tolerogenic DC produced by a method of the invention is decreased by 10%, 20%, 30%, 40%, 50%, 60%, 70%, 80%, 90%, 95%, 97%, 98%, 99%, or 100%, or is undetectable, in comparison to the level of expression of the same cell surface marker on an appropriate control cell (e.g., a native mature immunostimulatory DC, or a mature immunostimulatory DC obtained via in vitro maturation).
  Not secreting or secreting reduced amounts of inflammatory cytokines such as IL-12p70, IL-10, IL-8, IL-6, TNF-α and/or IFN-γ with respect to mature dendritic cells. The term "secrete reduced amounts", when applied to a given cytokine, indicates that the level of secretion of a particular cytokine on a tolerogenic DC produced by a method of the invention is decreased by 10%, 20%, 30%, 40%, 50%, 60%, 70%, 80%, 90%, 95%, 97%, 98%, 99%, or 100%, or is undetectable, in comparison to the level of secretion of the same cell surface marker on an appropriate control cell (e.g., a native mature immunostimulatory DC, or a mature immunostimulatory DC obtained via in vitro maturation).
  Show round morphology. The term "round morphology", as used herein, refers to a morphology wherein the cells show a number of projections protruding from the cell surface which is decreased by 10%, 20%, 30%, 40%, 50%, 60%, 70%, 80%, 90%, 95%, 97%, 98%, 99%, or 100%, or is undetectable, in comparison to the number of projections on an appropriate control cell (e.g., a native mature immunostimulatory DC, or a mature immunostimulatory DC obtained via in vitro maturation). The morphology of a cell can be determined, i.e.

by scanning electron microscopy, as described in example 4 of the present invention, Show reduced endocytic potential when immature. The term "reduced endocytic potential", as used herein, indicates that the endocytic activity of an immature tolerogenic DC is decreased by 10%, 20%, 30%, 40%, 50%, 60%, 70%, 80%, 90%, 95%, 97%, 98%, 99%, or 100% or is undetectable, in comparison to the level of endocytosis on an appropriate control cell (e.g., a native immature immunostimulatory DC). The endocytic capacity can be determined, for instance, as described in example 13 of the present invention, The cell remains viable after the differentiation/maturation process, i.e. they do not undergo apoptosis. The term "viable", as used herein, refers to populations wherein less than 50%, less than 40%, less than 30%, less than 20%, less than 10%, less than 5%, less than 4%, less than 3%, less than 2%, or less than 1% of the cells undergo apoptosis after the treatment with a maturation stimuli (e.g. LPS). Apoptosis can be determined by any method commonly known in the art such as Annexin V/7-ADD staining, caspase-3 activation assay, TUNEL and DNA fragmentation assay, determination of the mitochondrial membrane potential and the like.

Show reduced chemotactic behaviour towards CCL21 with respect to mature dendritic cells. The term "reduced chemotactic behaviour", as used herein, indicates that the level of chemotaxis of a cell produced by a method of the invention towards CCL21 on a tolerogenic DC is decreased by 10%, 20%, 30%, 40%, 50%, 60%, 70%, 80%, 90%, 95%, 97%, 98%, 99%, or 100%, or is undetectable, in comparison to the level of chemotaxis towards the same cytokine on an appropriate control cell (e.g., a native mature immunostimulatory DC, or a mature immunostimulatory DC obtained via in vitro maturation). The chemotactic behaviour of a tolerogenic dendritic cell towards CCL21 can be determined, for instance, as described in example 5 of the present invention, Show a decreased capability of inhibiting allogenic T cell proliferation with respect to mature dendritic cells. The term "decreased capability of inhibiting allogeneic T cell proliferation", as used herein, indicates that the level of proliferation of allogenic T cells contacted with a cell produced by a method of the invention is decreased by 10%, 20%, 30%, 40%, 50%, 60%, 70%, 80%, 90%, 95%, 97%, 98%, 99%, or 100%, or is undetectable, in comparison to the level of proliferation observed in allogeinc T cells contacted with an appropriate control cell (e.g., a native mature immunostimulatory DC, or a mature immunostimulatory DC obtained via in vitro maturation). The capacity of a tolerogenic dendritic cell to inhibit allogeneic T cell proliferation can be carried out, for instance, as described in example 6 of the present invention.

Show a stable immunomodulatory phenotype that is preserved in the presence of pro-inflammatory signals, in contrast to immature DCs. The capacity of a tolerogenic dendritic cell of showing a stable immunomodulatory phenotype can be determined, for instance, as described in example 16 of the present invention.

Show the capability of inhibiting Th1 differentiation under pro-inflammatory conditions with respect to mature dendritic cells. The term "inhibiting Th1 differentiation", as used herein, indicates that the level of Th1 cells produced by the T cells contacted with a cell produced by a method of the invention is decreased by 10%, 20%, 30%, 40%, 50%, 60%, 70%, 80%, 90%, 95%, 97%, 98%, 99%, or 100%, or is undetectable, in comparison to the level of Th1 differentiation observed in T cells contacted with an appropriate control cell (e.g., a native mature immunostimulatory DC, or a mature immunostimulatory DC obtained via in vitro maturation). The capacity of a tolerogenic dendritic cell to inhibit Th1 differentiation can be determined, for instance, measuring the IFN-gamma production as described in example 17 of the present invention.

Show an increased capability of generating regulatory T cells (Treg) with respect to mature dendritic cells. The term "increased capability of generating regulatory T cells", as used herein, indicates that the level of generation of regulatory T cells of T cells contacted with a cell produced by a method of the invention is increased by 10%, 20%, 30%, 40%, 50%, 60%, 70%, 80%, 90%, 95%, 97%, 98%, 99%, or 100%, in comparison to the level of generation of T cells contacted with an appropriate control cell (e.g., a native mature immunostimulatory DC, or a mature immunostimulatory DC obtained via in vitro maturation). The capacity of a tolerogenic dendritic cell to generate regulatory T cells (Treg) can be determined, for instance, as described in example 17 of the present invention. In a preferred embodiment, the tolerogenic dendritic cells according to the invention are HLA-DR$^+$, CD14$^+$, CD80$^-$, CD83$^-$, CD86$^-$, CD1a$^-$, CD40$^-$, CCR7$^-$, IDO$^-$, BIC-1$^-$ and/or SOD2$^-$.

In a preferred embodiment, the tolerogenic cells according to the invention are CD1a$^-$. In another preferred embodiment, the tolerogenic cells according to the invention are CD1a$^-$ and CD86$^-$. In another preferred embodiment, the tolerogenic cells according to the invention are CD1a$^-$, CD86$^-$ and IDO$^-$. In another preferred embodiment, the tolerogenic cells according to the invention are CD1a$^-$, CD86$^-$, IDO$^-$ and apoptosis resistant. In a preferred embodiment, the tolerogenic cells according to the invention are CD1a$^-$ and IDO$^-$. In another preferred embodiment, the tolerogenic cells according to the invention are CD1a$^-$ and apoptosis resistant. In a preferred embodiment, the tolerogenic cells according to the invention are CD86$^-$ and IDO$^-$. In another preferred embodiment, the tolerogenic cells according to the invention are CD86$^-$ and apoptosis resistant. In another preferred embodiment, the tolerogenic cells according to the invention are IDO$^-$ and apoptosis resistant.

In another embodiment, the tolerogenic dendritic cells according to the present invention are capable of inducing Ag-specific tolerance (or hyporesponsiveness) of human memory CD4$^+$ T cells by our tolerogenic, C4BP (b$^-$)- or Factor H-treated DCs.

Feature of the tolerogenic cells according to the present invention are provided in Table 3.

In another aspect, the invention relates to a cell population comprising at least 50%, at least 60%, at least 70%, at least 80%, at least 90%, at least 95%, at least 96%, 97%, 98% or 99% of tolerogenic dendritic cells of the invention; preferably, the cell population comprises at least 80% of tolerogenic dendritic cells of the invention. In yet another aspect, the invention relates to a tolerogenic cell population obtained using the factor H or the functionally equivalent variant thereof or the polynucleotide encoding factor H or the functionally equivalent variant thereof for use in the prevention and/or treatment of a immunological disease.

In another aspect, the invention relates to the use of a tolerogenic cell obtained using the factor H or the polynucleotide encoding factor H for the manufacture of a medicament for the prevention and/or treatment of a immunological disease.

In another aspect, the invention relates to a method for the prevention and/or treatment of an immunological disease in a subject in need thereof which comprises the administration to said subject of a tolerogenic cell obtained using the factor H or the polynucleotide encoding factor H.

In another aspect, the invention relates to a method for increasing regulatory T cell population in a subject in need thereof which comprises the administration to said subject of a tolerogenic dendritic cell population obtained using the factor H or the polynucleotide encoding factor H.

The expression "immunological disease" has been described in detail above and is used in the same meaning in the context of the therapeutic methods which involve the use of factor H. In preferred embodiments, the immunological disease is selected from the group consisting of an immunoinflammatory disease, sepsis, an autoimmune disease and transplant rejection. The expressions "immunoinflammatory disease", "sepsis", "autoimmune disease" and "transplant rejection" have been described in detailed above and are used with the same meaning in the present invention.

The expression "increasing regulatory T cell population", as used herein, means that the tolerogenic dendritic cell population of the invention produces an increase in the number of regulatory T cells with respect to a subject treated with an appropriate control cell (e.g., a native mature immunostimulatory DC, or a mature immunostimulatory DC obtained via in vitro maturation). The regulatory T cell population is increased by 10%, 20%, 30%, 40%, 50%, 60%, 70%, 80%, 90%, 95%, 97%, 98%, 99%, or 100% in comparison with a subject treated with a control cell. The capacity of the tolerogenic dendritic cell population of the invention of increasing regulatory T cell population can be determined, for instance, as described in example 17.

The invention is described in detail by way of the following examples which are to be considered as merely illustrative and not limitative of the scope of the invention.

EXAMPLES

Materials and Methods
Culture Medium and Proteins

RPMI 1640 was supplemented with 100 µg/ml of streptomycin, 100 IU/ml of penicillin and 2 mM L-glutamine (all from Invitrogen, Carlsbad, Calif.) plus/minus 10% heat-inactivated fetal bovine serum (Linus, Cultek, Spain).

We used throughout the study three C4BP isoforms. C4BP $\alpha_7\beta_1$ (in complex with protein S) and C4BP $\alpha_7\beta_0$ were purified from pooled human plasma as previously described (Dahlbäck, B. et al., Biochem J. 1983. 209: 847-856). Both the polymeric recombinant full-length C4BP $\alpha_6\beta_0$ and the mutants lacking individual α-chain CCPs (ΔCCP1-8) were expressed in eukaryotic cells and purified by affinity chromatography (Blom, A. M., L. et al., 2001, J Biol Chem. 276: 27136-27144).

C4BP α-chain CCP6-derived peptides PS6-01, PS6-02, PS6-03, and PS6-04 were synthesized from Caslo Laboratory Aps (Denmark).

Factor H purified from human serum was obtained commercially (10-15-1106, Biopur AG, Switzerland).
Cell Cultures Peripheral blood mononuclear cells (PBMCs) were obtained from buffy coat preparations belonging to healthy donors from the Blood and Tissue Bank (Barcelona, Spain) after Ficoll-Paque™ density centrifugation (GE Healthcare Bio-Sciences AB; Uppsala, Sweden). Monocytes were purified by two different methods: 1) Cells were plated at $1\times10^6$ cells/ml in 60 mm culture plates (Corning, Spain) in RPMI without serum and allowed to adhere for 2 h at 37° C. in 5% $CO_2$. The non-adherent cells were removed by washing in PBS. The final population contained >80% of monocytes, as demonstrated by flow cytometry of anti-CD14-stained isolates. 2) Cells were purified using colloidal super-paramagnetic microbeads conjugated with monoclonal mouse anti-human CD14 antibodies (MACS, Miltenyi Biotec, Auburn, Calif., or EasySep® Positive Selection Cocktail, StemCell Technologies, Grenoble, France). The purity of CD14$^+$ cells was tested by CD14 staining and flow cytometry analysis (>90% CD14$^+$ cells). Monocyte-derived DCs (Mo-DCs) were generated supplementing the monocyte cultures with complete RPMI 1640 medium plus GM-CSF (800 UI/ml) and IL-4 (500 UI/ml) (both from Gentaur, Kampenhout, Belgium) at day 0 and day 3 of culture. For DC maturation, at day 5 iDCs were further stimulated for 48 h with 5 µg/ml LPS (*Escherichia coli* 055.B5, Sigma L2880, Copenhagen, Denmark).

CD3$^+$ T cells were isolated from PBMCs by negative selection using EasySep Human T cell Enrichment Kit (StemCell Technologies, Grenoble, France). CD3$^+$ T-cells were >90% pure, as assessed by CD3 staining using a FACScanto (Becton-Dickinson, Basel, Switzerland).
Antibodies and Flow Cytometry Cell surface phenotypes were analyzed using the following monoclonal antibodies: FITC-conjugated anti-HLA-DR (Immu-357), FITC-conjugated anti-CD83 (HB15a), FITC-conjugated anti-CD14 (RMO52), PE-conjugated anti-CD40 (MAB89), PE-conjugated anti-CD1a (BL6), PE-conjugated anti-CD80 (MAB104), PE-conjugated anti-CD86 (HA5.2B7) (all from Beckman-Coulter), Alexa Fluor 488-conjugated anti-CCR7 (TG8/CCR7, Biolegend, San Diego, Calif.), and the respective isotype controls from the same commercial sources. After washing with PBS, cells were subsequently stained with 3 µl MoAb/$10^5$ cells in 100 µl of FACS buffer (PBS containing 1% BSA and 0.1% sodium azide) for 20 min at room temp. Stained cells were analysed using a FACScalibur (Becton Dickinson). Mo-DCs were gated according to forward scatter (FSC) and side scatter (SSC) parameters. The results were analysed using CellQuestPro software (Becton Dickinson).
C4BP and Factor H Treatments Both the different C4BP isoforms ($\alpha_7\beta_1$, $\alpha_7\beta_0$ and $\alpha_6\beta_0$), and Factor H were added at 2, 5 and 10 µg/ml throughout Mo-DC differentiation, maturation, or both. Namely, for the differentiation assays the proteins were added at day 0 and replenished at day 3. For the maturation assays the proteins were added at day 5, either alone or combined with LPS. Finally, for the differentiation plus maturation assays the proteins were added at days 0, 3 and 5 (at the last time point, combined with LPS).
Scanning Electron Microscopy (SEM)

Monocytes were seeded on glass slides covered with either poly-L-lysine (25 µg/ml) or fibronectin (42 µg/ml), cultured for 5 days in complete RPMI medium supplemented with 800 U/ml GM-CSF, 500 U/ml IL-4, and the C4BP isoforms $\alpha_7\beta_1$, $\alpha_7\beta_0$, or Factor H (10 µg/ml), and further stimulated with LPS for 48 hours in the same medium. The resulting DCs were fixed in 1% paraformaldehyde and 1.25% glutaraldehyde in cacodylate buffer for 2 h. Finally, the cells were post-fixed in 1% $OsO_4$, and dehydrated with graded series of ethanol followed by acetone. After dehydration the cells were dried in a critical-point dryer and coated with gold before observation by scanning electron microscopy (Zeiss DSM940A).

Mixed Leukocyte Reaction

CD3+ T cells ($10^5$/well) and C4BP-treated ($\alpha7\beta1$ and $\alpha7\beta0$), or Factor H-treated, and LPS-activated Mo-DCs were seeded in a 96-well round-bottom plate at various DC:T cell ratios (1:40, 1:80 and 1:160) and cultured in X-VIVO 15 medium (Biowittaker, Walkersville, Md.) supplemented with 100 µg/ml of streptomycin, 100 IU/ml of penicillin and 2 mM L-glutamine (all from Invitrogen) plus 2% Human AB Serum. Allospecific proliferation was measured after 5 days of incubation. At day 4, the co-cultures were irradiated at 5000 rad for 5 min and then [$^3$H]-thymidine (1 µCi/well, Perkin Elmer, Boston, Mass.) was added, followed by incubation for another 16 h. Labeled cells were then harvested onto glass-fiber filters with a Filtermate Harvester (Packard, Meriden, Conn.), and the T cell proliferation rate was determined by the amount of [$^3$H]-thymidine incorporation, which was measured in a TopCount NXT counter (Packard). Results are reported as the mean cpm±SD of thymidine incorporation in quadruplicate culture wells.

Quantitative RT-PCR

Mo-DCs ($10^6$/condition) were harvested at day 7 and the mRNA was extracted using the RNeasy RNA Isolation kit (Qiagen) and incubated with RNase-free DNase I (Ambion, Austin, Tex.) according to the manufacturer's protocol. A two-step real-time RT-PCR technique was used to determine the relative mRNA levels of human CCR7, BIC-1, IDO and SOD2. Reverse transcription reactions were performed with 500 ng of total RNA using the Omniscript RT kit (Qiagen). Quantification of mRNA levels was performed by real-time polymerase chain reaction (PCR) with the use of the Light-Cycler technology (Roche Molecular Biochemicals, Indianapolis, Ind.). The following primers were used: CCR7-f (5'-TGGGCATCTGGATACTAGC-3') (SEQ ID NO:6), CCR7-r (5'-AAGAAAGGGTTGACGCAGC-3') (SEQ ID NO:7); IDO-f (5'-GGTCATGGAGATGTCCGTAA-3') (SEQ ID NO:8); IDO-r (5'-ACCAATAGAGAGACCAG-GAAGAA-3') (SEQ ID NO:9); BIC-1-f (5'-AACCTACCA-GAGACCTTACC-3') (SEQ ID NO:10), BIC-1-r (5'-AT-GCTTCTTTGTCATCCTCC-3') (SEQ ID NO:11); SOD2-f (5'-GACAAACCTCAGCCCTAAC-3') (SEQ ID NO:12), SOD2-r (5'-ACACATCAATCCCCAGCAGT-3') (SEQ ID NO:13), yielding products of 435, 227, 296 bp, and 248 bp, respectively. These gene-specific primer pairs were designed using Oligo 4.0 and Primer 3 software packages (MBI, Cascade, Colo.) and selected to prevent primer-dimer formation.

All samples were normalized with the use of the following primer set for the constitutively expressed human cyclophilin gene: CypA-f (5'-CTCCTTTGAGCTGTTTGCAG-3') (SEQ ID NO:14) and CypA-r (5'-CACCACATGCTTGCCATCC-3') (SEQ ID NO:15) (Pluvinet R. et al., 2004, Blood. 104: 3642-3646). All primers were purchased from Bonsai Technologies (Copenhagen, Denmark).

PCR amplifications were performed in a 20 µl volume containing 2 µl ready-to-use reaction mix, 10×DNA Master SYBR Green I (Roche Molecular Biochemicals); $MgCl_2$ (3 mM for CCR7; 4 mM for BIC-1 and SOD2, and 5 mM for IDO); 0.15 µM of each primer; 5% dimethyl sulfoxide (DMSO); and 75 ng cDNA as template. The amplification program used an initial denaturation at 95° C. for 10 min, followed by 45 cycles: 95° C. for 1 sec; 58° C. (CCR7 and SOD2)/60° C. (BIC-1 and IDO) for 5 sec; 72° C. for 10 sec. The reproducibility of the assay was verified and the expression of the four genes was shown to be within the linear range at the chosen cell concentration.

Chemotaxis Assays

Mo-DCs differentiated and matured (LPS for 48 h) in presence of the C4BP isoforms $\alpha7\beta1$, $\alpha7\beta0$, or Factor H, were tested for migration toward the CCL21 chemokine using transwell assays. Briefly, the lower chambers of transwell plates (polycarbonate filters of 8.0 µm pore size; Costar, Corning, N.Y.) were filled with 400 µl of complete RPMI with or without CCL21 (200 ng/ml). A total of $1\times10^5$ DCs in 100 µl of complete RPMI were added into the upper chamber, and cells were incubated at 37° C. for 2 h. Cells migrated into the lower chambers were harvested and counted with a FACScalibur flow cytometer acquiring events for a fixed time period of 2 min using CellQuest software (Becton Dickinson). The migration assays for all stimulation conditions were performed in duplicate wells. Values are given as percentage of migrated cells relative to the untreated, mDCs (100%).

DC Cytokine Secretion

Concentrations of IL-12p70, TNF-$\alpha$, IFN-$\gamma$, IL-10, IL-6 and IL-8, were determined from DC supernatants treated with the C4BP isoforms $\alpha7\beta1$ and $\alpha7\beta0$ using the Th1/Th2 Flow cytomix Multiplex kit (Bender-Medsystems, Viena, Austria), according to the manufacturer's instructions.

Endocytic Activity

To measure the phagocytic activity of iDCs, $2\times10^5$ cells/ml were resuspended in 100 µl of PBS and incubated with 4 µl of BODIPY FL-conjugated DQ-Ovalbumin (1 mg/ml, DQ-OVA, Molecular Probes, Leiden, Netherlands) at 37° C. or at 0° C. for 15 min. The incubations were stopped by adding 1 ml of cold FACS buffer. The cells were washed two times with cold FACS buffer and their fluorescence analyzed using a FACScalibur flow cytometer (Becton-Dickinson).

Apoptosis Determination

Double staining using with the fluorescent dyes Annexin V (Annexin V-PE Apoptosis Detection Kit I, BD Pharmigen, San Diego, Calif.) and 7-amino-actinomycin D (7-ADD) (BD Pharmigen), and flow cytometry analysis, was employed to assess the viability/apoptosis status of C4BP $\alpha_7\beta_1$-, C4BP $\alpha_7\beta_0$-, recC4BP $\alpha_6\beta_0$-, or Factor H-treated and untreated Mo-DCs.

Intracellular Cytokine Staining

Mononuclear cells isolated from healthy donors were seeded in 96-well round bottom plates (Nunc) at a density of $1\times10^5$ cells/well and stimulated for 6 days with allogeneic DCs ($5\times10^3$ DCs/well). Then, total cells were stimulated with 50 ng/ml phorbol 12-myristate 13-acetate (PMA, Sigma) plus 500 ng/ml ionomycin (Sigma) for 5 h in the presence of 10 µg/ml brefeldin A (Sigma). After stimulation, cells were washed with PBS and fixed and permeabilized using an IntraStain kit (Dako) and incubated for 28 min at RT with anti-human IFN-gamma APC mAb (eBioscience). Cells were washed and analysed using a FACScanto II flow cytometer (Becton Dickinson) equipped with FACSDiva software (Becton-Dickinson).

Determination of CD4+ CD127$^{low/negative}$ CD25$^{high}$ and Foxp3+ T Cells

CD3+ T lymphocytes were purified from mononuclear cells by negative selection using an EasySep® Human T Cell Enrichment Kit (StemCell Technologies) following the manufacturer's instructions. Purity was >95% in all experiments. Enriched T cells were plated ($10^5$ cells/well) in 96-well round-bottom plates. After 5 days of co-culture (1DC:40T), we used flow cytometry to determine the percentages of Tregs defined as CD4+, CD127$^{low/negative}$, CD25$^{high}$ and intracellular Foxp3+ (Human Regulatory T Cell Staining Kit; eBioscience, San Diego, Calif., USA). Stained cells were analysed using a FACSCanto II (Becton Dickinson) and the results were analysed using FlowJo software (Tree Star, Inc, OR, USA).

Statistical Analysis

Results are presented as means+/−SD. Mo-DC variables under different experimental conditions respect to a reference condition (usually mDCs or iDCs) were compared using the unpaired Student's t test, considering p<0.05 as significant.

Example 1

Figure 1:
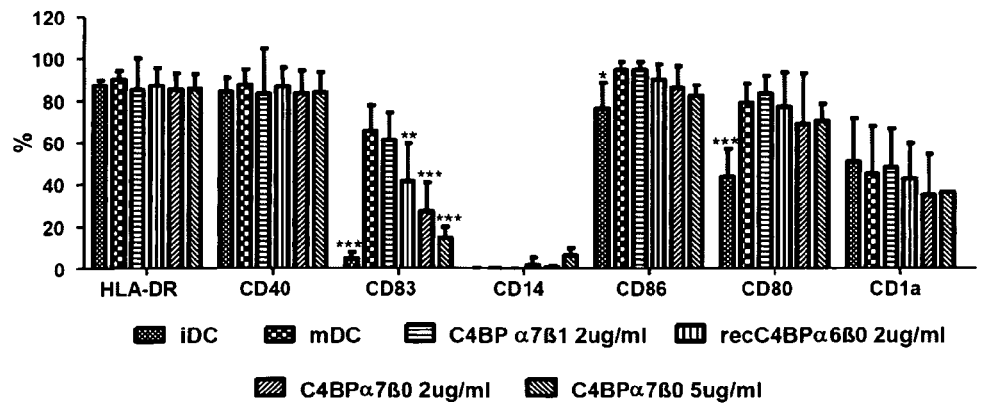
FIG. 1. C4BP isoforms lacking beta chain down-regulate the activation phenotype of human Mo-DCs C4BP $\alpha7\beta0$ and recombinant $\alpha6\beta0$, but not $\alpha7\beta1$, inhibit up-regulation of key surface markers from human Mo-DCs. Human Mo-DCs were incubated throughout their differentiation and maturation process with the indicated concentrations of the C4BP isoforms. DC maturation was achieved by LPS treatment (see Materials and Methods for details). Cells were then collected, washed, and analyzed by flow cytometry for cell surface expression of CD14, CD40, CD80, CD83, CD86, CD1a and HLA-DR. Columns represent the percentage of positive cells (A), and the MFI (B) for the different surface markers. iDC, untreated, immature DCs; mDC, untreated, LPS-matured DCs. The results shown are the mean+/−SD from 8 independent experiments (*, $p<0.05$; , $p<0.01$; *, $p<0.001$ respect to mDC).
Figure 1:
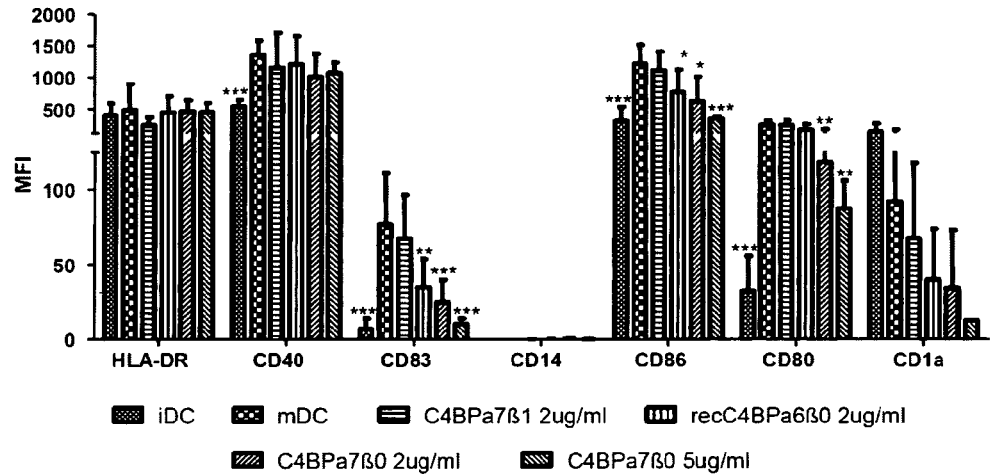
Figure 2:
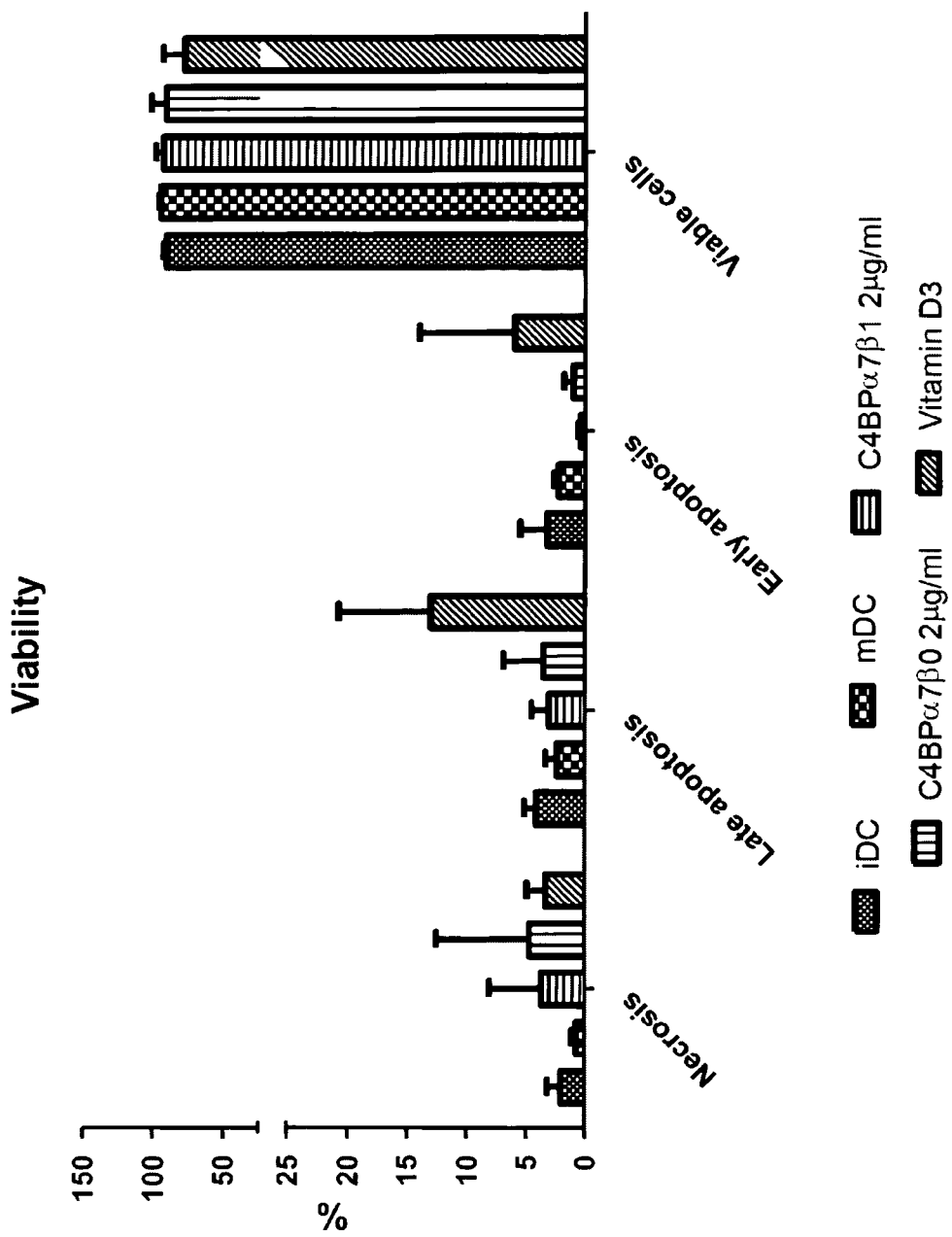
FIG. 2. C4BP treatment does not affect the viability of human Mo-DCs

C4BP Isoforms Lacking Beta Chain Down-Regulate the Activation Phenotype of Human Mo-DCs We first assessed whether the main natural C4BP isoforms $\alpha7\beta1$ and 0130, plus the recombinant C4BP $\alpha6\beta0$ impact on expression of different monocyte and DC surface markers, including CD14, HLA-DR, CD40, CD80, CD83, CD86, and CD1a. The data from eight independent experiments were analyzed using the unpaired Student t test (FIG. 1). Interestingly, Mo-DC co-incubation with C4BP throughout their 7-day differentiation and maturation process revealed significant phenotypic differences among the different C4BP isoforms. Thus, while the major C4BP $\alpha7\beta1$ isoform had no effect on the expression of any of the above markers on LPS-matured DCs, the C4BP $\beta^-$ isoforms ($\alpha7\beta0$ and recombinant $\alpha6\beta0$) significantly down-regulated CD83, CD86, CD80 and CD1a in a dose-dependent manner. Conversely, expression of HLA-DR and CD40 on Mo-DCs was unaltered by C4BP $\beta^-$ isoform treatment. Together, these data are evidence that the C4BP $\beta^-$ isoforms have the potential to modify pro-inflammatory MoDC differentiation/maturation as judged by the expression pattern of various cell surface markers. Moreover, Mo-DCs treated with the different C4BP isoforms remained highly viable throughout the differentiation/maturation process, as assessed by Annexin V/7-ADD staining, with less than 10% of apoptotic cells evidenced at 48 h after LPS-mediated DC maturation (FIG. 2).

Example 2

Human Mo-DCs Exposed to C4BP Isoforms Lacking Beta Chain Express Less CCR7 and DC Maturation Markers IDO and BIC-1

To further assess the effect of the C4BP iso forms on key transcripts conforming the molecular signature of maturing DCs [Jin et al., 2010, J Transl Med. 8: 4], the expression of the chemokine receptor CCR7, involved in DC trafficking, the immunoregulatory enzyme IDO, involved in tryptophan metabolism, and the BIC-1 gene, coding for miR-155, an important miRNA involved in immune function, were analyzed by RT-qPCR. All these molecular biomarkers were found up-regulated upon LPS-mediated Mo-DC maturation. Nevertheless, Mo-DCs pretreated with C4BP $\alpha7\beta0$ and C4BP $\alpha6\beta0$, but not with C4BP $\alpha7\beta1$, significantly down-regulated the above transcriptional profile, reaching CCR7, IDO and BIC-1 transcript levels equivalent to those from immature DCs (FIG. 3A). Moreover, C4BP $\beta^-$ isoform treatment induced consistent down-regulation of the surface receptor CCR7 on Mo-DCs (FIG. 3B).

Example 3

C4BP Isoforms Lacking Beta Chain Inhibit the Release of Inflammatory Cytokines by LPS-Matured Human Mo-DCs We next assessed whether the effect of the different C4BP iso forms on Mo-DC phenotype was accompanied by changes in their release of cytokines (IL-12p70, IL-10, IL-8, IL-6, TNF-$\alpha$, and IFN-$\gamma$) (FIG. 4). Compared to untreated iDCs, secretion of each of these cytokines was up-regulated when iDCs were matured with LPS. Mo-DCs pre-treated with C4BP $\alpha7\beta1$ secreted the same cytokine levels than untreated Mo-DCs upon maturation. In contrast, pre-treatment with any of the C4BP $\beta^-$ iso forms prevented the release of IL-12p70, TNF-$\alpha$ and IFN-$\gamma$; reduced the release of IL-8 and IL-6, and increased the production of IL-10. Thus, pro-inflammatory cytokine production upon LPS-mediated Mo-DC stimulation was significantly reduced in C4BP $\beta^-$-treated DCs.

Example 4

C4BP Isoforms Lacking Beta Chain Modify the Morphology of Human Mo-DCs

Scanning electron microscopy (SEM) was employed to assess the detailed surface morphology of Mo-DCs (FIG. 5). Before LPS exposure, untreated iDCs were essentially round, whereas after 48 h of LPS maturation the dendritic morphology became evident, with numerous long projections protruding from the cell surface. Again, C4BP $\alpha7\beta1$-treated Mo-DCs had an analogous appearance than untreated Mo-DCs upon LPS-stimulation. Conversely, Mo-DC treatment with both C4BP $\alpha7\beta0$ (FIG. 5) and C4BP $\alpha6\beta0$ (not shown) reversed the "porcupine like" DC morphology resulting upon LPS induction.

Example 5

C4BP Isoforms Lacking Beta Chain Alter the Chemotaxis of Human Mo-DCs

Maturation signals determine the expression of distinct Mo-DC functions, such as migration to lymph node-directing chemokines. As previously shown, C4BP $\beta^-$ iso form treatment down-regulated the chemokine receptor CCR7. Reduced surface CCR7 expression, in turn, halted the migration of LPS-matured Mo-DCs towards the chemokine CCL21 (FIG. 6). In contrast, LPS maturation of both untreated and C4BP $\alpha7\beta1$-treated Mo-DCs induced maximal migration in response to CCL21.

Example 6

Human Mo-DCs Exposed to C4BP Isoforms Lacking Beta Chain Inhibit Allogeneic T Cell Proliferation Given that C4BP $\beta^-$ isoforms were found to impact on phenotypic maturation and the amount of inflammatory cytokines released by Mo-DCs, we next examined the immunostimulatory capacity of Mo-DCs exposed to the major C4BP isoforms. When Mo-DCs were pre-incubated with the C4BP $\alpha7\beta1$ isoform and matured with LPS, maximal allogeneic T cell proliferation was observed, similar to that obtained using untreated, LPS-matured Mo-DCs. By contrast, mature Mo-DCs pre-incubated with C4BP $\alpha7\beta0$ induced significantly less T cell proliferation, approaching the levels observed using iDCs (FIG. 7). An analogous result was obtained using naïve T cells (data not shown).

Example 7

The CCP6 Domain of C4BPA is Necessary for the "Tolerogenic" Activity of C4BP Over Human Mo-DCs We then aimed to further characterize the structural requirements of the C4BP β⁻ isoforms for their immunomodulatory or "tolerogenic" activity over Mo-DCs. Thus, recombinant C4BP isoforms ($\alpha_6\beta_0$) lacking individual CCP domains were tested for their ability to down-regulate the activation phenotype of Mo-DCs. As shown in FIG. 8, all individual deletion mutants but one, ΔCCP6, were able to significantly prevent the upregulation of the CD83 maturation marker upon LPS induction. Conversely, C4BP ΔCCP6-treated Mo-DCs behaved like untreated or C4BP α7β1-treated Mo-DCs upon LPS induction, upregulating CD83 expression (FIG. 8), and did also not prevent the induction of other typical maturation traits like upregulation of molecular biomarkers (IDO), pro-inflammatory cytokine secretion, or changes in surface morphology (data not shown). Thus, the C4BP α-chain CCP6 domain is necessary for the immunomodulatory activity of the C4BP β⁻ isoforms in DCs.

Example 8

CCP6-Based Peptide PS6-04 Prevents the Maturation Phenotype of Human Mo-DCs

We generated four synthetic peptides (PS6-01, PS6-02, PS6-03, and PS6-04) encompassing the whole CCP6 domain sequence, acetylated at the N-terminus and amidated at the C-terminus, where the Cys amino acids were substituted by Ser, and tested them to mimic the immunomodulatory or "tolerogenic" activity of the C4BP β⁻ isoforms over LPS-stimulated Mo-DCs (FIG. 9). Two of the peptides, PS6-02 and PS6-03, seemed to prevent CD83 upregulation on LPS-matured Mo-DCs. PS6-02 was toxic to the DCs. Thus, the small 14-mer peptide PS6-04 at 100 μM induced a comparable effect than its C4BP α6β0 counterpart over Mo-DCs.

Example 9

Factor H Down-Regulates the Activation Phenotype of Human Mo-DCs

We first assessed whether human plasma-purified Factor H impact on expression of different monocyte and DC surface markers, including CD14, HLA-DR, CD40, CD80, CD83, CD86, and CD1a. The data of five independent experiments were analyzed using the unpaired Student t test (FIG. 10). Interestingly, Mo-DC co-incubation with Factor H throughout their differentiation and maturation process revealed significant phenotypic differences respect to untreated Mo-DCs. Thus, Factor H significantly down-regulated CD83, CD86, CD80, CD40 and CD1a in a dose-dependent manner. Conversely, expression of HLA-DR and CD14 experienced a slightly increase. Together, these data are evidence that Factor H has the potential to modify pro-inflammatory Mo-DC differentiation/maturation, as judged by the expression pattern of various cell surface markers. Moreover, Mo-DCs treated with Factor H remained highly viable throughout the differentiation/maturation process, as assessed by Annexin V/7-ADD staining, with less than 10% of apoptotic cells evidenced at 48 h after LPS-mediated DC maturation (FIG. 11).

Example 10

Human Mo-DCs Exposed to Factor H Express Less CCR7 and DC Maturation Markers IDO, BIC-1 and SOD2

To further assess the effect of the Factor H on key transcripts conforming the molecular signature of maturing DCs (Jin et al., 2010, J. Trans. Med, 8:4), we analyzed by RT-qPCR the expression of the chemokine receptor CCR7, involved in DC trafficking, the immunoregulatory enzyme IDO, involved in tryptophan metabolism, the BIC-1 gene, coding for miR-155, an important miRNA involved in immune function, and the anti-oxidant enzyme SOD2. All these molecular biomarkers were found up-regulated upon LPS-mediated Mo-DC maturation. Nevertheless, Mo-DCs pretreated with Factor H significantly down-regulated the above transcriptional profile, driving CCR7, IDO, BIC-1 and SOD2 transcript levels even below to those from immature DCs (FIG. 12A). Moreover, Factor H treatment induced consistent down-regulation of the surface receptor CCR7 on Mo-DCs (FIG. 12B).

Example 11

Factor H Inhibits the Release of Inflammatory Cytokines by LPS-Matured Human Mo-DCs We next assessed whether the effect of Factor H was accompanied by changes in their release of cytokines (IL-12p70, IL-10, IL-8, IL-6, TNF-α, and IFN-γ) (FIG. 13). Compared to untreated iDCs, secretion of each of these cytokines was up-regulated when iDCs were matured with LPS. Pre-treatment with Factor H prevented the release of all above-mentioned inflammatory cytokines, whose levels remained close to those from untreated iDCs. Thus, pro-inflammatory cytokine production upon LPS-mediated Mo-DC stimulation was significantly reduced in Factor H-treated DCs.

Example 12

Factor H Modifies the Morphology of Human Mo-DCs

Scanning electron microscopy (SEM) was employed to assess the detailed surface morphology of Mo-DCs (FIG. 14). Before LPS exposure, untreated iDCs were essentially round, whereas after 48 h of LPS maturation the dendritic morphology became evident, with numerous long projections protruding from the cell surface. Again, Mo-DC treatment with Factor H (FIG. 14) reversed the "porcupine like" DC morphology resulting upon LPS induction.

Example 13

Factor H Reduces the Endocytic Potential of iDCs

We next examined whether Factor H has an impact on the endocytic activity of immature Mo-DCs. Mo-DCs were incubated with fluorescent DQ-OVA at 37° C. to measure specific uptake and at 4° C. to quantify nonspecific binding. Factor H significantly reduced the endocytic capacity of iDCs (FIG. 15). Strikingly, Factor H reduced iDC phagocytosis to the level of phagocytosis observed in mDCs (data not shown). At 4° C. no incorporation of DQ-OVA by immature Mo-DCs was observed. These data indicate that Factor H reduces the endocytic capacity of iDCs.

Example 14

Factor H Alters the Chemotaxis of Human Mo-DCs

Maturation signals determine the expression of distinct Mo-DC functions, such as migration to lymph node-directing chemokines. As previously shown, Factor H treatment down-regulated the chemokine receptor CCR7. Reduced surface CCR7 expression, in turn, halted the migration of LPS-matured Mo-DCs towards the chemokine CCL21 (FIG.

16). In contrast, LPS maturation of untreated Mo-DCs induced maximal migration in response to CCL21.

Example 15

Human Mo-DCs Exposed to Factor H Inhibit Allogeneic T Cell Proliferation

Given that Factor H was found to impact on the activation phenotype and on the amount of inflammatory cytokines released by Mo-DCs, we next examined the immunostimulatory capacity of Mo-DCs exposed to Factor H. When untreated, LPS-matured Mo-DCs were employed in the mixed leukocyte reaction, maximal allogeneic T cell proliferation was observed. By contrast, Mo-DCs pre-incubated with Factor H induced significantly less T cell proliferation, approaching the levels observed using iDCs (FIG. 17). An analogous result was obtained using naïve T cells (data not shown).

Example 16

C4BP (β–) and FH Induce a Stable Phenotype on DCs

Due to their potential use in the clinical setting, we aimed to study whether an ulterior activation of C4BP(β–)- or FH-treated and LPS-matured DCs would modify the phenotype of these tolerogenic DCs. Therefore, both untreated and C4BP(β–)- or FH-treated DCs were matured with LPS, as previously mentioned, and then re-stimulated without immunomodulatory agents (C4BP(β–) or FH) using TNF-alpha+IFN-gamma for 24 h. Re-stimulation using TNF-alpha+IFN-gamma did not induce significant changes neither in DC viability (not shown), nor in the DC phenotype regarding the CD83 and CD86 markers (FIG. 18). These tolerogenic C4BP(β–)- or FH-treated DCs were thus phenotypically refractory to secondary stimulation, confirming their stable non-proinflammatory profile.

Example 17

C4BP(β–)- or FH-Treated and LPS-Matured DCs Prevent CD4+Th1 Polarization while Inducing Treg Phenotype on Allogeneic T Cells After confirming that C4BP(β–)- and FH-treated and LPS-matured DCs were able to inhibit allogeneic T cell proliferation, we sought to gain insight into the cytokines secreted by these responding T cells, CFSE$^{low}$ alloproliferative T lymphocytes were re-stimulated with PMA+ionomycin and IFN-gamma production was measured by intracellular staining. These results confirmed a significant reduction of about 50-60% in IFN-gamma production relative to LPS-matured, untreated DCs (FIG. 19).

Finally, the presence of Treg cells, defined as CD4+ CD127$^{low}$CD25$^{high}$ and Foxp3+, was estimated in these culture conditions. After one round of stimulation for 6 days, we analysed the induction of CD4+Foxp3+ and CD25$^{high}$, CD127$^{low/negative}$ cells as shown in FIG. 20. Both T cells stimulated with C4BP(β–)-treated and LPS-matured DCs, and T cells stimulated with FH-treated and LPS-matured DCs, showed a significant increase of the percentage of CD4+Foxp3+ and CD25$^{high}$, CD127$^{low/negative}$ cells, and this increase was analogous to that achieved with untreated immature DCs.

Example 18

Adoptively Transferred C4BP(β$^-$)-Treated or Factor H-Treated DCs Suppress Alloimmunity In Vivo We assessed the in vivo tolerogenic or regulatory capacity of C4BP(β$^-$)-treated or Factor H-treated monocyte-derived DCs in a human xeno-graft-versus-host disease (xeno-GvHD) model (King et al. (2009) Clin. Exp. Immunol. 157: 104-118). Intravenous injection of human peripheral blood mononuclear cells (PBMCs; 10×10$^6$/mouse) induced xeno-GvHD in NSG immunodeficient mice (The Jackson Laboratory) (8-12 weeks of age) (median survival time 30-40 days). Co-transfer (preventive study) or late infusion (at 25 days after PBMC injection, or when the earliest pathological signs are manifested in the PBMC-injected animals, e.g., weight loss, hunched posture, fur loss, reduced mobility, . . . ) (therapeutic study) of C4BP(β$^-$)-treated or Factor H-treated monocyte-derived DCs (5×10$^5$/mouse) with PBMCs significantly prolonged survival time, versus animals injected with PBMCs alone, whereas no significant protection was conferred by transfer of untreated, or C4BP (β+)-treated DCs.

The invention claimed is:

1. A method for the treatment of an immunological disease caused by an undesired activation of the immune system by increasing tolerogenic dendritic cell and/or regulatory T cell populations in a subject in need thereof comprising the administration to said subject of a C4BP isoform lacking the beta chain wherein if at least one of the alpha-chains forming said isoform is a deletion mutant which lacks at least one of the CCP regions, the CCP6 region is preserved in said alpha-chain.

2. The method according to claim 1 wherein all the alpha chains in the C4BP isoform are full-length alpha-chains.

3. The method according to claim 1, wherein the immunological disease is selected from an immunoinflammatory disease and an autoimmune disease.

4. The method according to claim 1, wherein the immunological disease is selected from the group consisting of rheumatoid arthritis, graft-versus-host disease, systemic lupus erythematosus, and ulcerative colitis.

5. A method for the treatment of an immunological disease caused by an undesired activation of the immune system by increasing tolerogenic dendritic cell and/or regulatory T cell populations in a subject in need thereof comprising the administration to said subject of a C4BP isoform lacking the beta chain, wherein the C4BP isoform is selected from the group consisting of $\alpha_7\beta_0$ and $\alpha_6\beta_0$.

6. The method according to claim 5, wherein the immunological disease is selected from the group consisting of an immunoinflammatory disease, sepsis, an autoimmune disease, transplant rejection, graft-versus-host disease and a hypersensitivity disease.

7. The method according to claim 6 wherein the immunological disease is selected from the group consisting of:
(i) an immunoinflammatory disease selected from the group consisting of infarct or stroke, atherosclerosis, pulmonary fibrosis, acute respiratory distress syndrome, asthma, cancer, pre-eclampsia and eclampsia;
(ii) sepsis;
(iii) an autoimmune disease selected from the group consisting of: autoimmune blood diseases, autoimmune diseases of the musculature, autoimmune diseases of the ear, autoimmune eye diseases, autoimmune diseases of the kidney, autoimmune skin diseases, cardiovascular autoimmune diseases, endocrine autoimmune diseases, autoimmune gastroenteric diseases, autoimmune nervous diseases and a systemic autoimmune disease selected from the group consisting of systemic lupus erythematosus, antiphospholid syndrome, autoimmune lymphoproliferative disease, autoimmune polyendocrinopathy, Bechet's disease, Goodpasture's disease, sarcoidosis, scleroderma, Sjogren's syndrome and psoriasis;
(iv) transplant rejection;
(v) graft-versus-host disease; and
(vi) a hypersensitivity disease.

8. The method according to claim 7 wherein the autoimmune blood disease is selected from the group consisting of pernicious anemia, autoimmune hemolytic anemia, aplastic anemia, idiopathic thrombocytopenic purpura and ankylosing spondylitis; the autoimmune disease of the musculature is selected from the group consisting of polymyositis and dermatomyositis; the autoimmune disease of the ear is selected from the group consisting of autoimmune hearing loss and Meniere's syndrome; the autoimmune eye disease is selected from the group consisting of Mooren's disease, Reiter's syndrome and Vogt-Koyanagi-Harada disease; the autoimmune disease of the kidney is selected from the group consisting of glomerulonephritis and IgA nephropathy; the autoimmune skin disease is selected from the group consisting of pemphigus or autoimmune bullous diseases, pemphigus vulgaris, pemphigus foliaceus, pemphigus erythematosus, bullous pemphigoid, vitiligo, epidermolysis bullosa acquisita, psoriasis and alopecia areata; the cardiovascular autoimmune disease is selected from the group consisting of autoimmune myocarditis, vasculitis, Churg-Strauss syndrome, giant cells arteritis, Kawasaki's disease, polyarteritis nodosa, Takayasu's arteritis and Wegener's granulomatosis; the endocrine autoimmune disease is selected from the group consisting of Addison's disease, autoimmune hypoparathyroidism, autoimmune hypophysitis, autoimmune oophoritis, autoimmune orchitis, Grave's Disease, Hashimoto's thyroiditis, polyglandular autoimmune syndrome type 1 (PAS-I), polyglandular autoimmune syndrome type 2 (PAS-2) and polyglandular autoimmune syndrome type 3 (PAS-3); the autoimmune gastroenteric disease is selected from the group consisting of autoimmune hepatitis, primary biliary cirrhosis, inflammatory bowel disease, celiac disease and Crohn's disease; the autoimmune nervous disease is selected from the group consisting of multiple sclerosis, myasthenia gravis, Guillan-Barre syndrome and chronic inflammatory demyelinating neuropathy.

9. The method according to claim 7 wherein the autoimmune disease is systemic lupus erythematosus.

10. The method according to claim 7 wherein the immunological disease is transplant rejection.

11. The method according to claim 7 wherein the immunological disease is graft-versus-host disease.

12. The method according to claim 7 wherein the autoimmune disease is an autoimmune disease of the kidney.

13. A preventive method for the treatment of a subject at risk for developing an immunological disease by increasing tolerogenic dendritic cell and/or regulatory T cell populations, comprising:
the administration to said subject of a C4BP isoform lacking the beta chain,
wherein if at least one of the alpha-chains forming said isoform is a deletion mutant which lacks at least one of the CCP regions, the CCP6 region is preserved in said alpha-chain;
wherein said immunological disease is caused by an undesired activation of the immune system.

14. A method for preventing the release of an inflammatory cytokine from dendritic cells in a subject in need thereof, comprising:
the administration to said subject of a C4BP isoform lacking the beta chain,
wherein if at least one of the alpha-chains forming said isoform is a deletion mutant which lacks at least one of the CCP regions, the CCP6 region is preserved in said alpha-chain;
wherein said inflammatory cytokine is IL-12p70, TNF-α, IFN-γ, or a combination thereof.

15. A preventive method for the treatment of a subject at risk for developing an immunological disease by increasing tolerogenic dendritic cell and/or regulatory T cell populations, comprising:
the administration to said subject of a C4BP isoform lacking the beta chain, wherein the C4BP isoform is selected from the group consisting of $\alpha_7\beta_0$ and $\alpha_6\beta_0$;
wherein said immunological disease is caused by an undesired activation of the immune system.

16. A method for preventing an increase in expression of a dendritic cell surface marker in a subject in need thereof, comprising:
the administration to said subject of a C4BP isoform lacking the beta chain,
wherein if at least one of the alpha-chains forming said isoform is a deletion mutant which lacks at least one of the CCP regions, the CCP6 region is preserved in said alpha-chain;
wherein said dendritic cell surface marker is CD83, CD86, or a combination thereof.

* * * * *

SEQUENCE LISTING

```
<160> NUMBER OF SEQ ID NOS: 15

<210> SEQ ID NO 1
<211> LENGTH: 62
<212> TYPE: PRT
<213> ORGANISM: Artificial
<220> FEATURE:
<223> OTHER INFORMATION: C4BP alpha chain CCP6 region

<400> SEQUENCE: 1

Leu Cys Cys Pro Glu Pro Lys Leu Asn Asn Gly Glu Ile Thr Gln His
1               5                   10                  15

Arg Lys Cys Arg Pro Ala Asn His Cys Val Tyr Phe Tyr Gly Asp Glu
            20                  25                  30

Ile Ser Phe Ser Cys His Glu Thr Cys Arg Phe Ser Ala Ile Cys Gln
        35                  40                  45

Gly Asp Gly Thr Trp Ser Pro Arg Thr Pro Ser Cys Gly Asp
    50                  55                  60
```

```
<210> SEQ ID NO 2
<211> LENGTH: 30
<212> TYPE: PRT
<213> ORGANISM: Artificial
<220> FEATURE:
<223> OTHER INFORMATION: PS6-01

<400> SEQUENCE: 2

Leu Ser Ser Pro Glu Pro Lys Leu Asn Asn Gly Glu Ile Thr Gln His
1               5                   10                  15

Arg Lys Ser Arg Pro Ala Asn His Ser Val Tyr Phe Tyr Gly
            20                  25                  30

<210> SEQ ID NO 3
<211> LENGTH: 30
<212> TYPE: PRT
<213> ORGANISM: Artificial
<220> FEATURE:
<223> OTHER INFORMATION: PS6-02

<400> SEQUENCE: 3

His Arg Lys Ser Arg Pro Ala Asn His Ser Val Tyr Phe Tyr Gly Asp
1               5                   10                  15

Glu Ile Ser Phe Ser Ser His Glu Thr Ser Arg Phe Ser Ala
            20                  25                  30

<210> SEQ ID NO 4
<211> LENGTH: 30
<212> TYPE: PRT
<213> ORGANISM: Artificial
<220> FEATURE:
<223> OTHER INFORMATION: PS6-03

<400> SEQUENCE: 4

Glu Ile Ser Phe Ser Ser His Glu Thr Ser Arg Phe Ser Ala Ile Ser
1               5                   10                  15

Gln Gly Asp Gly Thr Trp Ser Pro Arg Thr Pro Ser Ser Gly
            20                  25                  30

<210> SEQ ID NO 5
<211> LENGTH: 14
<212> TYPE: PRT
<213> ORGANISM: Artificial
<220> FEATURE:
<223> OTHER INFORMATION: PS6-04

<400> SEQUENCE: 5

Ile Thr Gln His Arg Lys Ser Arg Pro Ala Asn His Ser Val
1               5                   10

<210> SEQ ID NO 6
<211> LENGTH: 19
<212> TYPE: DNA
<213> ORGANISM: Artificial
<220> FEATURE:
<223> OTHER INFORMATION: Primer CCR7-f

<400> SEQUENCE: 6
tgggcatctg gatactagc                                              19

<210> SEQ ID NO 7
<211> LENGTH: 19
<212> TYPE: DNA
<213> ORGANISM: Artificial
<220> FEATURE:
<223> OTHER INFORMATION: Primer CCR7-r
```

-continued

```
<400> SEQUENCE: 7
aagaaagggt tgacgcagc                                                    19

<210> SEQ ID NO 8
<211> LENGTH: 20
<212> TYPE: DNA
<213> ORGANISM: Artificial
<220> FEATURE:
<223> OTHER INFORMATION: Primer IDO-f

<400> SEQUENCE: 8
ggtcatggag atgtccgtaa                                                   20

<210> SEQ ID NO 9
<211> LENGTH: 23
<212> TYPE: DNA
<213> ORGANISM: Artificial
<220> FEATURE:
<223> OTHER INFORMATION: IDO-r

<400> SEQUENCE: 9
accaatagag agaccaggaa gaa                                               23

<210> SEQ ID NO 10
<211> LENGTH: 20
<212> TYPE: DNA
<213> ORGANISM: Artificial
<220> FEATURE:
<223> OTHER INFORMATION: BIC-1-f

<400> SEQUENCE: 10
aacctaccag agaccttacc                                                   20

<210> SEQ ID NO 11
<211> LENGTH: 20
<212> TYPE: DNA
<213> ORGANISM: Artificial
<220> FEATURE:
<223> OTHER INFORMATION: BIC-1-r

<400> SEQUENCE: 11
atgcttcttt gtcatcctcc                                                   20

<210> SEQ ID NO 12
<211> LENGTH: 19
<212> TYPE: DNA
<213> ORGANISM: Artificial
<220> FEATURE:
<223> OTHER INFORMATION: Primer SOD2-f

<400> SEQUENCE: 12
gacaaacctc agccctaac                                                    19

<210> SEQ ID NO 13
<211> LENGTH: 20
<212> TYPE: DNA
<213> ORGANISM: Artificial
<220> FEATURE:
<223> OTHER INFORMATION: Primer SOD2-r

<400> SEQUENCE: 13
acacatcaat ccccagcagt                                                   20

<210> SEQ ID NO 14
```

```
<211> LENGTH: 20
<212> TYPE: DNA
<213> ORGANISM: Artificial
<220> FEATURE:
<223> OTHER INFORMATION: Primer CypA-f

<400> SEQUENCE: 14
ctcctttgag ctgtttgcag                                                     20

<210> SEQ ID NO 15
<211> LENGTH: 19
<212> TYPE: DNA
<213> ORGANISM: Artificial
<220> FEATURE:
<223> OTHER INFORMATION: Primer CypA-r

<400> SEQUENCE: 15
caccacatgc ttgccatcc                                                      19
```